US012343339B2

(12) United States Patent
Winkler et al.

(10) Patent No.: US 12,343,339 B2
(45) Date of Patent: Jul. 1, 2025

(54) BISAMINOQUINOLINES AND BISAMINOACRIDINES COMPOUNDS AND METHODS OF THEIR USE

(71) Applicant: THE TRUSTEES OF THE UNIVERSITY OF PENNSYLVANIA, Philadelphia, PA (US)

(72) Inventors: Jeffrey Winkler, Wynnewood, PA (US); Ravi K. Amaravadi, Media, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 822 days.

(21) Appl. No.: 17/613,648

(22) PCT Filed: May 24, 2020

(86) PCT No.: PCT/US2020/034446
§ 371 (c)(1),
(2) Date: Nov. 23, 2021

(87) PCT Pub. No.: WO2020/243037
PCT Pub. Date: Dec. 3, 2020

(65) Prior Publication Data
US 2022/0241267 A1 Aug. 4, 2022

Related U.S. Application Data

(60) Provisional application No. 62/852,693, filed on May 24, 2019.

(51) Int. Cl.
A61K 31/473 (2006.01)
A61K 31/4706 (2006.01)
A61P 35/00 (2006.01)
C07D 215/42 (2006.01)
C07D 219/10 (2006.01)

(52) U.S. Cl.
CPC ........ A61K 31/473 (2013.01); A61K 31/4706 (2013.01); A61P 35/00 (2018.01); C07D 215/42 (2013.01); C07D 219/10 (2013.01)

(58) Field of Classification Search
CPC ... A61K 31/473; A61K 31/4706; A61P 35/00; C07D 215/42; C07D 219/10
See application file for complete search history.

(56) References Cited

U.S. PATENT DOCUMENTS

| 2014/0050696 | A1 | 2/2014 | Amaravadi et al. | |
| 2016/0106648 | A1 | 4/2016 | Nagamoottoo-Casse et al. | |
| 2016/0168009 | A1* | 6/2016 | Vitorica Murguia | C03C 1/002 501/29 |
| 2016/0168099 | A1* | 6/2016 | Amaravadi | C07D 401/14 546/159 |
| 2017/0275252 | A1 | 9/2017 | Amaravadi et al. | |

FOREIGN PATENT DOCUMENTS

| WO | 2012/149186 A2 | 11/2012 |
| WO | 2016/022956 A1 | 2/2016 |
| WO | 2016/168721 A1 | 10/2016 |

OTHER PUBLICATIONS

Nature Reviews Cancer, Sep. 2017, vol. 17, pp. 528-542 (Year: 2017).*
Cancer Prevention Research (Philadelphia), Jul. 2011; 4 (7): 973-983 (Year: 2011).*
Pharmaceuticals, 2010, 3, 3212-3239 (Year: 2010).*
Abel et al., "Oxaazamacrocycles incorporating the quinoline moiety: synthesis and the study of their binding properties towards metal cations", New Journal of Chemistry, vol. 40, 2016, pp. 5818-5828.
Amaravadi et al., "Autophagy inhibition enhances therapy-induced apoptosis in a Myc-induced model of lymphoma", J. Clin. Invest., 2007, 117(2), 326-336.
Amaravadi et al., "Principles and Current Strategies for Targeting Autophagy for Cancer Treatment", Clin. Cancer Res., 2011, 17(4), 654-666.
Amaravadi et al., "The Roles of therapy-induced autophagy and necrosis in cancer treatment", Clin. Cancer Res., 2007, 13(24), 7271-7279.
Amaravadi, Autophagy-induced tumor dormancy in ovarian cancer, J. Clin. Invest., 2008.
Burnett et al., "Novel small molecule inhibitors of botulinum neurotoxin A metalloprotease activity", Biochem. Biophys. Res. Commun., 2003, 310(1), 84-93.
Cadwell et al., "A Key role for autophagy and the autophagy gene Atg16l1 in mouse and human intestinal Paneth cells", Nature, 2008, 456(7219), 249-263.
Carew et al., "Targeting autophagy augments the anticancer activity of the histone deacetylase inhibitor SAHA to overcome Ber-Abl-mediated drug resistance", Blood, 2007.
Degenhardt et al., "Autophagy promotes tumor cell survival and restricts necrosis, inflammation and tumorigenesis", Cancer Cell, 2006, 10(1), 51-64.
Degtyarev et al., "Akt inhibition promotes autophagy and sensitizes PTEN-null tumors to lysosomotropic agents", J. Cell Biol., 2008, 183(1), 101-116.
Girault et al., "Antiplasmodial activity and cytotoxicity of bis-, tris-, and tetraquinolines with linear or cyclic amino linkers", J. Med. Chem., 2001, 44(11), 1658-1665.
Hay, M.P., "DNA-Targeted 1,2,4-Benzotriazine 1,4-Dioxides:? Potent Analogues of the Hypoxia-Selective Cytotoxin Tirapazamine," J. Med. Chem. 2004, vol. 47, No. 2, pp. 475-488.
Hirokazu M., et al, "Synthesis of Monoaza Crown Ethers from N,N-Di[oligo(oxyalkylene)]amines and Oligoethylene Glycol Di(p-toluenesulfonates) or Corresponding Dichlorides," Bull. Chem. Soc. Japan, vol. 56,1983, pp. 212-218.

(Continued)

Primary Examiner — Noble E Jarrell
Assistant Examiner — Phillip Matthew Rzeczycki
(74) Attorney, Agent, or Firm — BakerHostetler

(57) ABSTRACT

The disclosure is directed to bisaminoquinolines and bisaminoacridines as autophagy inhibitors for treating cancer and other disease states and conditions.

24 Claims, 2 Drawing Sheets

(56) References Cited

OTHER PUBLICATIONS

Hu et al., "A 4-aminoquinoline derivate that markedly sensitizers tumor cell killing by Akt inhibitors with a minimum cytotoxicity to non-cancer cells," Eur. J. Med. Chem., 2010, 45(2), 705-709.

Lum et al., "Autophagy in Metazoans: Cell Survival in the Land of Plenty", Nat. Rev. Mol. Cell Bio., 2005, 6(6), 439-448.

Mahalingam et al., "Combined autophagy and HDAC inhibition: A phase I safety, tolerability, pharmacokinetic, and pharmacodynamic analysis of hydroxychloroquine in combination with the HDAC inhibitor vorinostat in patients with advanced solid tumors", Autophagy, 2014, 10(8).

McAfee et al., "Autophagy inhibitor Lys05 has single-agent anti-tumor activity and reproduces the phenotype of a genetic autophagy deficiency", Proc. Natl. Acad. Sci., U.S.A., 2012, 109(21), 8253-8258.

O'Driscoll, "Reversible thermal switching of aqueous dispersibility of multiwalled carbon nanotubes", Chemistry—A Eur. J., 2015, 21(10), 3891-3894.

Pubchem, "N'-[2-[(6-Chloro-2-methoxyacridin-9-yl)amino]ethyl]-N-[2-[2-[(6-chloro-2-methoxyacridin-9-yl)amino]ethylamino]ethyl]ethane-1,2-diamine", Aug. 8, 2005, 9 pages.

Rangwala et al., "Combined MTOR and autophagy inhibition: Phase I trail of hydroxychloroquine and temsiolimus in patients with advanced solid tumors and melanoma", Autophagy, 2014, 10(8).

Rebecca et al., "Inhibition of autophagy enhances the effects of the AKT inhibitor MK-2206 when combined with paclitaxel and carboplatin in BRAF wild-type Melanoma", Pigment Cell Melanoma Res., 2014, 27(3), 465-478.

Rosenfeld et al., "A Phase I/II trial of hydroxychloroquine in conjunction with radiation therapy and concurrent and adjuvant temozolomide in patients with newly diagnosed glioblastoma multiforme", Autophagy, 2014, 10(8).

Shrivastava et al., "Designer peptides: learning from nature", Urr Pharm. Des., 2009, 15(6), 675-681.

Solomon et al., "Design and synthesis of chloroquine analogs with anti-breast cancer property", Eur. J. Med. Chem., 2010, 45(9), 3916-3923.

Tanida et al., "LC3 conjugation system in mammalian autophagy", Int. J. Biochem. Cell Biol., 2004, 36(12), 2503-2518.

Vance et al., "Polyvalency: A promising strategy for drug design", Biotechnol. Bioeng., 2008, 101(3), 429-434.

Vennerstrom J, et al. Bisquinolines. 2. Antimalarial N, N-Bis(7-chloro-quinolin-4-yl) heteroalkanediamines. Antimalarial Bisquinolines, 1998;41:4360-4364.

Wang., K., et al., "A New Family of Thermo-, pH-, and $CO_2$-Responsive Homopolymers of Poly[Oligo(ethylene glycol) (N-dialkylamino) methacrylate]s," Macromolecules, 2017, vol. 50, No. 12, pp. 4686-4698.

Yoshino, A., et al., "Construction of a mixed valence trinuclear MnIIMnIIIMnII aggregate into a large macrocyclic ligandElectronic supplementary information (ESI) available: synthetic route to diamine (daud) and 1H NMR data for all products obtained at each step. See http://www.rsc.org/suppdata/cc/b0/b003479g," Chem. Commun., 2000, pp. 1475-1476.

Young P.R, et al., "Frameshift mutagenesis of 9-aminoacridine derivatives in Salmonella typhimurium", Mutation Research/Genetic Toxicology, vol. 90, No. 1, Sep. 1981, pp. 1-10.

* cited by examiner

BISAMINOQUINOLINES AND BISAMINOACRIDINES COMPOUNDS AND METHODS OF THEIR USE

CROSS REFERENCE TO RELATED APPLICATIONS

This application is the National Phase Application of International Patent Application No. PCT/US2020/034446, filed May 24, 2020, which claims the benefit of U.S. Provisional Application No. 62/852,693, filed May 24, 2019, the entireties of which are incorporated herein by reference.

GOVERNMENT RIGHTS

This invention was made with government support under CA114046 awarded by the National Institutes of Health. The government has certain rights in the invention.

TECHNICAL FIELD

The disclosure is directed to bisaminoquinolines and bisaminoacridines as autophagy inhibitors for treating cancer and other disease states and conditions.

BACKGROUND

Autophagy consists of the sequestration of organelles and proteins in autophagic vesicles (AV) and degradation of this cargo through lysosomal fusion. Autophagy allows tumor cells to survive metabolic and therapeutic stresses. Multiple publications indicate therapy-induced autophagy is a key resistance mechanism to many anti-cancer agents. A number of autophagic processes occur in nature, all of which have the degradation of intracellular components via the lysosome as a common feature. A well-known mechanism of autophagy involves the formation of a membrane around a targeted region of a cell, separating the contents from the rest of the cytoplasm. The resultant vesicle then fuses with a lysosome which subsequently degrades the contents.

Autophagy inhibitors for treating cancer and other conditions have been previously described. See, e.g., WO2016168721, WO2016022956, and WO2012149186. More authophagy inhibitors are needed.

SUMMARY

The disclosure is directed to compounds of formulas I, II, and III, as well as the pharmaceutically acceptable salts thereof:

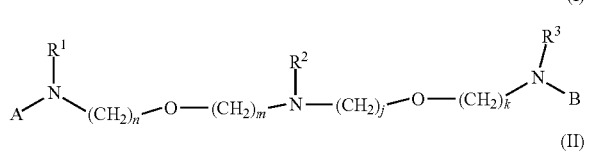
(I)

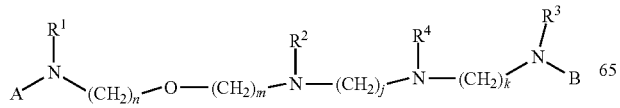
(II)

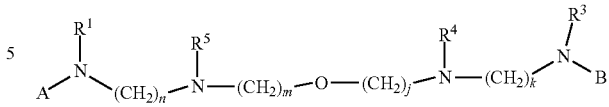
(II)

wherein
A is

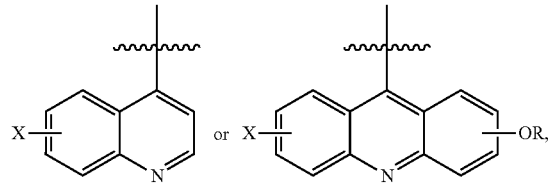

wherein X is F, Cl, or Br and R is H, $C_{1-6}$alkyl, or —C(O)$C_{1-6}$alkyl;

B is

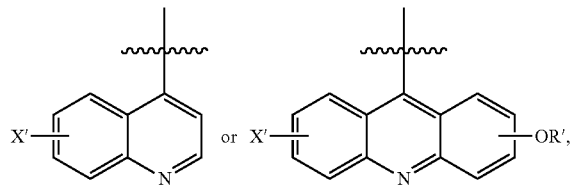

wherein X' is F, Cl, or Br and R' is H, $C_{1-6}$alkyl, or —C(O)$C_{1-6}$alkyl;

$R^1$ is H, $C_{1-6}$alkyl, —C(O)$C_{1-6}$alkyl, alkaryl, or alkheteroaryl; $R^2$ is H, $C_{1-6}$alkyl, —C(O)$C_{1-6}$alkyl, alkaryl, or alkheteroaryl; $R^3$ is H, $C_{1-6}$alkyl, —C(O)$C_{1-6}$alkyl, alkaryl, or alkheteroaryl; $R^4$ is H, $C_{1-6}$alkyl, —C(O)$C_{1-6}$alkyl, alkaryl, or alkheteroaryl; $R^5$ is H, $C_{1-6}$alkyl, —C(O)$C_{1-6}$alkyl, alkaryl, or alkheteroaryl; $R^6$ is H, $C_{1-6}$alkyl, —C(O)$C_{1-6}$alkyl, alkaryl, or alkheteroalkyl; n is 1, 2, 3, 4, or 5; m is 1, 2, 3, 4, or 5; j is 1, 2, 3, 4, or 5; and k is 1, 2, 3, 4, or 5.

Pharmaceutical compositions comprising the compounds of formulas I, II, and III are described. Methods of using the compounds of the disclosure in the treatment of, for example, cancer, are also described.

DETAILED DESCRIPTION OF ILLUSTRATIVE EMBODIMENTS

Figure 1A:
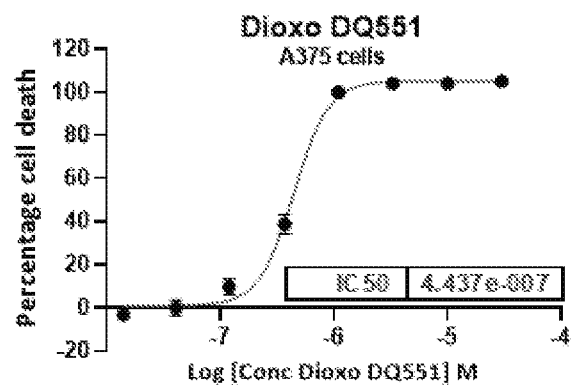
FIG. 1A depicts percentage cell death of A375 cells using an exemplary embodiment of the disclosure, dioxoDQ551.

Unless otherwise defined, all technical and scientific terms used herein have the same meaning as commonly understood by one of ordinary skill in the art to which this disclosure pertains. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (e.g., to at least one) of the grammatical object of the article unless the context clearly indicates otherwise. By way of example, "an element" means one element or more than one element.

The term "compound," as used herein, unless otherwise indicated, refers to any general or specific chemical compounds disclosed herein, as well as pharmaceutically acceptable salts and/or deuterated forms thereof where applicable, in context. Deuterated small molecules contemplated are those in which one or more of the hydrogen atoms contained in the drug molecule have been replaced by deuterium.

As used herein, the term "alkyl," refers to a straight or branched chain hydrocarbon radical having up to twelve carbon atoms. In some embodiments, the number of carbon atoms is designated (i.e., $C_{1-6}$ means one to six carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. Alkyl groups may be optionally substituted as provided herein. In some embodiments, the alkyl group is a $C_{1-6}$ alkyl; in some embodiments, it is a $C_1$-$C_4$ alkyl.

When a range of carbon atoms is used herein, for example, $C_{1-6}$, all ranges, as well as individual numbers of carbon atoms are encompassed. For example, "$C_{1-3}$" includes $C_{1-3}$, $C_1$-$C_2$, $C_{2-3}$, $C_1$, $C_2$, and $C_3$.

The term "alk," when used in combination with "aryl" or "heteroaryl," for example, "alkaryl" or "alkheteroaryl," refers to a straight or branched chain hydrocarbon diradical having up to twelve carbon atoms. Examples of alk groups include —$CH_2$—, —$CH_2$—$CH_2$—, —$CH_2$—$CH_2$—$CH_2$—, and the like.

The term "aryl," when used alone or in combination with "alk," refers to a single, all carbon aromatic ring or a multiple condensed all carbon ring system wherein at least one of the rings is aromatic. For example, in certain embodiments, an aryl group has 6 to 12 carbon atoms. Aryl includes a phenyl radical. Aryl also includes multiple condensed ring systems (e.g., ring systems comprising 2, 3 or 4 rings) having about 9 to 12 carbon atoms in which at least one ring is aromatic and wherein the other rings may be aromatic or not aromatic. It is to be understood that the point of attachment of a multiple condensed ring system, as defined above, can be at any position of the aromatic ring. Non-limiting examples of aryl groups include, but are not limited to, phenyl, indenyl, naphthyl, 1, 2, 3,4-tetrahydronaphthyl, and the like.

The term "heteroaryl," when used alone or in combination with "alk," refers to a single aromatic ring that has at least one atom other than carbon in the ring, wherein the atoms are selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. A heteroaryl (a single aromatic ring or multiple condensed ring system) can also have about 5 to 12 or about 5 to 10 members within the heteroaryl ring. Multiple condensed ring systems may be optionally substituted with one or more (e.g., 1, 2, 3 or 4) oxo groups on the carbocycle or heterocycle portions of the condensed ring. The rings of a multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the heteroaryl ring. It is also to be understood that the point of attachment for a heteroaryl or heteroaryl multiple condensed ring system can be at any suitable atom of the heteroaryl ring including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole. In one embodiment the term "heteroaryl" refers to a single aromatic ring containing at least one heteroatom. For example, the term includes 5-membered and 6-membered monocyclic aromatic rings that include one or more heteroatoms. Non-limiting examples of heteroaryl include but are not limited to pyridyl, furyl, thiazole, pyrimidine, oxazole, and thiadiazole.

The term "patient" or "subject" is used throughout the specification within context to describe an animal, generally a mammal, especially including a domesticated animal and preferably a human, to whom treatment, including prophylactic treatment (prophylaxis), with the compounds or compositions according to the present disclosure is provided. For treatment of those conditions or disease states which are specific for a specific animal such as a human patient, the term patient refers to that specific animal. In most instances, the patient or subject of the present invention is a human patient of either or both genders.

The term "effective" is used to describe an amount of a compound or composition, when used within the context of its intended use, effects an intended result, whether that result relates to the prophylaxis and/or therapy of a condition or disease state or as otherwise described herein. The term effective subsumes all other effective amount or effective concentration terms, which are otherwise described or used in the present application.

The term "inhibit" as used herein refers to the partial or complete elimination of a potential effect, while inhibitors are compounds that have the ability to inhibit.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

"Treating" or "treatment" of any disease or disorder refers, in one embodiment, to ameliorating the disease or disorder (e.g., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder. Treatment, as used herein, encompasses both prophylactic and therapeutic treatment, principally of cancer. Compounds according to the present invention can, for example, be administered prophylactically to a mammal in advance of the occurrence of disease to reduce the likelihood of that disease. Prophylactic administration is effective to reduce or decrease the likelihood of the subsequent occurrence of disease in the mammal, or decrease the severity of disease that subsequently occurs, especially including metastasis of cancer. Alternatively, compounds according to the present invention can, for example, be administered therapeutically to a mammal that is already afflicted by disease. In one embodiment of therapeutic administration, administration of the present compounds is effective to eliminate the disease and produce a remission or substantially eliminate the likelihood of metastasis of a cancer. Administration of the compounds according to the present invention is effective to decrease the severity of the disease or lengthen the lifespan of the mammal so afflicted, in the case of cancer or other disease or condition described herein.

The term "prevention" when used in context shall mean "reducing the likelihood" or preventing a disease, condition or disease state from occurring as a consequence of administration or concurrent administration of one or more compounds or compositions according to the present invention, alone or in combination with another agent. It is noted that prophylaxis will rarely be 100% effective; consequently the terms prevention and reducing the likelihood are used to denote the fact that within a given population of patients or subjects, administration with compounds according to the present invention will reduce the likelihood or inhibit a particular condition or disease state (in particular, the worsening of a disease state such as the growth or metastasis of cancer) or other accepted indicators of disease progression from occurring.

The term "autophagy" or "autophagocytosis" is used to describe a catabolic process in cells which involves the degradation of a cell's own components through lysosomes. Autophagy is a highly regulated process of biological systems that plays a normal part in cell growth development and homeostasis. helping to maintain a balance between the synthesis, degradation, and subsequent recycling of cellular products. It is a major mechanism by which a cell allocates nutrients from unnecessary processes to more-essential processes.

An "autophagy-related disorder" includes diseases, disease states and/or conditions which benefit from the inhibition of autophagy, including, but not limited to, cancer (including the metastasis of cancer), rheumatoid arthritis, malaria, antiphospholipid antibody syndrome, lupus, chronic urticaria and Sjogren's disease.

The term "radiotherapy" or "radiation therapy" is used to describe therapy for cancer which may be used in conjunction with the present compounds. Radiation therapy uses high doses of radiation, such as X-rays, or other energy sources such as radioisotopes (gamma, beta or alpha emitters), to destroy cancer cells. The radiation damages the genetic material of the cells so that they can't grow. Although radiation damages normal cells as well as cancer cells, the normal cells can repair themselves and function, while the cancer cells cannot.

Radiation therapy may be used in combination with the presently described compounds, alone or in combination with additional anticancer compounds as otherwise disclosed herein, depending on the cancer to be treated. Radiotherapy therapy is most effective in treating cancers that have not spread outside the area of the original cancer, but it also may be used if the cancer has spread to nearby tissue. Radiotherapy is sometimes used after surgery to destroy any remaining cancer cells and to relieve pain from metastatic cancer.

The disclosure is directed to compounds of formulas I, II, and III, as well as the pharmaceutically acceptable salts of the compounds of formula I, II, and III.

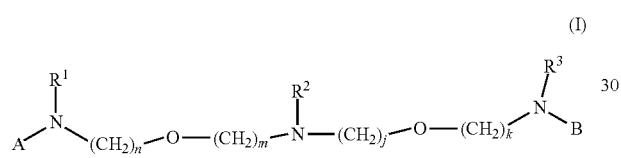

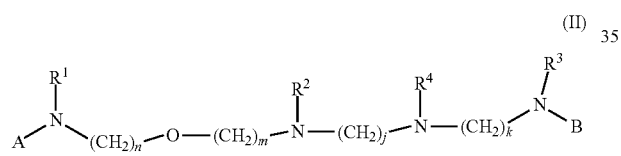

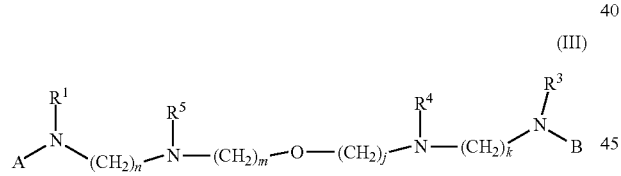

In some aspects, the compounds are compounds of formula I, or a pharmaceutically acceptable salt thereof. In some aspects, the compounds are compounds of formula II, or a pharmaceutically acceptable salt thereof. In some aspects, the compounds are compounds of formula III, or a pharmaceutically acceptable salt thereof.

According to the disclosure, for any compound of formula I, II, or III, A is

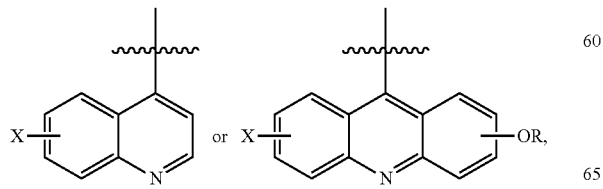

wherein X is F, Cl, or Br and H is H, $C_{1-6}$alkyl, or $-C(O)C_{1-6}$alkyl. In some aspects, A is

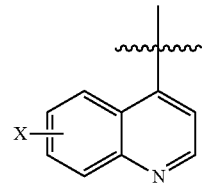

and X is F. In some aspects, A is

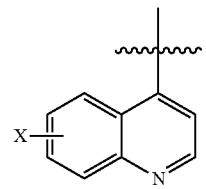

and X is Cl. In some aspects, A is

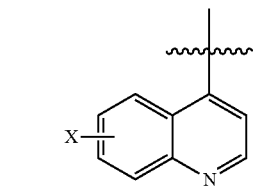

and X is Br. In some aspects, A is

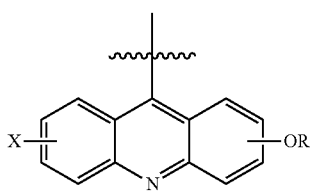

and X is F and R is H. In some aspects, A is

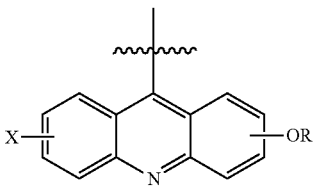

and X is F and R is $C_{1-6}$alkyl, for example, methyl, ethyl, propyl, isopropyl, butyl, or t-butyl. In some aspects, A is

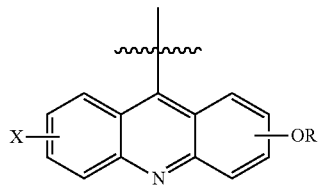

and X is F and R is —C(O)$C_{1-6}$alkyl, for example, —C(O)Me, —C(O)Et, —C(O)Pr, —C(O)Bu, or —C(O)tBu. In some aspects, A is

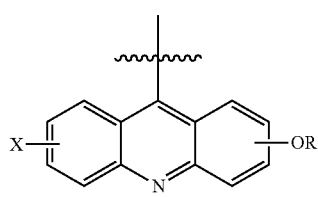

and X is Cl and R is $C_{1-6}$alkyl, for example, methyl, ethyl, propyl, isopropyl, butyl, or t-butyl. In some aspects, A is

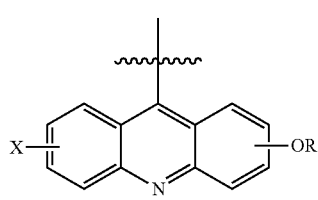

and X is Br and R is —C(O)$C_{1-6}$alkyl, for example, —C(O)Me, —C(O)Et, —C(O)Pr, —C(O)Bu, or —C(O)tBu.

According to the disclosure, for any compound of formula I, II, or III, B is

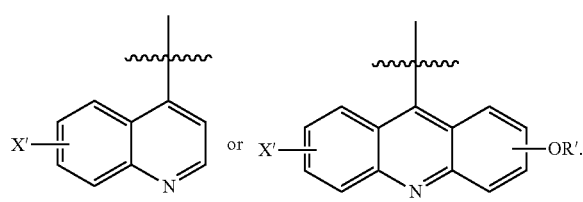

wherein X' is F, Cl, or Br and R' is H, $C_{1-6}$alkyl, or —C(O)$C_{1-6}$alkyl. In some aspects, B is

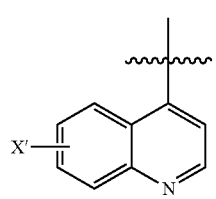

and X' is F. In some aspects, B is

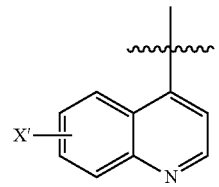

and X' is Cl. In some aspects, B is

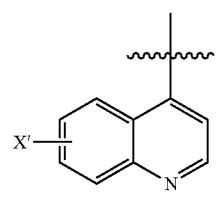

and X' is Br. In some aspects, B is

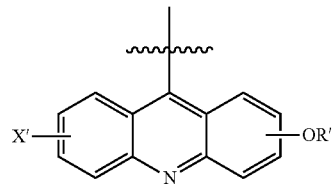

and X' is F and $R^1$ is H. In some aspects, B is

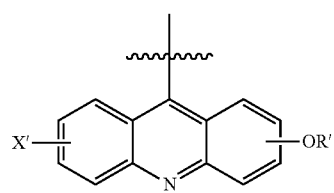

and X' is F and R' is $C_{1-6}$alkyl, for example, methyl, ethyl, propyl, isopropyl, butyl, or t-butyl. In some aspects, B is

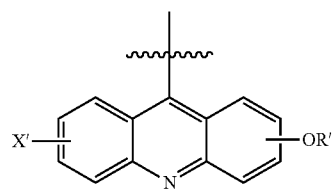

and X' is F and R' is —C(O)$C_{1-6}$alkyl, for example, —C(O)Me, —C(O)Et, —C(O)Pr, —C(O)Bu, or —C(O)tBu.

In some aspects, B is

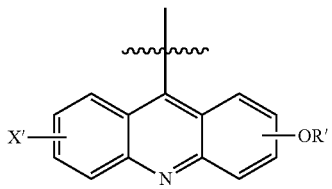

and X' is Cl and R' is $C_{1-6}$alkyl, for example, methyl, ethyl, propyl, isopropyl, butyl, or t-butyl. In some aspects, B is

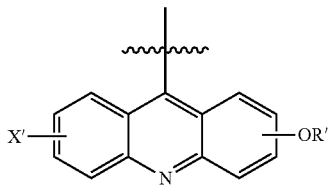

and X' is Br and R' is —C(O)$C_{1-6}$alkyl, for example, —C(O)Me, —C(O)Et, —C(O)Pr, —C(O)Bu, or —C(O)tBu.

In some aspects, the compound is a compound of formula I and A is

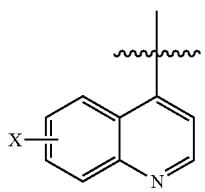

and B is

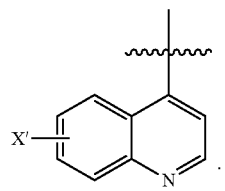

In these embodiments, X is F and X' is F; or X is Cl and X' is Cl; or X is Br and X' is Br; or X is F and X' is Cl; or X is F and X' is Br; or X is Cl and X' is Br.

In some aspects, the compound is a compound of formula I and A is

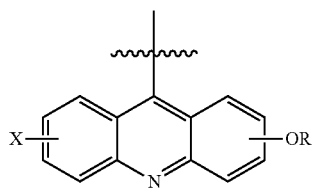

and B is

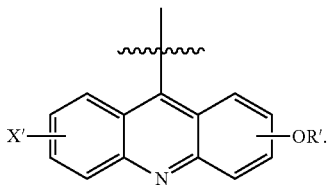

In these embodiments, X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, Bu); or R is H and R' is —C(O)$C_{1-6}$alkyl (e.g., —C(O)Me, —C(O)Et, —C(O)Pr, —C(O)Bu, or —C(O)tBu); or R is $C_{1-6}$alkyl (e.g., Me, Et, Pr, Bu) and R' is $C_{1-6}$alkyl (e.g., Me, Et, Pr, Bu); or R is $C_{1-6}$alkyl (e.g., Me, Et, Pr, Bu) and R' is —C(O)$C_{1-6}$alkyl (e.g., —C(O)Me, —C(O)Et, —C(O)Pr, —C(O)Bu, or —C(O)tBu).

In some aspects the compound is a compound of formula I and A is

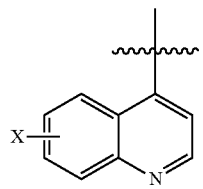

and B is

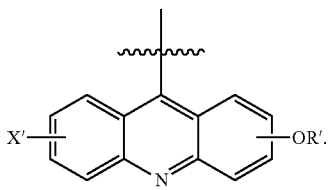

In some embodiments, R' is H and X is F and X' is F; or X is Cl and X' is Cl; or X is Br and X' is Br; or X is F and X' is Cl; or X is F and X' is Br; or X is Cl and X' is Br. In some embodiments, R' is $C_{1-6}$alkyl (e.g., Me, Et, Pr, Bu) and X is F and X' is F; or X is Cl and X' is Cl; or X is Br and X' is Br; or X is F and X' is Cl; or X is F and X' is Br; or X is Cl and X' is Br. In some aspects, R' is —C(O)$C_{1-6}$alkyl (e.g., —C(O)Me, —C(O)Et, —C(O)Pr, —C(O)Bu, or —C(O)tBu) and X is F and X' is F; or X is Cl and X' is Cl; or X is Br and X' is Br; or X is F and X' is Cl; or X is F and X' is Br; or X is Cl and X' is Br.

In some aspects, the compound is a compound of formula II and A is

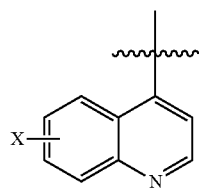

and B is

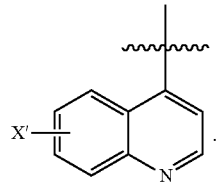

In these embodiments, X is F and X' is F; or X is Cl and X' is Cl; or X is Br and X' is Br; or X is F and X' is Cl; or X is F and X' is Br; or X is Cl and X' is Br.

In some aspects, the compound is a compound of formula II and A is

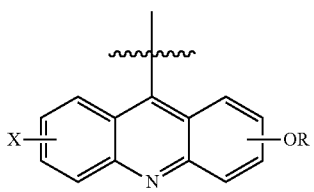

and B is

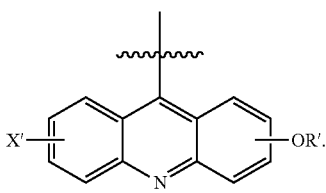

In these embodiments, X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, Bu); or R is H and R' is —C(O)$C_{1-6}$alkyl (e.g., —C(O)Me, —C(O)Et, —C(O)Pr, —C(O)Bu, or —C(O)tBu); or R is $C_{1-6}$alkyl (e.g., Me, Et, Pr, Bu) and R' is $C_{1-6}$alkyl (e.g., Me, Et, Pr, Bu); or R is $C_{1-6}$alkyl (e.g., Me, Et, Pr, Bu) and R' is —C(O)$C_{1-6}$alkyl (e.g., —C(O)Me, —C(O)Et, —C(O)Pr, —C(O)Bu, or —C(O)tBu).

In some aspects the compound is a compound of formula II and A is

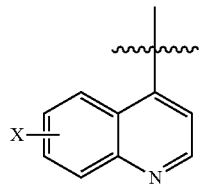

and B is

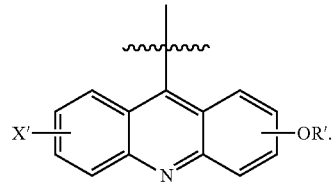

In some embodiments, R' is H and X is F and X' is F; or X is Cl and X' is Cl; or X is Br and X' is Br; or X is F and X' is Cl; or X is F and X' is Br; or X is Cl and X' is Br. In some embodiments, R' is $C_{1-6}$alkyl (e.g., Me, Et, Pr, Bu) and X is F and X' is F; or X is Cl and X' is Cl; or X is Br and X' is Br; or X is F and X' is Cl; or X is F and X' is Br; or X is Cl and X' is Br. In some aspects, R' is —C(O)$C_{1-6}$alkyl (e.g., —C(O)Me, —C(O)Et, —C(O)Pr, —C(O)Bu, or —C(O)tBu) and X is F and X' is F; or X is Cl and X' is Cl; or X is Br and X' is Br; or X is F and X' is Cl; or X is F and X' is Br; or X is Cl and X' is Br.

In some aspects, the compound is a compound of formula III and A is

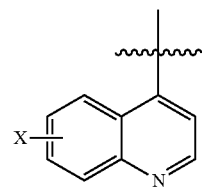

and B is

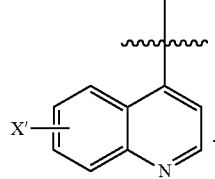

In these embodiments, X is F and X' is F; or X is Cl and X' is Cl; or X is Br and X' is Br; or X is F and X' is Cl; or X is F and X' is Br; or X is Cl and X' is Br.

In some aspects, the compound is a compound of formula III and A is

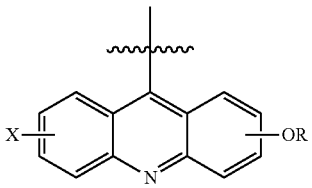

and B is

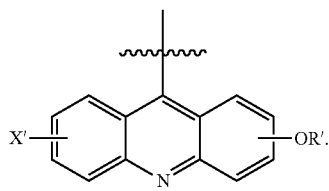

In these embodiments, X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, Bu); or R is H and R' is —C(O)$C_{1-6}$alkyl (e.g., —C(O)Me, —C(O)Et, —C(O)Pr, —C(O)Bu, or —C(O)tBu); or R is $C_{1-6}$alkyl (e.g., Me, Et, Pr, Bu) and R' is $C_{1-6}$alkyl (e.g., Me, Et, Pr, Bu); or R is $C_{1-6}$alkyl (e.g., Me, Et, Pr, Bu) and R' is —C(O)$C_{1-6}$alkyl (e.g., —C(O)Me, —C(O)Et, —C(O)Pr, —C(O)Bu, or —C(O)tBu).

In some aspects the compound is a compound of formula III and A is

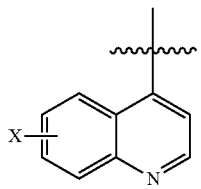

and B is

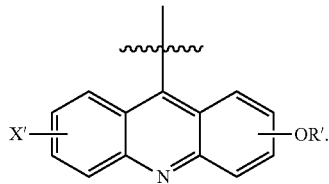

In some embodiments, R' is H and X is F and X' is F; or X is Cl and X' is Cl; or X is Br and X' is Br; or X is F and X' is Cl; or X is F and X' is Br; or X is Cl and X' is Br. In some embodiments, R' is $C_{1-6}$alkyl (e.g., Me, Et, Pr, Bu) and X is F and X' is F; or X is Cl and X' is Cl; or X is Br and X' is Br; or X is F and X' is Cl; or X is F and X' is Br; or X is Cl and X' is Br. In some aspects, R' is —C(O)$C_{1-6}$alkyl (e.g., —C(O)Me, —C(O)Et, —C(O)Pr, —C(O)Bu, or —C(O)tBu) and X is F and X' is F; or X is Cl and X' is Cl; or X is Br and X' is Br; or X is F and X' is Cl; or X is F and X' is Br; or X is Cl and X' is Br.

According to the disclosure $R^1$ of any compound of formula I, II, and III is H, $C_{1-6}$alkyl, —C(O)$C_{1-6}$alkyl, alkaryl, or alkheteroaryl. In some aspects, $R^1$ is H. In some aspects, $R^1$ is $C_{1-6}$alkyl (e.g., Me, Et, Pr, Bu). In some aspects, $R^1$ is —C(O)$C_{1-6}$alkyl (e.g., —C(O)Me, —C(O)Et, —C(O)Pr, —C(O)Bu, or —C(O)tBu). In some aspects, $R^1$ is alkaryl (e.g., —CH$_2$-phenyl or —CH$_2$-napthyl). In some aspects, $R^1$ is alkheteroaryl (e.g., —CH$_2$-pyridyl or —CH$_2$-pyrazinyl).

According to the disclosure $R^2$ of any compound of formula I, II, and III is H, $C_{1-6}$alkyl, —C(O)$C_{1-6}$alkyl, alkaryl, or alkheteroaryl. In some aspects, $R^2$ is H. In some aspects, $R^2$ is $C_{1-6}$alkyl (e.g., Me, Et, Pr, Bu). In some aspects, $R^2$ is —C(O)$C_{1-6}$alkyl (e.g., —C(O)Me, —C(O)Et, —C(O)Pr, —C(O)Bu, or —C(O)tBu). In some aspects, $R^2$ is alkaryl (e.g., —CH$_2$-phenyl or —CH$_2$-napthyl). In some aspects, $R^2$ is alkheteroaryl (e.g., —CH$_2$-pyridyl or —CH$_2$-pyrazinyl).

According to the disclosure $R^3$ of any compound of formula I, II, and III is H, $C_{1-6}$alkyl, —C(O)$C_{1-6}$alkyl, alkaryl, or alkheteroaryl. In some aspects, $R^3$ is H. In some aspects, $R^3$ is $C_{1-6}$alkyl (e.g., Me, Et, Pr, Bu). In some aspects, $R^3$ is —C(O)$C_{1-6}$alkyl (e.g., —C(O)Me, —C(O)Et, —C(O)Pr, —C(O)Bu, or —C(O)tBu). In some aspects, $R^3$ is alkaryl (e.g., —CH$_2$-phenyl or —CH$_2$-napthyl). In some aspects, $R^3$ is alkheteroaryl (e.g., —CH$_2$-pyridyl or —CH$_2$-pyrazinyl).

According to the disclosure $R^4$ of any compound of formula I, II, and III is H, $C_{1-6}$alkyl, —C(O)$C_{1-6}$alkyl, alkaryl, or alkheteroaryl. In some aspects, $R^4$ is H. In some aspects, $R^4$ is $C_{1-6}$alkyl (e.g., Me, Et, Pr, Bu). In some aspects, $R^4$ is —C(O)$C_{1-6}$alkyl (e.g., —C(O)Me, —C(O)Et, —C(O)Pr, —C(O)Bu, or —C(O)tBu). In some aspects, $R^4$ is alkaryl (e.g., —CH$_2$-phenyl or —CH$_2$-napthyl). In some aspects, $R^4$ is alkheteroaryl (e.g., —CH$_2$-pyridyl or —CH$_2$-pyrazinyl).

According to the disclosure $R^5$ of any compound of formula I, II, and III is H, $C_{1-6}$alkyl, —C(O)$C_{1-6}$alkyl, alkaryl, or alkheteroaryl. In some aspects, $R^5$ is H. In some aspects, $R^5$ is $C_{1-6}$alkyl (e.g., Me, Et, Pr, Bu). In some aspects, $R^5$ is —C(O)$C_{1-6}$alkyl (e.g., —C(O)Me, —C(O)Et, —C(O)Pr, —C(O)Bu, or —C(O)tBu). In some aspects, $R^5$ is alkaryl (e.g., —CH$_2$-phenyl or —CH$_2$-napthyl). In some aspects, $R^5$ is alkheteroaryl (e.g., —CH$_2$-pyridyl or —CH$_2$-pyrazinyl).

According to the disclosure $R^6$ of any compound of formula I, II, and III is H, $C_{1-6}$alkyl, —C(O)$C_{1-6}$alkyl, alkaryl, or alkheteroaryl. In some aspects, $R^6$ is H. In some aspects, $R^6$ is $C_{1-6}$alkyl (e.g., Me, Et, Pr, Bu). In some aspects, $R^6$ is —C(O)$C_{1-6}$alkyl (e.g., —C(O)Me, —C(O)Et, —C(O)Pr, —C(O)Bu, or —C(O)tBu). In some aspects, $R^6$ is alkaryl (e.g., —CH$_2$-phenyl or —CH$_2$-napthyl). In some aspects, $R^6$ is alkheteroaryl (e.g., —CH$_2$-pyridyl or —CH$_2$-pyrazinyl).

In some aspects, the compound is a compound of formula IIIA and. In some aspects, the compound is a compound of formula IIIAa and. In some aspects, the compound is a compound of formula IIIB and. In some aspects, the compound is a compound of formula IIIBb and. In some aspects, the compound is a compound of formula IIIC and. In some aspects, the compound is a compound of formula IIICc and.

In some aspects of the compounds of formulas I, II and III, n is 1. In some aspects, n is 2. In some aspects, n is 3. In some aspects, n is 4. In some aspects, n is 5.

In some aspects of the compounds of formulas I, II and III, m is 1. In some aspects, m is 2. In some aspects, m is 3. In some aspects, m is 4. In some aspects, m is 5.

In some aspects of the compounds of formulas I, II and III, j is 1. In some aspects, j is 2. In some aspects, j is 3. In some aspects, j is 4. In some aspects, j is 5.

In some aspects of the compounds of formulas I, II and III, k is 1. In some aspects, k is 2. In some aspects, k is 3. In some aspects, k is 4. In some aspects, k is 5.

In some aspects of the compounds of formula I, II, and III, n is 1, m is 1, j is 1, and k is 1. In some aspects of the compounds of formula I, II, and III, n is 2, m is 2, j is 2, and k is 2. In some aspects of the compounds of formula I, II, and III, n is 3, m is 3, j is 3, and k is 3. In some aspects of the compounds of formula I, II, and III, n is 4, m is 4, j is 4, and k is 4. In some aspects of the compounds of formula I, II, and III, n is 5, m is 5, j is 5, and k is 5.

In some aspects of the compounds of formula I, II, and III, n is 2, m is 1, j is 1, and k is 1. In some aspects of the compounds of formula I, II, and III, n is 3, m is 1, j is 1, and k is 1. In some aspects of the compounds of formula I, II, and III, n is 4, m is 1, j is 1, and k is 1. In some aspects of the compounds of formula I, II, and III, n is 5, m is 1, j is 1, and k is 1.

In some aspects of the compounds of formula I, II, and III, n is 1, m is 2, j is 1, and k is 1. In some aspects of the compounds of formula I, II, and III, n is 1, m is 3, j is 1, and k is 1. In some aspects of the compounds of formula I, II, and III, n is 1, m is 4, j is 1, and k is 1. In some aspects of the compounds of formula I, II, and III, n is 1, m is 5, j is 1, and k is 1.

In some aspects of the compounds of formula I, II, and III, n is 1, m is 1, j is 2, and k is 1. In some aspects of the compounds of formula I, II, and III, n is 1, m is 1, j is 3, and k is 1. In some aspects of the compounds of formula I, II, and III, n is 1, m is 1, j is 4, and k is 1. In some aspects of the compounds of formula I, II, and III, n is 1, m is 1, j is 5, and k is 1.

In some aspects of the compounds of formula I, II, and III, n is 1, m is 1, j is 1, and k is 2. In some aspects of the compounds of formula I, II, and III, n is 1, m is 1, j is 1, and k is 3. In some aspects of the compounds of formula I, II, and III, n is 1, m is 1, j is 1, and k is 4. In some aspects of the compounds of formula I, II, and III, n is 1, m is 1, j is 1, and k is 5.

In some aspects of the compounds of formula I, II, and III, n is 2, m is 2, j is 1, and k is 1. In some aspects of the compounds of formula I, II, and III, n is 1, m is 2, j is 2, and k is 1. In some aspects of the compounds of formula I, II, and III, n is 2, m is 1, j is 1, and k is 2.

In some aspects of the compounds of formula I, II, and III, n is 3, m is 3, j is 1, and k is 1. In some aspects of the compounds of formula I, II, and III, n is 1, m is 3, j is 3, and k is 1. In some aspects of the compounds of formula I, II, and III, n is 3, m is 1, j is 1, and k is 3.

In some aspects of the compounds of formula I, II, and III, n is 3, m is 3, j is 2, and k is 2. In some aspects of the compounds of formula I, II, and III, n is 2, m is 3, j is 3, and k is 2. In some aspects of the compounds of formula I, II, and III, n is 3, m is 2, j is 2, and k is 3.

In some aspects of the compounds of formula I, II, and III, n is 2, m is 1, j is 2, and k is 1. In some aspects of the compounds of formula I, II, and III, n is 2, m is 3, j is 2, and k is 3. In some aspects of the compounds of formula I, II, and III, n is 3, m is 2, j is 3, and k is 2.

In some aspects, the compound is a compound of formula I and $R^1$ is H, $R^2$ is $C_{1-6}$alkyl (e.g., Me, Et, Pr, Bu), and $R^3$ is H. In some aspects, the compound is a compound of formula II and $R^1$ is H, $R^2$ is $C_{1-6}$alkyl (e.g., Me, Et, Pr, Bu), $R^3$ is H, and $R^4$ is $C_{1-6}$alkyl (e.g., Me, Et, Pr, Bu). In some aspects, the compound is a compound of formula III and $R^1$ is H, $R^3$ is H, $R^5$ is $C_{1-6}$alkyl (e.g., Me, Et, Pr, Bu), and $R^6$ is $C_{1-6}$alkyl (e.g., Me, Et, Pr, Bu).

In some aspects, the compounds of formula I include

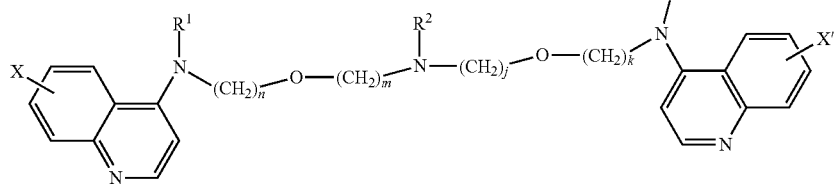

IA wherein X is F and X' is F; or X is Cl and X' is Cl; or X is Br and X' is Br; or X is F and X' is Cl; or X is F and X' is Br; or X is Cl and X' is Br; $R^1$ is H, $R^2$ is $C_{1-6}$alkyl (e.g., Me, Et, Pr, Bu), and $R^3$ is H; n is 1, 2, or 3; m is 1, 2, or 3; j is 1, 2, or 3; and k is 1, 2, or 3;

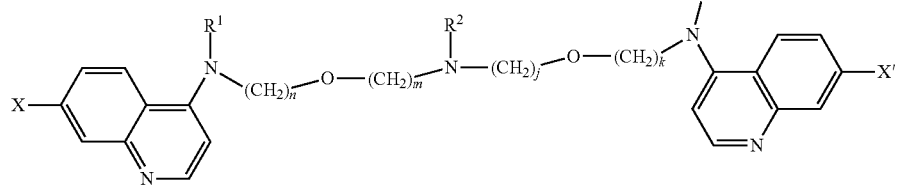

IAa wherein X is F and X' is F; or X is Cl and X' is Cl; or X is Br and X' is Br; or X is F and X' is Cl; or X is F and X' is Br; or X is Cl and X' is Br; $R^1$ is H, $R^2$ is $C_{1-6}$alkyl (e.g., Me, Et, Pr, Bu), and $R^3$ is H; n is 1, 2, or 3; m is 1, 2, or 3; j is 1, 2, or 3; and k is 1, 2, or 3;

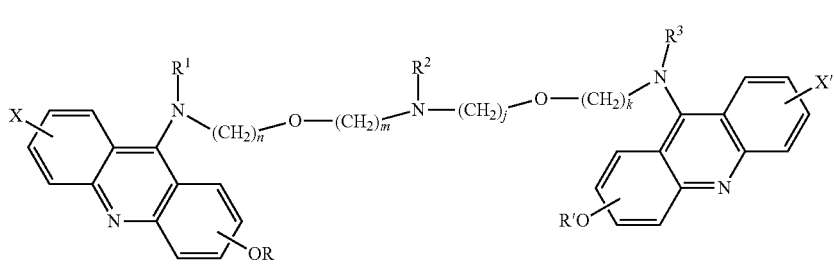

IB wherein X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, Bu); or R is H and R' is —C(O)$C_{1-6}$alkyl (e.g., —C(O)Me, —C(O)Et, —C(O)Pr, —C(O)Bu, or —C(O)tBu); or R is $C_{1-6}$alkyl (e.g., Me, Et, Pr, Bu) and R' is $C_{1-6}$alkyl (e.g., Me, Et, Pr, Bu); or R is $C_{1-6}$alkyl (e.g., Me, Et, Pr, Bu) and R' is —C(O)$C_{1-6}$alkyl (e.g., —C(O)Me, —C(O)Et, —C(O)Pr, —C(O)Bu, or —C(O)tBu); $R^1$ is H, $R^2$ is $C_{1-6}$alkyl (e.g., Me, Et, Pr, Bu), and $R^3$ is H; n is 1, 2, or 3; m is 1, 2, or 3; j is 1, 2, or 3; and k is 1, 2, or 3;

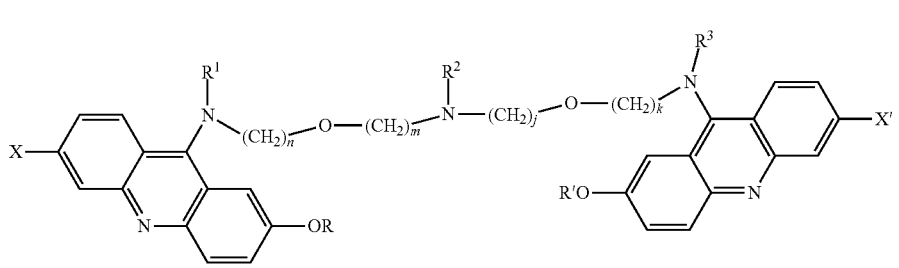

IBb wherein X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, Bu); or R is H and R' is —C(O)$C_{1-6}$alkyl (e.g., —C(O)Me, —C(O)Et, —C(O)Pr, —C(O)Bu, or —C(O)tBu); or R is $C_{1-6}$alkyl (e.g., Me, Et, Pr, Bu) and R' is $C_{1-6}$alkyl (e.g., Me, Et, Pr, Bu); or R is $C_{1-6}$alkyl (e.g., Me, Et, Pr, Bu) and R' is —C(O)$C_{1-6}$alkyl (e.g., —C(O)Me, —C(O)Et, —C(O)Pr, —C(O)Bu, or —C(O)tBu); $R^1$ is H, $R^2$ is $C_{1-6}$alkyl (e.g., Me, Et, Pr, Bu), and $R^3$ is H; n is 1, 2, or 3; m is 1, 2, or 3; j is 1, 2, or 3; and k is 1, 2, or 3;

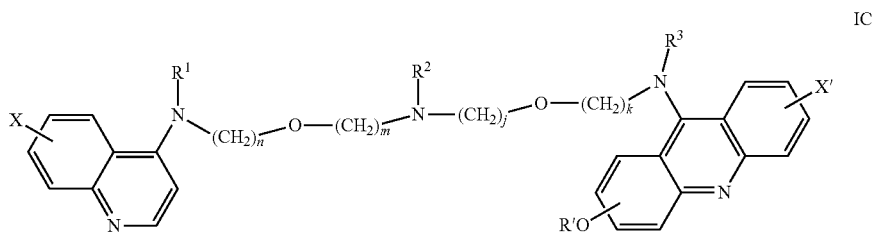

IC wherein R' is H and X is F and X' is F; or X is Cl and X' is Cl; or X is Br and X' is Br; or X is F and X' is Cl; or X is F and X' is Br; or X is Cl and X' is Br. In some embodiments, R' is $C_{1-6}$alkyl (e.g., Me, Et, Pr, Bu) and X is F and X' is F; or X is Cl and X' is Cl; or X is Br and X' is Br; or X is F and X' is Cl; or X is F and X' is Br; or X is Cl and X' is Br.

In some aspects, R' is —C(O)$C_{1-6}$alkyl (e.g., —C(O)Me, —C(O)Et, —C(O)Pr, —C(O)Bu, or —C(O)tBu) and X is F and X' is F; or X is Cl and X' is Cl; or X is Br and X' is Br; or X is F and X' is Cl; or X is F and X' is Br; or X is Cl and X' is Br; $R^1$ is H, $R^2$ is $C_{1-6}$alkyl (e.g., Me, Et, Pr, Bu), and $R^3$ is H; n is 1, 2, or 3; m is 1, 2, or 3; j is 1, 2, or 3; and k is 1, 2, or 3;

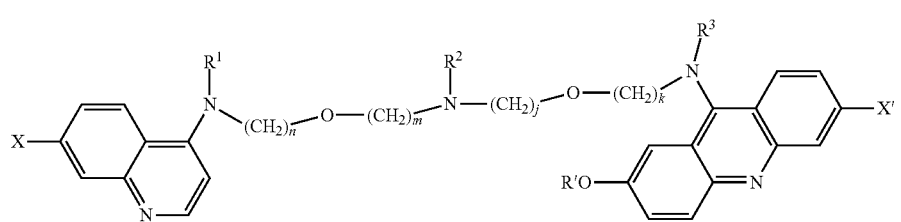

ICc

R' is H and X is F and X' is F; or X is Cl and X' is Cl; or X is Br and X' is Br; or X is F and X' is Cl; or X is F and X' is Br; or X is Cl and X' is Br. In some embodiments, R' is $C_{1-6}$alkyl (e.g., Me, Et, Pr, Bu) and X is F and X' is F; or X is Cl and X' is Cl; or X is Br and X' is Br; or X is F and X' is Cl; or X is F and X' is Br; or X is Cl and X' is Br. In some aspects, R' is —C(O)$C_{1-6}$alkyl (e.g., —C(O)Me, —C(O)Et, —C(O)Pr, —C(O)Bu, or —C(O)tBu) and X is F and X' is F; or X is Cl and X' is Cl; or X is Br and X' is Br; or X is F and X' is Cl; or X is F and X' is Br; or X is Cl and X' is Br; $R^1$ is H, $R^2$ is $C_{1-6}$alkyl (e.g., Me, Et, Pr, Bu), and $R^3$ is H; n is 1, 2, or 3; m is 1, 2, or 3; j is 1, 2, or 3; and k is 1, 2, or 3;

In some aspects, the compounds of formula II include

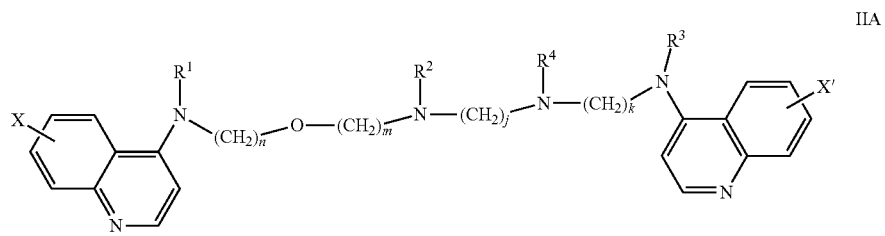

IIA wherein X is F and X' is F; or X is Cl and X' is Cl; or X is Br and X' is Br; or X is F and X' is Cl; or X is F and X' is Br; or X is Cl and X' is Br; $R^1$ is H, $R^2$ is $C_{1-6}$alkyl (e.g., Me, Et, Pr, Bu), $R^3$ is H, and $R^4$ is $C_{1-6}$alkyl (e.g., Me, Et, Pr, Bu); n is 1, 2, or 3; m is 1, 2, or 3; j is 1, 2, or 3; and k is 1, 2, or 3;

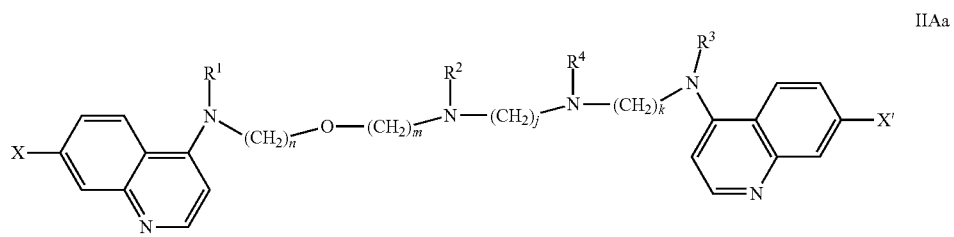

IIAa wherein X is F and X' is F; or X is Cl and X' is Cl; or X is Br and X' is Br; or X is F and X' is Cl; or X is F and X' is Br; or X is Cl and X' is Br; $R^1$ is H, $R^2$ is $C_{1-6}$alkyl (e.g., Me, Et, Pr, Bu), $R^3$ is H, and $R^4$ is $C_{1-6}$alkyl (e.g., Me, Et, Pr, Bu); n is 1, 2, or 3; m is 1, 2, or 3; j is 1, 2, or 3; and k is 1, 2, or 3;

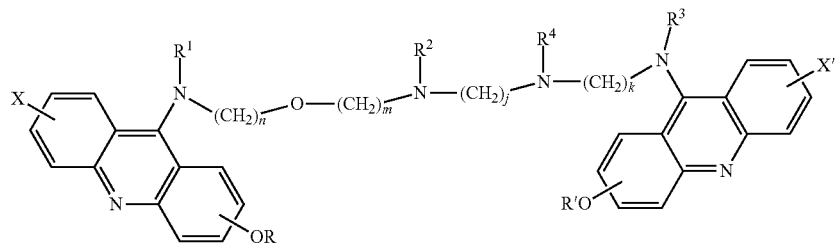

wherein X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, Bu); or R is H and R' is —C(O)$C_{1-6}$alkyl (e.g., —C(O)Me, —C(O)Et, —C(O)Pr, —C(O)Bu, or —C(O)tBu); or R is $C_{1-6}$alkyl (e.g., Me, Et, Pr, Bu) and R' is $C_{1-6}$alkyl (e.g., Me, Et, Pr, Bu); or R is $C_{1-6}$alkyl (e.g., Me, Et, Pr, Bu) and R' is —C(O)$C_{1-6}$alkyl (e.g., —C(O)Me, —C(O)Et, —C(O)Pr, —C(O)Bu, or —C(O)tBu); $R^1$ is H, $R^2$ is $C_{1-6}$alkyl (e.g., Me, Et, Pr, Bu), $R^3$ is H, and $R^4$ is $C_{1-6}$alkyl (e.g., Me, Et, Pr, Bu); n is 1, 2, or 3; m is 1, 2, or 3; j is 1, 2, or 3; and k is 1, 2, or 3;

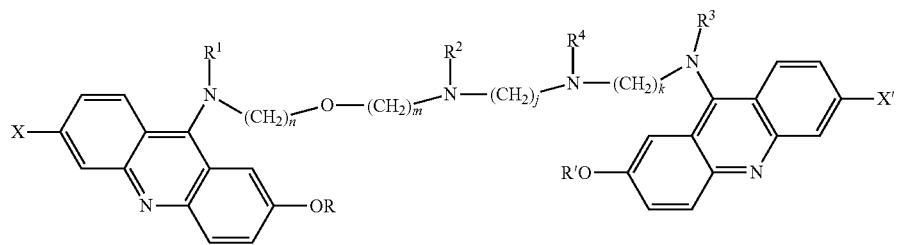

wherein X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, Bu); or R is H and R' is —C(O)$C_{1-6}$alkyl (e.g., —C(O)Me, —C(O)Et, —C(O)Pr, —C(O)Bu, or —C(O)tBu); or R is $C_{1-6}$alkyl (e.g., Me, Et, Pr, Bu) and R' is $C_{1-6}$alkyl (e.g., Me, Et, Pr, Bu); or R is $C_{1-6}$alkyl (e.g., Me, Et, Pr, Bu) and R' is —C(O)$C_{1-6}$alkyl (e.g., —C(O)Me, —C(O)Et, —C(O)Pr, —C(O)Bu, or —C(O)tBu); $R^1$ is H, $R^2$ is $C_{1-6}$alkyl (e.g., Me, Et, Pr, Bu), $R^3$ is H, and $R^4$ is $C_{1-6}$alkyl (e.g., Me, Et, Pr, Bu); n is 1, 2, or 3; m is 1, 2, or 3; j is 1, 2, or 3; and k is 1, 2, or 3;

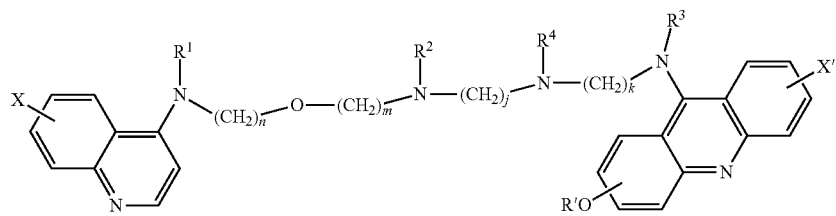

wherein R' is H and X is F and X' is F; or X is Cl and X' is Cl; or X is Br and X' is Br; or X is F and X' is Cl; or X is F and X' is Br; or X is Cl and X' is Br. In some embodiments, R' is $C_{1-6}$alkyl (e.g., Me, Et, Pr, Bu) and X is F and X' is F; or X is Cl and X' is Cl; or X is Br and X' is Br; or X is F and X' is Cl; or X is F and X' is Br; or X is Cl and X' is Br. In some aspects, R' is —C(O)$C_{1-6}$alkyl (e.g., —C(O)Me, —C(O)Et, —C(O)Pr, —C(O)Bu, or —C(O)tBu) and X is F and X' is F; or X is Cl and X' is Cl; or X is Br and X' is Br; or X is F and X' is Cl; or X is F and X' is Br; or X is Cl and X' is Br; $R^1$ is H, $R^2$ is $C_{1-6}$alkyl (e.g., Me, Et, Pr, Bu), $R^3$ is H, and $R^4$ is $C_{1-6}$alkyl (e.g., Me, Et, Pr, Bu); n is 1, 2, or 3; m is 1, 2, or 3; j is 1, 2, or 3; and k is 1, 2, or 3;

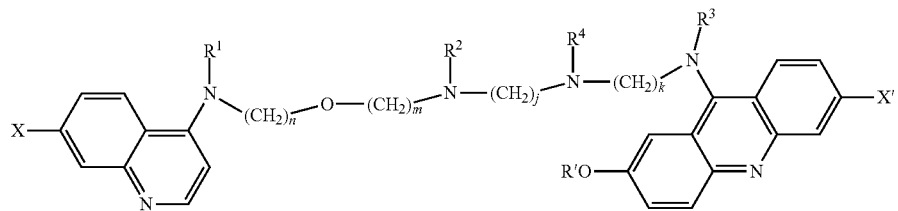

IICc

R' is H and X is F and X' is F; or X is Cl and X' is Cl; or X is Br and X' is Br; or X is F and X' is Cl; or X is F and X' is Br; or X is Cl and X' is Br. In some embodiments, R' is $C_{1-6}$alkyl (e.g., Me, Et, Pr, Bu) and X is F and X' is F; or X is Cl and X' is Cl; or X is Br and X' is Br; or X is F and X' is Cl; or X is F and X' is Br; or X is Cl and X' is Br. In some aspects, R' is —C(O)$C_{1-6}$alkyl (e.g., —C(O)Me, —C(O)Et, —C(O)Pr, —C(O)Bu, or —C(O)tBu) and X is F and X' is F; or X is Cl and X' is Cl; or X is Br and X' is Br; or X is F and X' is Cl; or X is F and X' is Br; or X is Cl and X' is Br; $R^1$ is H, $R^2$ is $C_{1-6}$alkyl (e.g., Me, Et, Pr, Bu), $R^3$ is H, and $R^4$ is $C_{1-6}$alkyl (e.g., Me, Et, Pr, Bu); n is 1, 2, or 3; m is 1, 2, or 3; j is 1, 2, or 3; and k is 1, 2, or 3;

In some aspects, the compounds of formula III include

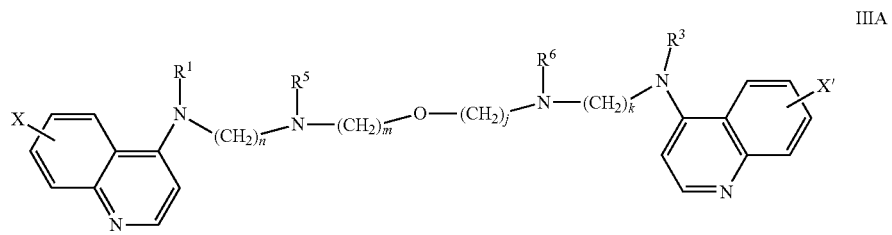

IIIA wherein X is F and X' is F; or X is Cl and X' is Cl; or X is Br and X' is Br; or X is F and X' is Cl; or X is F and X' is Br; or X is Cl and X' is Br; $R^1$ is H, $R^3$ is H, $R^5$ is $C_{1-6}$alkyl (e.g., Me, Et, Pr, Bu), and $R^6$ is $C_{1-6}$alkyl (e.g., Me, Et, Pr, Bu); n is 1, 2, or 3; m is 1, 2, or 3; j is 1, 2, or 3; and k is 1, 2, or 3;

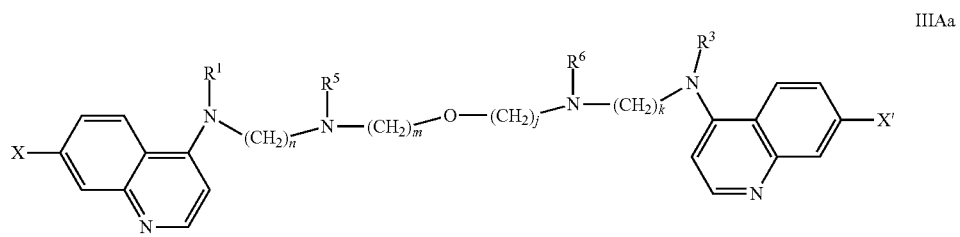

IIIAa wherein X is F and X' is F; or X is Cl and X' is Cl; or X is Br and X' is Br; or X is F and X' is Cl; or X is F and X' is Br; or X is Cl and X' is Br; $R^1$ is H, $R^3$ is H, $R^5$ is $C_{1-6}$alkyl (e.g., Me, Et, Pr, Bu), and $R^6$ is $C_{1-6}$alkyl (e.g., Me, Et, Pr, Bu); n is 1, 2, or 3; m is 1, 2, or 3; j is 1, 2, or 3; and k is 1, 2, or 3;

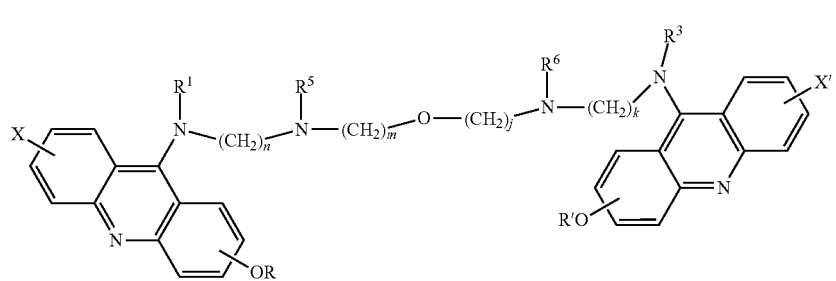

IIIB wherein X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, Bu); or R is H and R' is —C(O)$C_{1-6}$alkyl (e.g., —C(O)Me, —C(O)Et, —C(O)Pr, —C(O)Bu, or —C(O)tBu); or R is $C_{1-6}$alkyl (e.g., Me, Et, Pr, Bu) and R' is $C_{1-6}$alkyl (e.g., Me, Et, Pr, Bu); or R is $C_{1-6}$alkyl (e.g., Me, Et, Pr, Bu) and R' is —C(O)$C_{1-6}$alkyl (e.g., —C(O)Me, —C(O)Et, —C(O)Pr, —C(O)Bu, or —C(O)tBu); $R^1$ is H, $R^3$ is H, $R^5$ is $C_{1-6}$alkyl (e.g., Me, Et, Pr, Bu), and $R^6$ is $C_{1-6}$alkyl (e.g., Me, Et, Pr, Bu); n is 1, 2, or 3; m is 1, 2, or 3; j is 1, 2, or 3; and k is 1, 2, or 3;

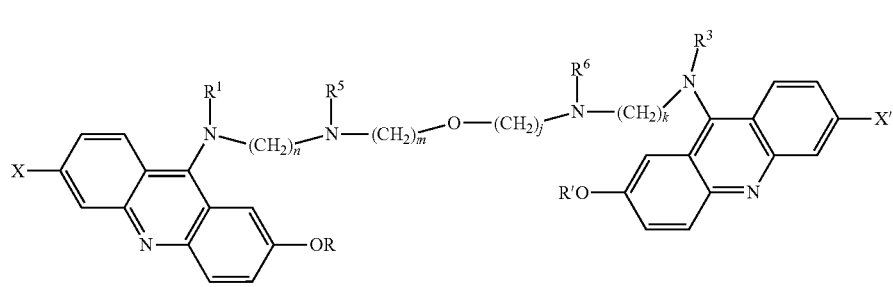

IIIBb wherein X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, Bu); or R is H and R' is —C(O)$C_{1-6}$alkyl (e.g., —C(O)Me, —C(O)Et, —C(O)Pr, —C(O)Bu, or —C(O)tBu); or R is $C_{1-6}$alkyl (e.g., Me, Et, Pr, Bu) and R' is $C_{1-6}$alkyl (e.g., Me, Et, Pr, Bu); or R is $C_{1-6}$alkyl (e.g., Me, Et, Pr, Bu) and R' is —C(O)$C_{1-6}$alkyl (e.g., —C(O)Me, —C(O)Et, —C(O)Pr, —C(O)Bu, or —C(O)tBu); $R^1$ is H, $R^3$ is H, $R^5$ is $C_{1-6}$alkyl (e.g., Me, Et, Pr, Bu), and $R^6$ is $C_{1-6}$alkyl (e.g., Me, Et, Pr, Bu); n is 1, 2, or 3; m is 1, 2, or 3; j is 1, 2, or 3; and k is 1, 2, or 3;

wherein R' is H and X is F and X' is F; or X is Cl and X' is Cl; or X is Br and X' is Br; or X is F and X' is Cl; or X is F and X' is Br; or X is Cl and X' is Br. In some embodiments, R' is $C_{1-6}$alkyl (e.g., Me, Et, Pr, Bu) and X is F and X' is F; or X is Cl and X' is Cl; or X is Br and X' is Br; or X is F and X' is Cl; or X is F and X' is Br; or X is Cl and X' is Br. In some aspects, R' is —C(O)$C_{1-6}$alkyl (e.g., —C(O)Me, —C(O)Et, —C(O)Pr, —C(O)Bu, or —C(O)tBu) and X is F and X' is F; or X is Cl and X' is Cl; or X is Br and X' is Br; or X is F and X' is Cl; or X is F and X' is Br; or X is Cl and X' is Br; $R^1$ is H, $R^3$ is H, $R^5$ is $C_{1-6}$alkyl (e.g., Me, Et, Pr, Bu), and $R^6$ is $C_{1-6}$alkyl (e.g., Me, Et, Pr, Bu); n is 1, 2, or 3; m is 1, 2, or 3; j is 1, 2, or 3; and k is 1, 2, or 3;

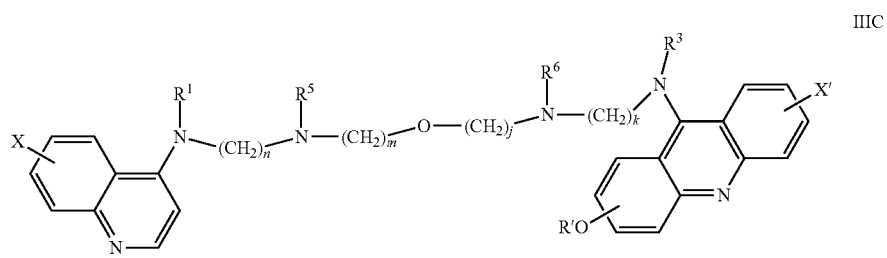

IIIC

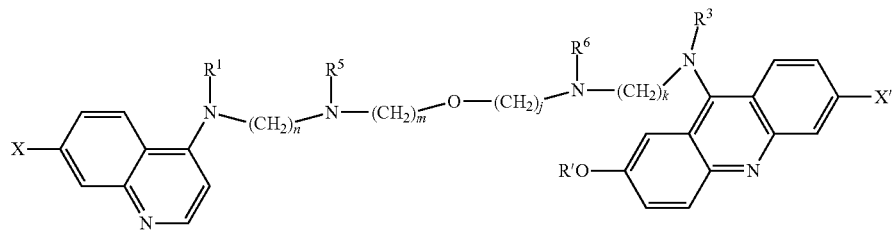

R' is H and X is F and X' is F; or X is Cl and X' is Cl; or X is Br and X' is Br; or X is F and X' is Cl; or X is F and X' is Br; or X is Cl and X' is Br. In some embodiments, R' is $C_{1-6}$alkyl (e.g., Me, Et, Pr, Bu) and X is F and X' is F; or X is Cl and X' is Cl; or X is Br and X' is Br; or X is F and X' is Cl; or X is F and X' is Br; or X is Cl and X' is Br. In some aspects, R' is —C(O)$C_{1-6}$alkyl (e.g., —C(O)Me, —C(O)Et, —C(O)Pr, —C(O)Bu, or —C(O)tBu) and X is F and X' is F; or X is Cl and X' is Cl; or X is Br and X' is Br; or X is F and X' is Cl; or X is F and X' is Br; or X is Cl and X' is Br; $R^1$ is H, $R^3$ is H, $R^5$ is $C_{1-6}$alkyl (e.g., Me, Et, Pr, Bu), and $R^6$ is $C_{1-6}$alkyl (e.g., Me, Et, Pr, Bu); n is 1, 2, or 3; m is 1, 2, or 3; j is 1, 2, or 3; and k is 1, 2, or 3;

In some aspects, the compounds of formula I include:

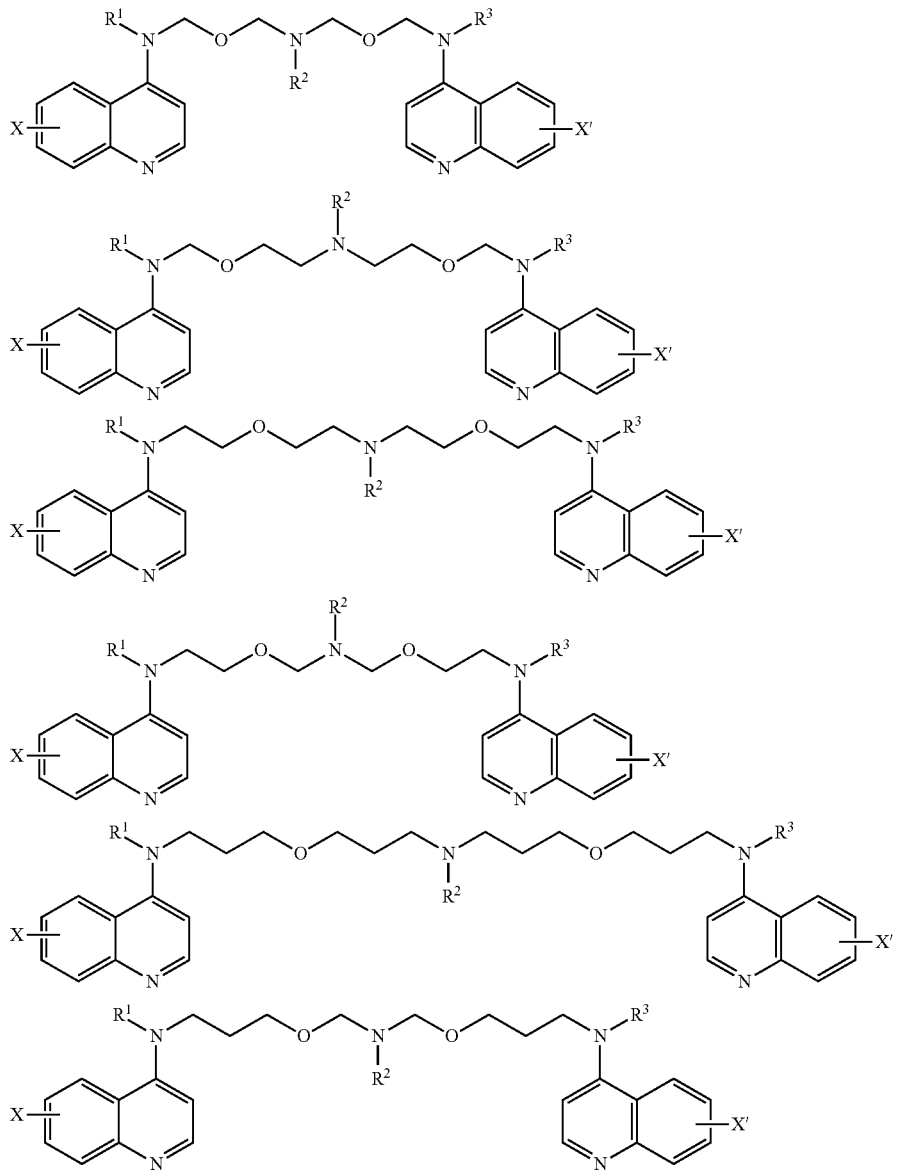

-continued
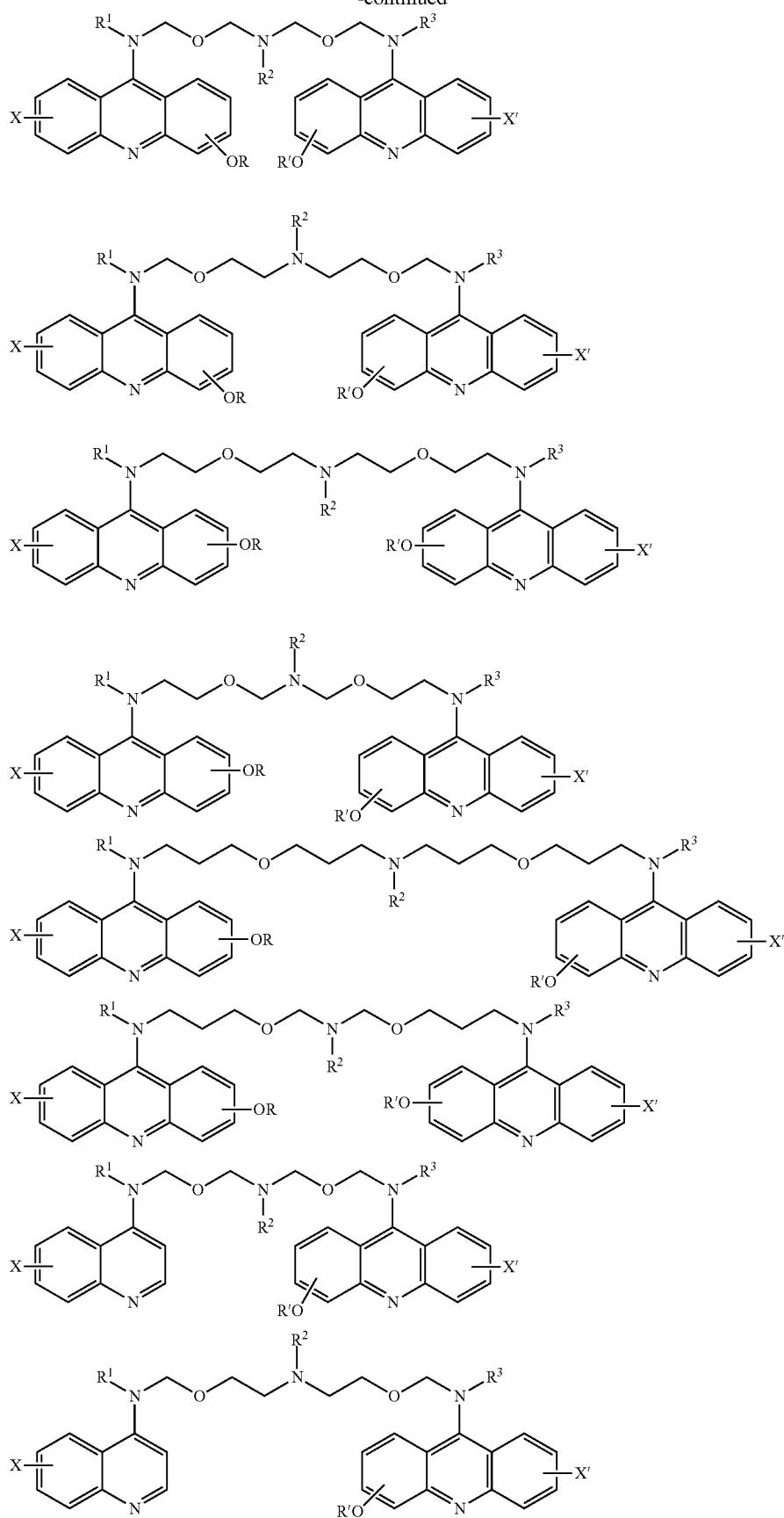

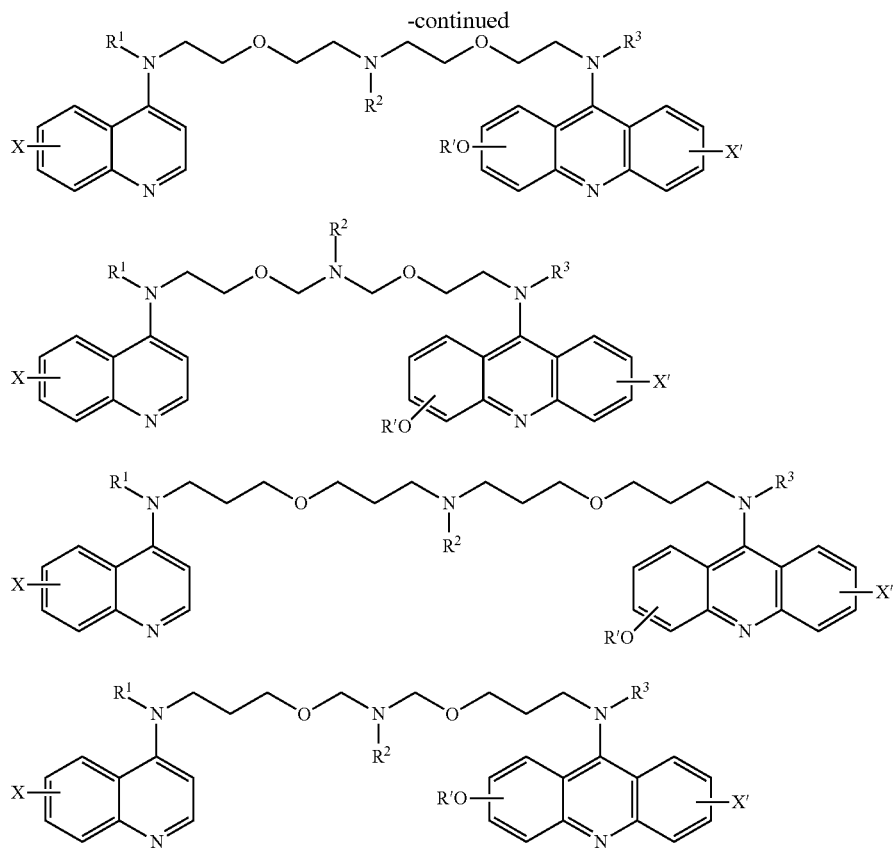

wherein X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, flu); or R is H and R' is —C(O)$C_{1-6}$alkyl (e.g., —C(O)Me, —C(O)Et, —C(O)Pr, —C(O)Bu, or —C(O)tBlu); or R is $C_{1-6}$alkyl (e.g., Me, Et, Pr, flu) and R' is $C_{1-6}$alkyl (e.g., Me, Et, Pr, flu); or R is $C_{1-6}$alkyl (e.g., Me, Et, Pr, flu) and R' is —C(O)$C_{1-6}$alkyl (e.g., —C(O)Me, —C(O)Et, —C(O)Pr, —C(O)Blu, or —C(O)tBlu); $R^1$ is H, $R^2$ is $C_{1-6}$alkyl (e.g., Me, Et, Pr, flu), and $R^3$ is H; n is 1, 2, or 3; m is 1, 2, or 3; j is 1, 2, or 3; and k is 1, 2, or 3.

In some aspects, the compounds of formula II include:

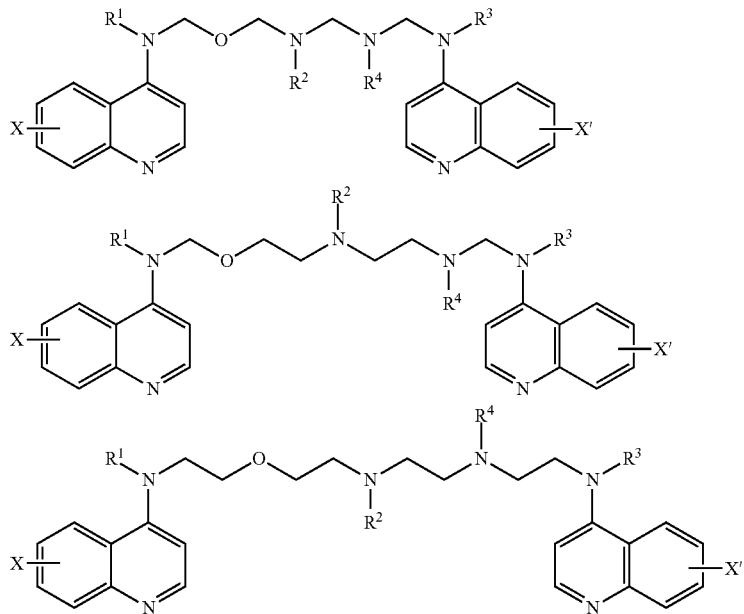

-continued
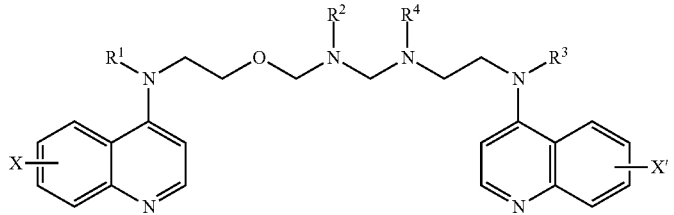
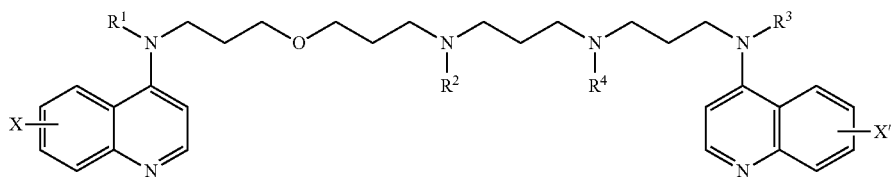
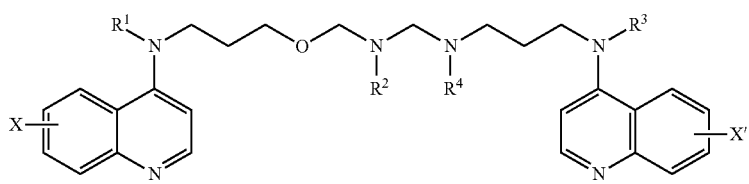
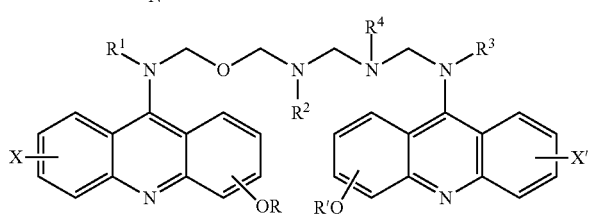
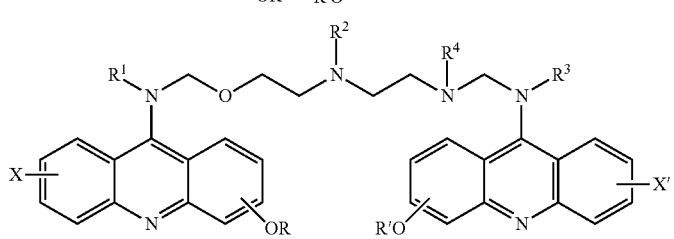
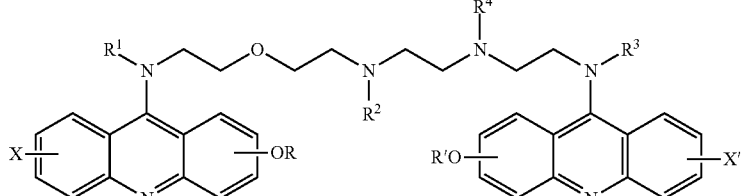
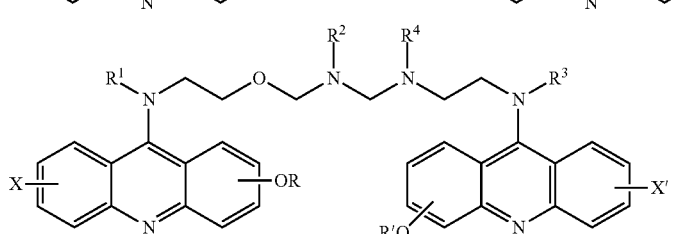
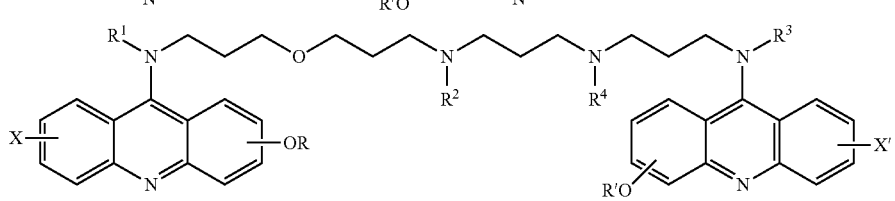

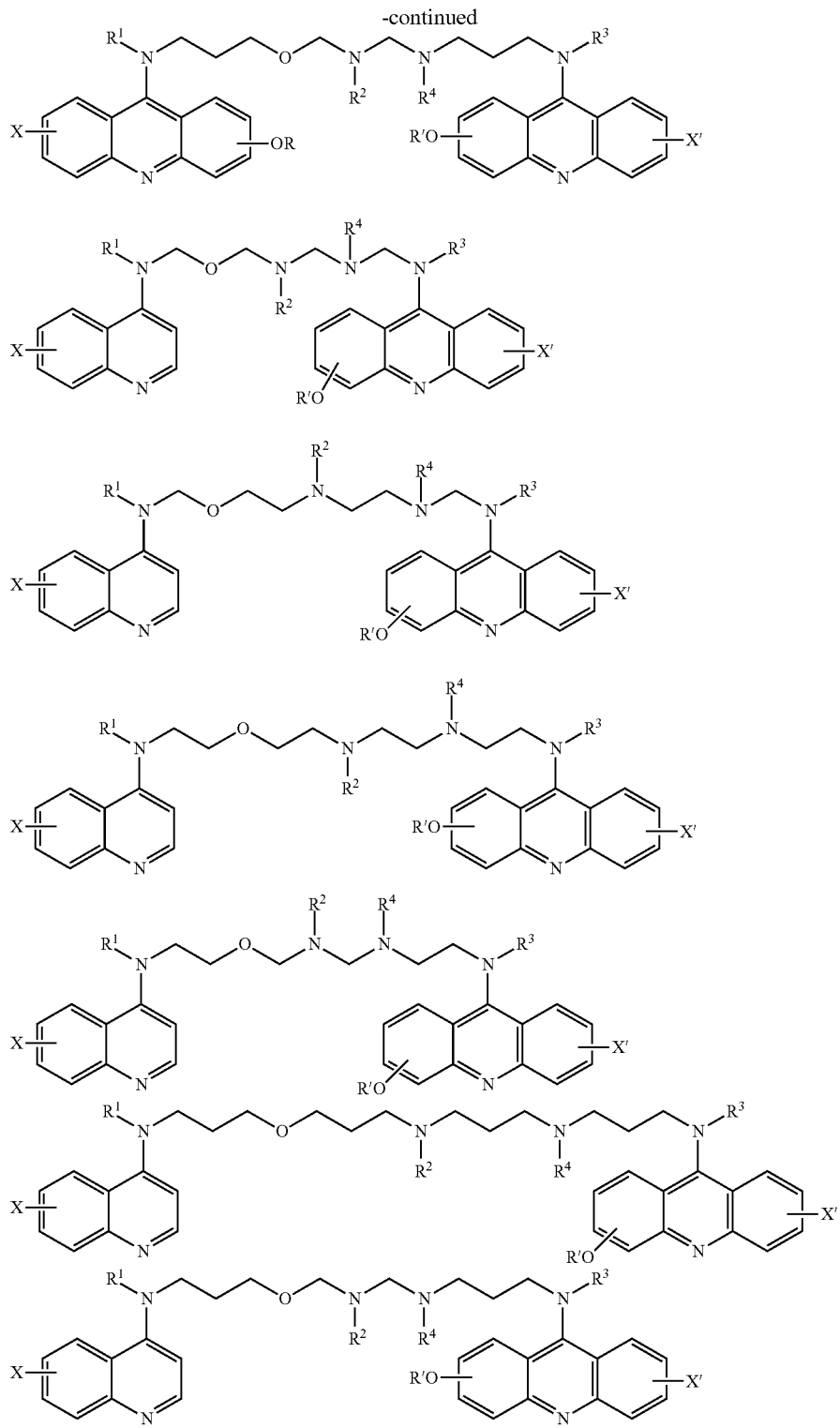

-continued wherein X is F and X' is F; or X is Cl and X' is Cl; or X is Br and X' is Br; or X is F and X' is Cl; or X is F and X' is Br; or X is Cl and X' is Br. Also in these embodiments, R is H and R' is H; or R is H and R' is $C_{1-6}$alkyl (e.g., Me, Et, Pr, Bu); or R is H and R' is —C(O)$C_{1-6}$alkyl (e.g., —C(O)Me, —C(O)Et, —C(O)Pr, —C(O)Bu, or —C(O)tBu); or R is $C_{1-6}$alkyl (e.g., Me, Et, Pr, Bu) and R' is $C_{1-6}$alkyl (e.g., Me, Et, Pr, Bu); or R is $C_{1-6}$alkyl (e.g., Me, Et, Pr, Bu) and R' is —C(O)$C_{1-6}$alkyl (e.g., —C(O)Me, —C(O)Et, —C(O)Pr, —C(O)Bu, or —C(O)tBu); $R^1$ is H, $R^2$ is $C_{1-6}$alkyl (e.g., Me, Et, Pr, Bu), $R^3$ is H, and $R^4$ is $C_{1-6}$alkyl (e.g., Me, Et, Pr, Bu); n is 1, 2, or 3; m is 1, 2, or 3; j is 1, 2, or 3; and k is 1, 2, or 3.

In some aspects, the compounds of formula III include:
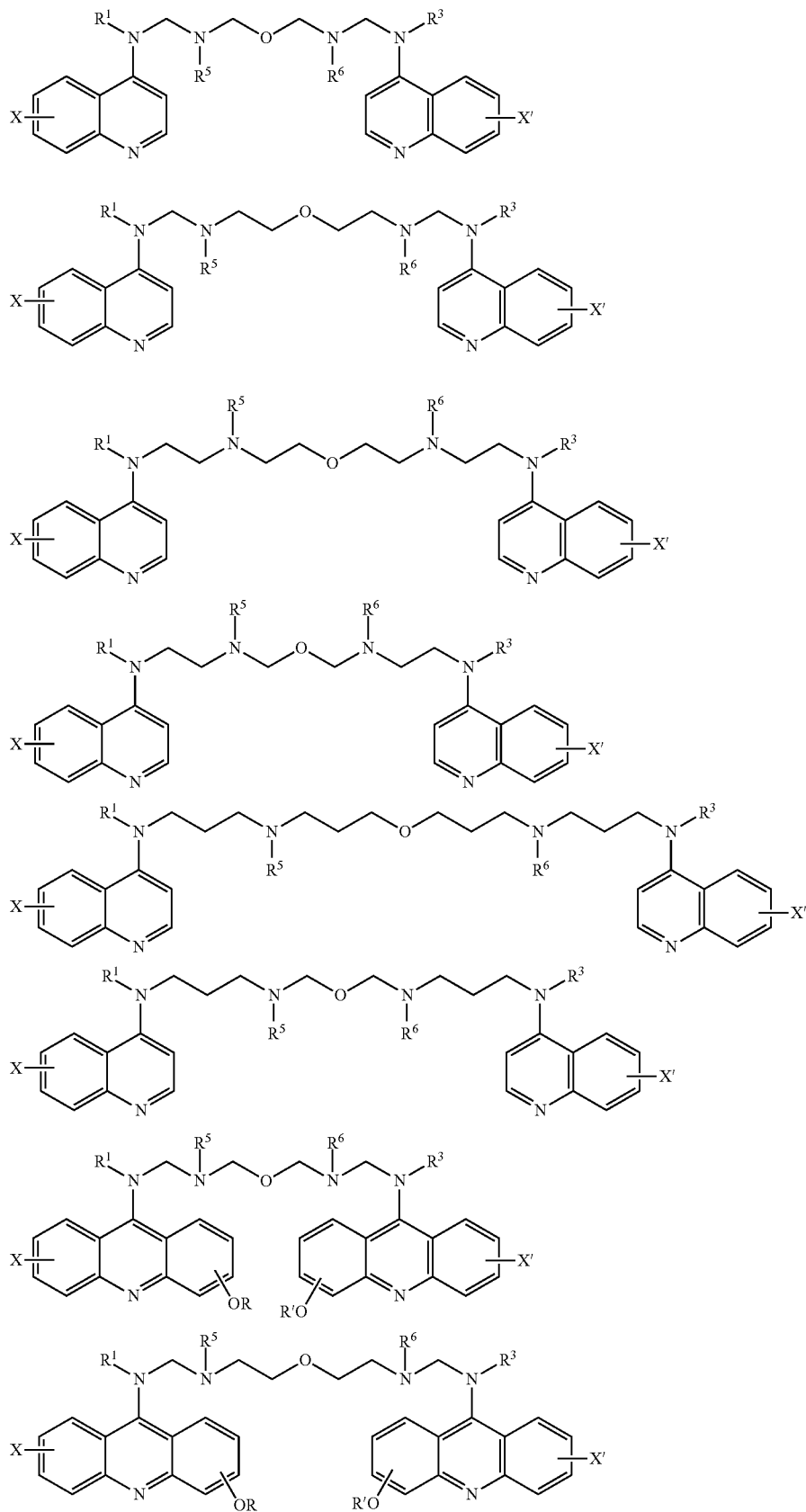

-continued
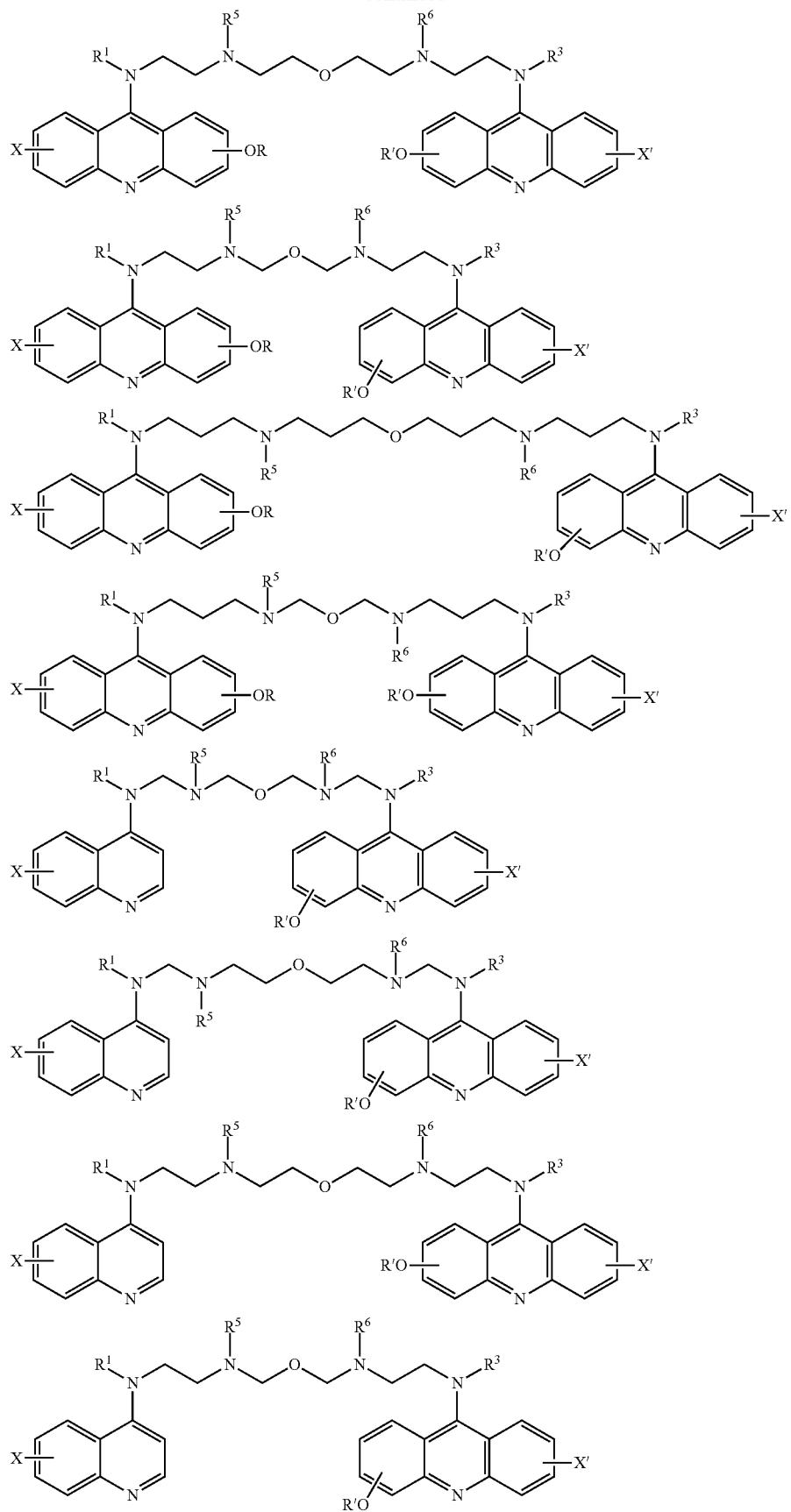

-continued

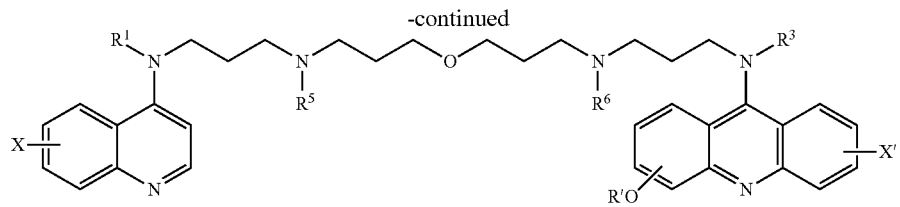

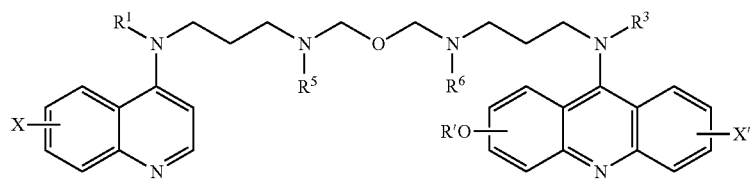

wherein R' is H and X is F and X' is F; or X is Cl and X' is Cl; or X is Br and X' is Br; or X is F and X' is Cl; or X is F and X' is Br; or X is Cl and X' is Br. In some embodiments, R' is $C_{1-6}$alkyl (e.g., Me, Et, Pr, Bu) and X is F and X' is F; or X is Cl and X' is Cl; or X is Br and X' is Br; or X is F and X' is Cl; or X is F and X' is Br; or X is Cl and X' is Br. In some aspects, R' is —C(O)$C_{1-6}$alkyl (e.g., —C(O)Me, —C(O)Et, —C(O)Pr, —C(O)Bu, or —C(O)tBu) and X is F and X' is F; or X is Cl and X' is Cl; or X is Br and X' is Br; or X is F and X' is Cl; or X is F and X' is Br; or X is Cl and X' is Br; $R^1$ is H, $R^3$ is H, $R^5$ is $C_{1-6}$alkyl (e.g., Me, Et, Pr, Bu), and $R^6$ is $C_{1-6}$alkyl (e.g., Me, Et, Pr, Bu); n is 1, 2, or 3; m is 1, 2, or 3; j is 1, 2, or 3; and k is 1, 2, or 3

Compounds of the disclosure also include dioxo-DC331, dioxo-DC551, dioxo-DQ331, and dioxo-DQ551, as well as the pharmaceutically acceptable salts thereof.

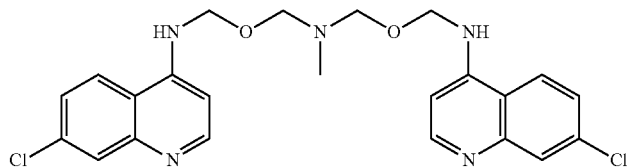

dioxo-DC331

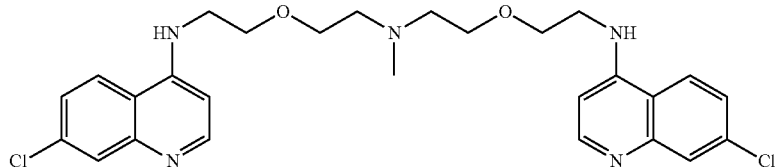

dioxo-DC551

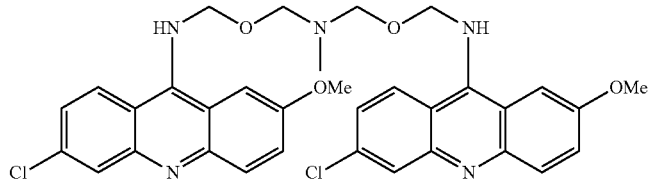

dioxo-DQ331

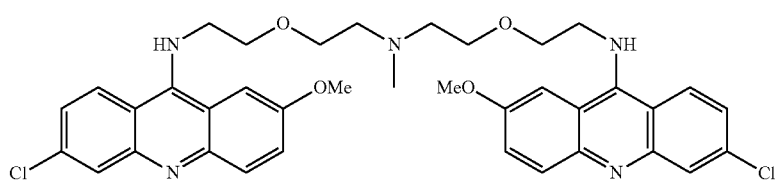

dioxo-DQ551

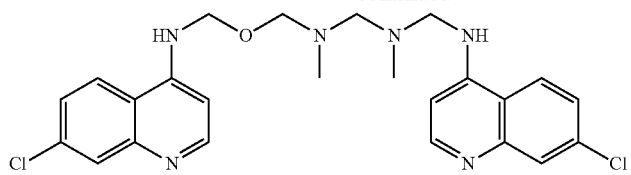
oxo-methylamino-DC331
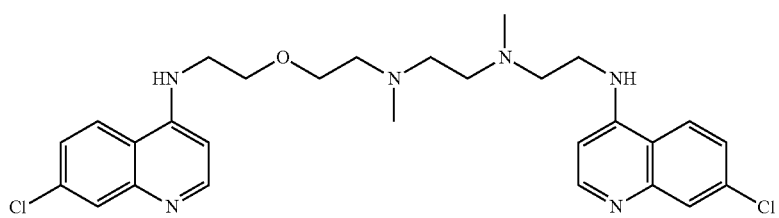
oxo-methylamino-DC551
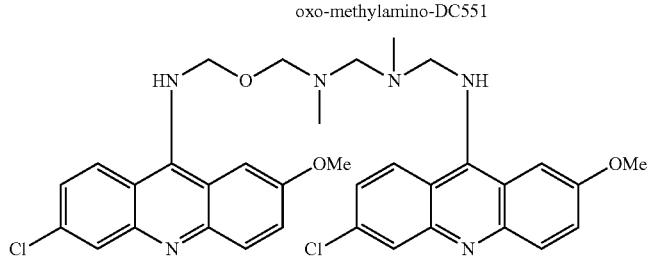
oxo-methylamino-DQ331
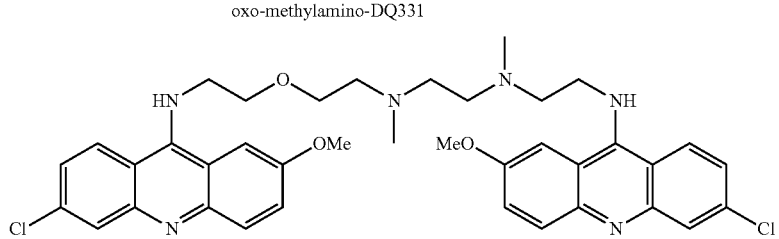
oxo-methylamino-DQ551
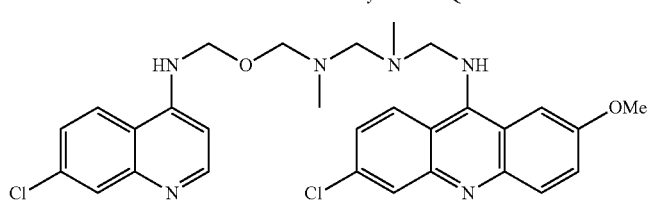
oxo-methylamino-QC331
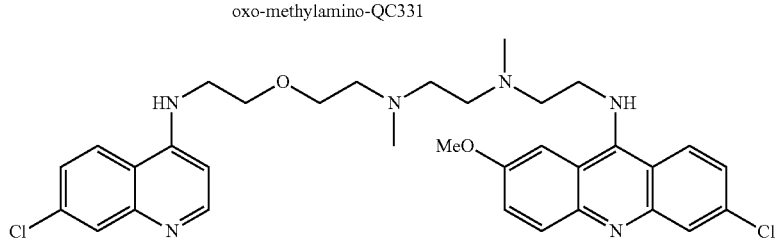
oxo-methylamino-QC551
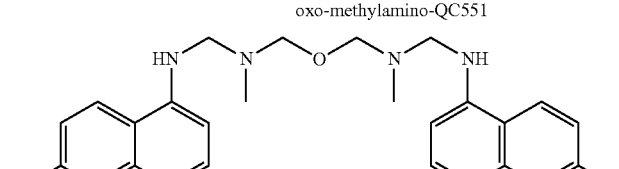
bis-dimethylamino-DC33-oxo -continued

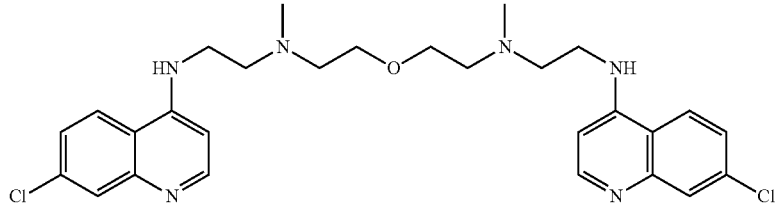
bis-dimethylamino-DC55-oxo

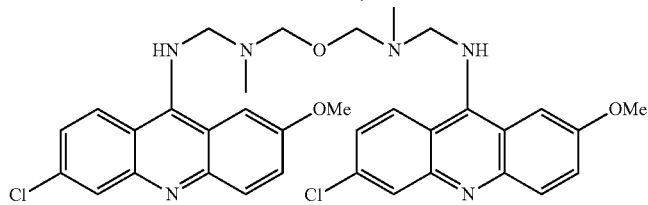
bis-dimethylamino-DC33-oxo

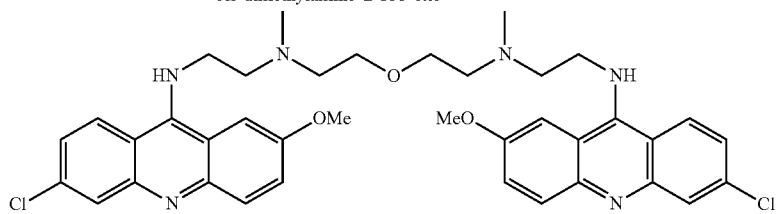
bis-dimethylamino-DQ55-oxo

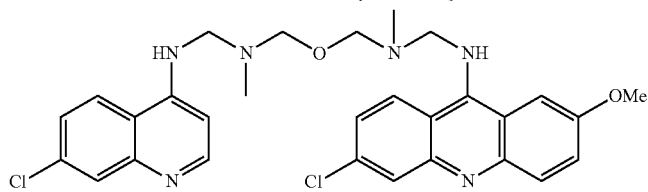
bis-dimethylamino-QC33-oxo

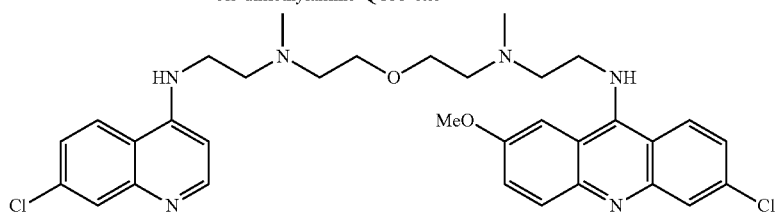
bis-dimethylamino-QC55-oxo

Compounds according to the present invention may be readily formulated into pharmaceutical compositions, useful in the inhibition of autophagy in a biological system and/or the inhibition, treatment or prevention of diseases states and/or conditions which benefit from the inhibition of autophagy including cancer (and its metastasis), rheumatoid arthritis, malaria, antiphospholipid antibody syndrome, lupus (systemic lupus erythematosus), chronic urticaria and Sjogren's disease. Pharmaceutical compositions comprise an effective amount of one or more compounds according to the present invention in combination with a pharmaceutically acceptable carrier, additive or excipient, optionally in combination with at least one additional agent, in the case of cancer, preferably an additional anticancer agent as otherwise described herein.

In methods according to the present invention, subjects or patients in need are treated with the present compounds, pharmaceutical compositions in order to inhibit, reduce the likelihood or treat a disease state, condition and/or infection as otherwise described herein. The disease states, conditions and infections treated by the present compounds and compositions are readily recognized and diagnosed by those of ordinary skill in the art and treated by administering to the patient an effective amount of one or more compounds according to the present invention.

Generally, dosages and routes of administration of the compound are determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, itrathecally or intramuscular injection, among others, including buccal, rectal and transdermal administration. Compositions may also be administered by inhalation to the lungs. Subjects contemplated for treatment according to the method of the invention include humans, companion animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition is about 0.1% to about 85%, about 0.5% to about 75% by weight of a compound or compounds of the invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or is apparent to those skilled in the art; for example, see Remington's Pharmaceutical Sciences (17th Ed., Mack Pub. Co., 1985). The composition to be administered will contain a quantity of the selected compound in a pharmaceutically effective amount for inhibiting autophagy in a biological system, including a patient or subject according to the present invention.

According to one aspect of the invention, a method is provided for treating a mammalian patient or subject to inhibit autophagy in that patient or subject. Compounds according to the present invention described herein may be used to inhibit autophagy in a manner consistent with inhibiting, treating and/or preventing disease states and/or conditions including cancer (including metastasis of cancer), rheumatoid arthritis, malaria, antiphospholipid antibody syndrome, lupus, chronic urticaria and Sjogren's disease.

According to the present invention, in patients or subjects in need thereof, are treated by administering to the patient or subject an effective amount of one or more compounds according to the present invention, optionally in combination with at least one additional bioactive agent useful for treating the same disease state or condition. Compounds according to the present invention may be used to inhibit, reduce the likelihood or treat cancer, including the metastasis of cancer in a patient or subject in need of such treatment. The treatment is useful for any cancer for which inhibition of autophagy represents a favorable result or for which metastasis is a risk element. Therapy with at least one additional anticancer agent as otherwise described herein is also contemplated in the present methods. The numerous cancers which may be treated pursuant to the present method are described hereinabove.

In another aspect the present invention is directed to a method for treating a disease state and/or condition which benefits from the inhibition of autophagy, including rheumatoid arthritis, malaria, antiphospholipid antibody syndrome, lupus, chronic urticaria and Sjorgen's disease. In this method, a patient or subject in need of treatment is administered an effective amount of a compound as otherwise described herein optionally in combination with a pharmaceutically acceptable carrier, additive or excipient in order to inhibit, treat and/or prevent the above disease states of conditions. In alternative embodiments, at least one additional bioactive agent is coadministered with a compound according to the present invention.

In another aspect of the disclosure are methods directed to treating cancer in a subject. The term "cancer" shall refer to a proliferation of tumor cells having the unique trait of loss of normal controls, resulting in unregulated growth, lack of differentiation, local tissue invasion, and/or metastasis. As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of dysplasia, or loss of differentiation and orientation of cells, and have the properties of invasion and metastasis. The term cancer also within context, includes drug resistant cancers, including multiple drug resistant cancers, metastatic cancers and/or recurrent cancers. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver, lung, nasopharyngeal, neck, thyroid, ovary, pancreas, prostate, and stomach; leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer (e.g., small cell lung cancer, mixed small cell and non-small cell cancer, pleural mesothelioma, including metastatic pleural mesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma; mixed types of neoplasias, particularly carcinosarcoma and Hodgkin's disease; and tumors of mixed origin, such as Wilms' tumor and teratocarcinomas, among others. It is noted that certain epithelial tumors including ovarian, breast, colon, head and neck, medulloblastoma and B-cell lymphoma, among others are shown to exhibit increased autophagy and are principal target cancers for compounds and therapies according to the present invention.

Compounds of the disclosure may optionally be administered with one or more other chemotherapy agents. Other chemotherapy agents are known in the art and include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH 2 acetate $[C_{59}H_{84}N_{18}Oi_4\text{-}(C_2H_4O_2)]x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, erythropoietin, epoetin alfa and darbepoetin alfa, ipilumumab, vemurafenib and mixtures thereof.

Other chemotherapy agents include, for example, FLT-3 inhibitors, VEGFR inhibitors, EGFR TK inhibitors, aurora kinase inhibitors, PIK-1 modulators, Bcl-2 inhibitors, HDAC inhibitors, c-MET inhibitors, PARP inhibitors, Cdk inhibitors, EGFR-TK inhibitors, IGFR-TK inhibitors, anti-HGF antibodys, PI3 kinase inhibitors, AKT inhibitors, JAK/STAT inhibitors, checkpoint-1 or 2 inhibitors, focal adhesion kinase inhibitors, Map kinase kinase (mek) inhibitors, VEGF trap antibodies, and mixtures thereof.

Synthetic Methods

The preparation of dioxo-DC551 (1) from heterocycle 3 and linker 2 has been described. The preparation of the analogous linked compounds 4 and 6 proceeds in a similar manner using linkers 5 and 7, respectively (Scheme 1).

Scheme 1. Synthesis of dioxo-DC551 Analogs 4 and 6

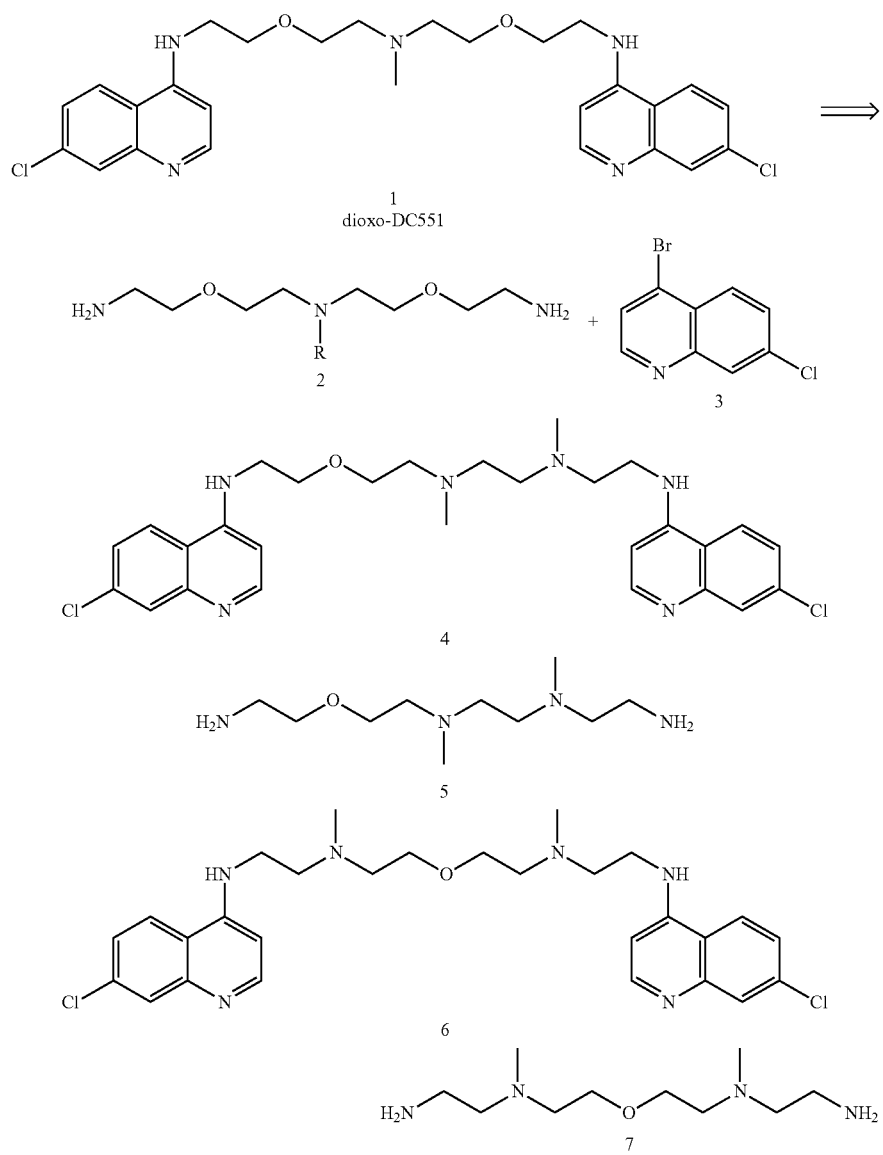

The synthesis of the requisite linker 5 proceeds from the reaction of the commercially available 8 (Merck) and monoprotected triamine 9 (M. Hay, J. Med. Chem. 47, 475 (2004)) to give 10, based on similar transformations reported by O'Driscoll (Chem. Eur. J. 21, 3891 (2015), Wang (Macromolecules 50, 4686, 2018) and Maeda, Bull. Chem. Soc. Japan 56, 212, 1983; Scheme 2).

Scheme 2. Synthesis of Linker 5

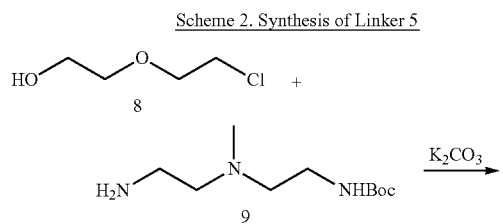

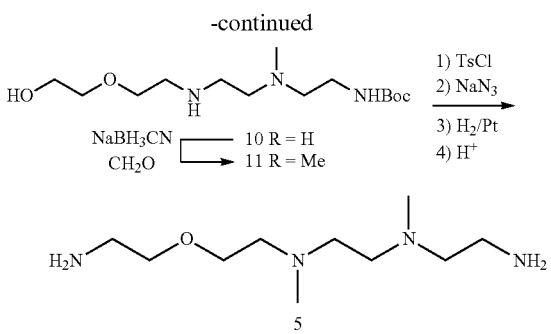

Reductive methylation of the derived secondary amine affords 11. Conversion of the primary alcohol to the amine (via tosylate formation, azide displacement, and reduction), followed by Boc removal, leads to the formation of the new linker 5. Reaction of 5 with 3, under the same conditions described for the synthesis of 1, affords 4. The synthesis of the analogous linked compound 6 proceeds from 7, the synthesis of which has been described by Yoshino (Chem. Comm. 16, 1475 (2000)).

Scheme 3. Synthesis of Heterodimer Analog 12

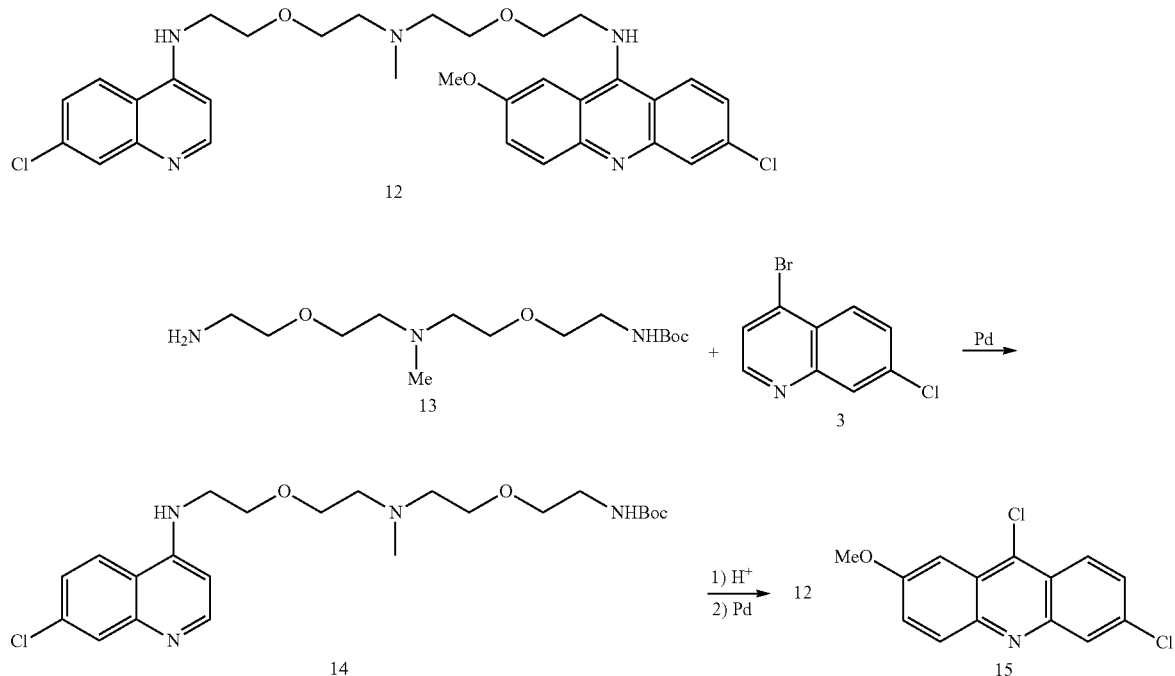

The preparation of the heterodimer analog 12 proceeds from the monoprotected derivative 13 of the previously described linker 2 (R=Me), which on reaction with 3 affords 14 (Scheme 3). Carbamate deprotection followed by Buchwald-Hartwig coupling with 15 affords the desired compound 12.

An alternative approach to the synthesis of 12 proceeds via the formation of a statistical mixture of 12, dioxo-DC551 1, and the quinacrine dimer 17, dioxo-DQ551, which can be separated using standard purification techniques, i.e., flash chromatography. (Scheme 4)

Scheme 4. Alternative Approach to the Synthesis of Heterodimer Analog 12

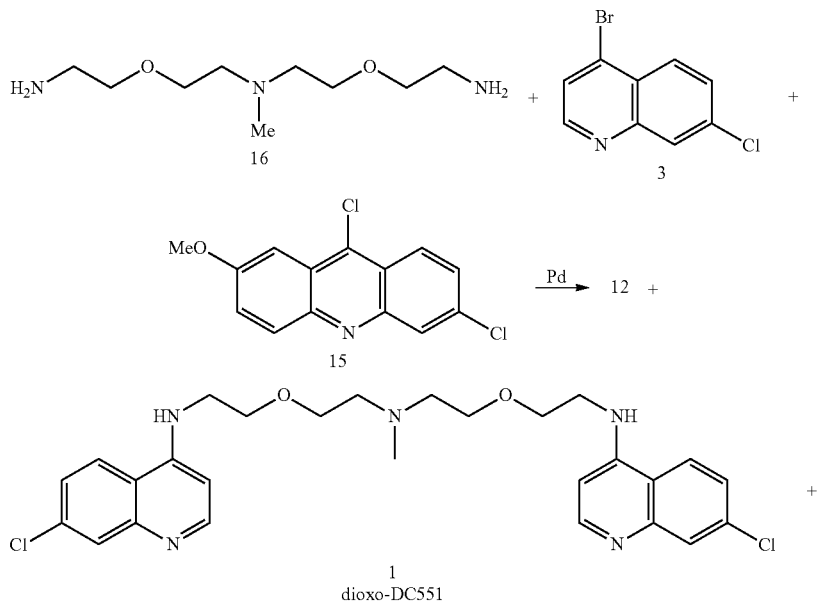

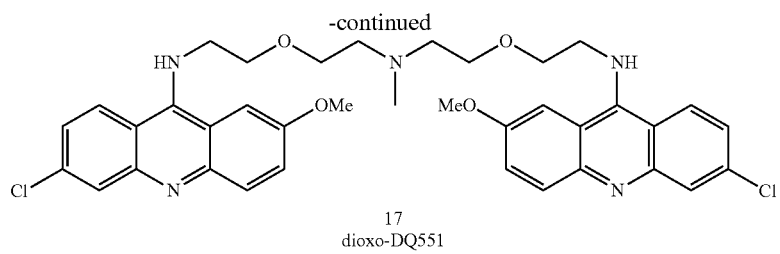

17
dioxo-DQ551

The following examples illustrate and describe the present invention but are not intended to limit the invention in any way.

EXAMPLES

The compounds are prepared as previously described (PNAS) by Buchwald-Hartwig coupling of the appropriate spacer molecule diamine with the requisite starting materials, which are either commercially available or could be readily prepared by standard methods.

In addition, numerous compounds according to the present invention may be readily prepared pursuant to the synthetic methods provided inter alia on pages 21-28 of international application PCT/US2012/035251 (WO 2012/149186), relevant portions of which are incorporated by reference herein. Additional compounds may be prepared by analogy from the disclosed methods as well as analogously from synthetic procedures which are well known in the art. General Synthetic Protocol:

Example 1

The synthesis of the dioxo-5-5-linker, Compound A, is outlined below. The synthesis of Compound B, the linker for the synthesis of the dioxo-3-3 series, is prepared via 0-chloromethylation and subsequent amination of commercially available bis-hydroxymethylamine, after nitrogen protection.

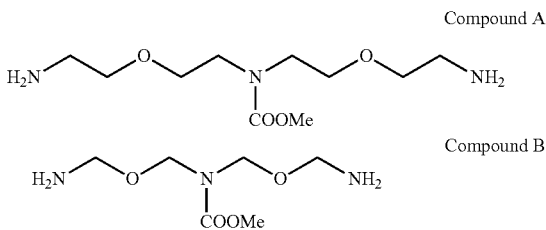

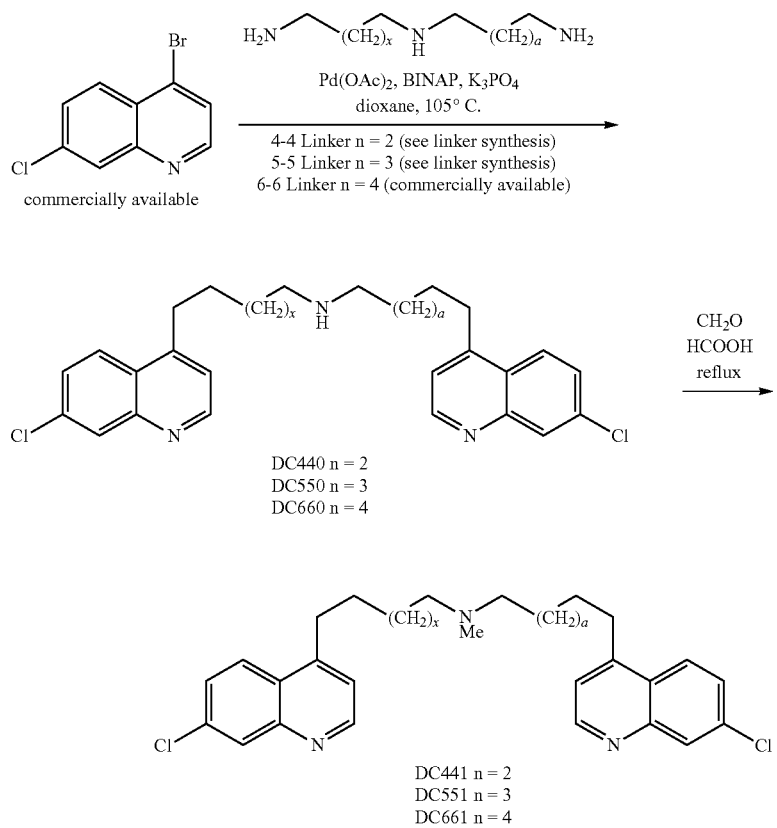

Synthesis of Dioxo Carbamate Linker

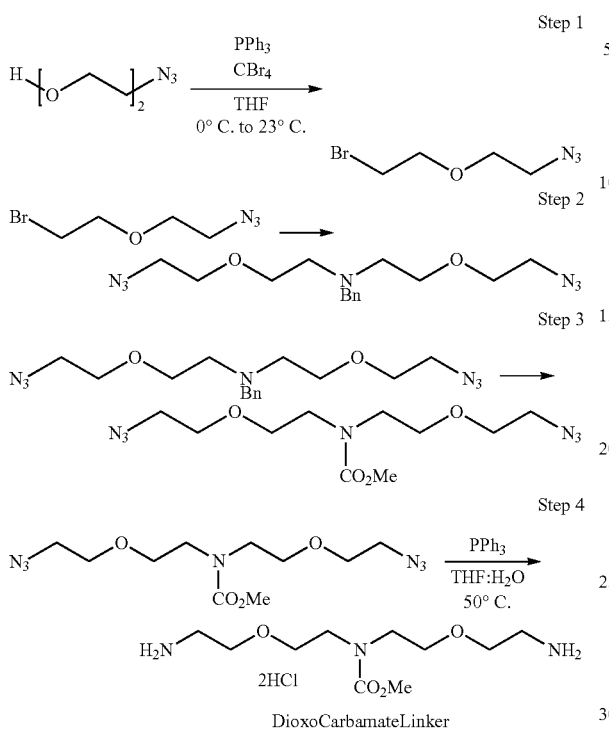

Example 2. Synthesis of Dioxolinker: H$_2$N—CH$_2$—CH$_2$—O—CH$_2$—CH$_2$—NR—CH$_2$—CH$_2$—O—CH$_2$—CH$_2$—NH$_2$ Step 1:

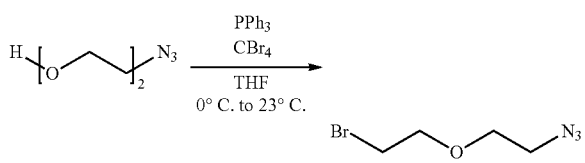

Commercially available azidoalcohol (3.7 g, 28.0 mmol, 1.0 eq.) was added to a round bottom flask along with a stir bar and place under an atmosphere of argon. Tetrahydrofuran (THF) (70 mL) was added to the round bottom flask via a syringe. The solution was cooled to 0° C. in an ice bath and triphenylphosphine (11.8 g, 45 mmol, 1.6 eq.) was added in one portion. Carbon tetrabromide (14.97 g, 45 mmol, 1.6 eq) was added to the reaction in three portions, adding the next portion when the first portion has dissolved. All additions performed while maintaining the 0° C. bath. The reaction was first clear but becomes increasingly brown and opaque through the duration of the reaction. The reaction was stirred for 1 hour at 0° C. The reaction was then warmed to 23 C and stirred for 4 hours. The reaction was considered complete when the starting azido alcohol was consumed by TLC (starting material R$_f$=0.25, 1:3 EtOAc:Hex, KMnO$_4$). The reaction was then concentrated under reduced pressure to afford a paste. The paste was triturated with Et$_2$O (300 mL), and the resulting solid was washed with Et$_2$O (2×100 mL). The combined ethereal fractions were dried over MgSO$_4$ and concentrated to a crude oil. The resulting crude product was purified by column chromatography (SiO$_2$, 65 mm×150 mm, 1:5, EtOAc:Hex) to afford an oil (3.5 g, 64%). The structure of the product was verified by $^1$H NMR. TLC (R$_f$=0.6, 3:1, Hex:EtOAc). $^1$H NMR (500 MHz, CDCl$_3$) δ 3.41 (t, J=5.0 Hz, 2H), 3.48 (t, J=6.2 Hz, 2H), 3.70 (dd, J=5.5, 4.6 Hz, 2H), 3.83 (t, J=6.2 Hz, 2H). $^{13}$C NMR (126 MHz, CDCl$_3$) δ 71.35, 70.13, 50.89, 30.14. FTIR (thin film) λ (cm$^{-1}$): 2867, 2107. HRMS (ESI) C$_4$H$_8$BrN$_3$O: Calculated for [M−N$_2$+H] C$_8$H$_9$BrNO, 165.9868; found: 165.9888.

Step 2:

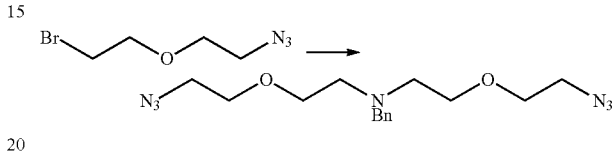

To a round bottom flask the azido-bromide was added (3.581 mmol, 18.5 mmol, 3.0 eq), the reaction was placed under an atmosphere of argon, EtOH (14 mL) was added to dissolve to form a solution, and anhydrous potassium carbonate was added (2.55 g, 18.5 mmol, 3.0 eq). The reaction was placed under a reflux condenser, benzylamine was added (672 uL, 6.2 mmol, 1.0 eq), and the reaction was heated to reflux in an oil bath (75° C.). The reaction was heated until the benzylamine has been completely bisalkylated, as observed by $^1$H NMR. The reaction was concentrated under reduced pressure to afford a paste. The reaction was partitioned between EtOAc (20 mL) and water (20 mL). The layers were separated, and the water was extracted with EtOAc (25 mL). The combined organic layers were dried over sodium sulfate and concentrated under reduced pressure to afford a crude paste. The paste was purified by flash chromatography (SiO$_2$, 55 mm×150 mm, Hex EtOAc, 4:1) to afford a translucent oil (1.33 g, 65%), the structure of which was confirmed by $^1$H NMR. TLC (R$_f$=0.7, 2:1, Hex:EtOAc, UV254 nm). $^1$H NMR (500 MHz, Chloroform-d) δ 7.36-7.28 (m, 4H), 7.23 (td, J=7.3, 6.9, 1.5 Hz, 1H), 3.73 (s, 2H), 3.58 (dt, J=7.2, 5.3 Hz, 8H), 3.35 (t, J=5.0 Hz, 4H), 2.79 (t, J=6.0 Hz, 4H). $^{13}$C NMR (126 MHz, CDCl$_3$) δ 139.87, 128.92, 128.35, 127.05, 70.22, 69.88, 60.02, 54.08, 50.98. FTIR (thin film) λ (cm$^{-1}$): 2864, 2107. HRMS (ESI) C$_{15}$H$_{23}$N$_7$O$_2$: Calculated for [M+H] C$_{15}$H$_{24}$N$_7$O$_2$, 334.1991; found: 334.1991.

Step 3:

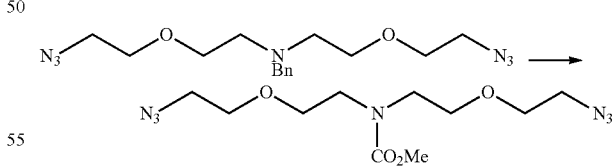

The tertiary amine (900 mg, 2.7 mmol, 1.0 equiv.) was added to a round bottom flask followed by sodium bicarbonate (125 mg, 1.5 mmol, 0.6 eq), and was placed under an argon atmosphere with a stir bar. The reaction was dissolved in toluene (3.8 mL) and methylchloroformate (250 uL, 3.2 mmol, 1.2) was added to the reaction dropwise while the reaction was stirring. The reaction was then heated to 85° C. in an oil bath until the starting tertiary amine was consumed as observed by TLC (R$_f$=0.7, 2:1, Hex:EtOAc, UV 254). The reaction was cooled to 23° C. and concentrated under reduced pressure to afford a crude paste. The paste was purified by column chromatography (SiO$_2$, 2:1, Hex:EtOAc) to afford a translucent oil (770 mg, 97%). The structure of the crude oil was verified by $^1$H NMR. TLC (R$_f$=0.2, 2:1, Hex:EtOAc). $^1$H NMR (500 MHz, Chloroform-d) δ 3.70 (s, 3H), 3.67-3.56 (m, 8H), 3.56-3.50 (m, 4H), 3.36 (t, J=5.0 Hz, 4H). $^{13}$C NMR (126 MHz, CDCl$_3$) δ 156.85, 69.98, 69.89, 69.74, 52.67, 52.64, 50.88, 48.41, 47.96. FTIR (thin film) λ (cm$^{-1}$): 2867, 2109, 1702. HRMS (ESI) C$_{10}$H$_{19}$N$_7$O$_4$: Calculated for [M+H] C$_{10}$H$_{20}$N$_7$O$_4$, 302.1577; found: 302.1590.

Step 4. Synthesis of Compound A

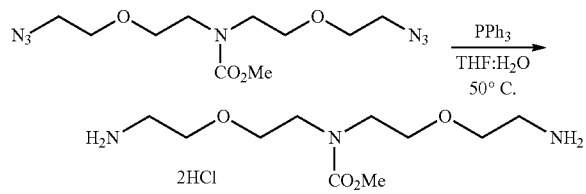

The bisazide (540 mg, 1.9 mmol, 1.0 equiv.) was added to a round bottomed flask along with a stir bar. The reaction vessel was placed under an atmosphere of argon, and the contents of the flask were dissolved in THF (2.8 mL). Triphenylphosphine (992 mg, 3.8 mmol, 2.0 equiv.) was added to the reaction vessel, and the reaction was stirred at 50° C. Water (1 mL, 55 mmol, 29.0 equiv.) was added via a syringe to the reaction vessel and the reaction was heated until the all azide containing compounds were reduced as observed via LCMS. The reaction was then concentrated to a paste and dissolved in CH$_2$C$_2$ (10 mL). The organic solution was washed with 1N HCl (4 mL). The organic fraction was extracted (2×5 mL) with 1N HCl and the aqueous layers were combined. The product, now a HCl salt in the aqueous layer, was then back extracted with methylene chloride. The water layer was now frozen and lyophilized to obtain the pure product as a white HCl salt (518 mg, 85%). The structure of the salt was verified by $^1$H NMR. MP (Water) 165-175° C. TLC (R$_f$=0.0, 10:90:1, MeOH: NH$_4$OH:CH$_2$Cl$_2$). $^1$H NMR (500 MHz, CD$_3$OD) δ 3.73-3.63 (m, 12H), 3.59-3.51 (m, 4H), 3.16-3.10 (m, 4H). $^{13}$C NMR (126 MHz, CD$_3$OD) δ 158.91, 70.57, 70.02, 67.73, 53.40, 48.74, 48.02, 40.57. FTIR (thin film) λ (cm$^{-1}$): 2971, 1672, 1485, 1246, 1107. HRMS (ESI) C$_{10}$H$_{23}$N$_3$O$_4$(HCl)$_2$: Calculated for [M+H-2HCl] C$_{10}$H$_{24}$N$_3$O$_4$, 250.1767; found: 250.1750.

Example 3. Synthesis of Linked N-Carbamate

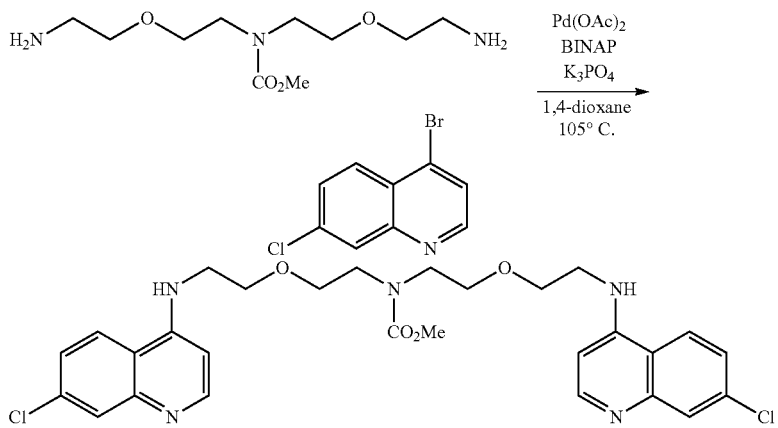

To a reaction vessel 4-bromo-7-chloroquinoline (290 mg, 1.2 mmol, 2.2 eq) was added followed by the diamine (175 mg, 1.0 mmol, 1.0 eq), Pd(OAc)$_2$ (6 mg, 0.03 mmol, 0.05 eq), BINAP (74 mg, 0.12 mmol, 0.1 eq), K$_3$PO$_4$ (578 mg, 3.0 mmol, 5.0 eq). The reaction vessel was then sealed and placed under an atmosphere of argon. 1,4-dioxane was degassed and added to the reaction via a syringe (1.4 mL, rxn conc. 0.4 M). The reaction was then heated at 105° C. for 20 hours. The reaction was cooled to room temperature and considered to be complete when 4-bromo-7-chloroquinoline was consumed as observed via TLC (R$_f$=0.65, 3 Hexanes:1 EtOAc). The reaction was filtered through celite using ethyl acetate (EtOAc) and concentrated to a solid (530 mg). The reaction was then purified by flash chromatography (SiO$_2$, 25 mm×130 mm, gradient: MeOH:NH$_4$OH: CH$_2$Cl$_2$; 1:98:1 (50 mL), 2:97:1 (50 mL), 3:96:1 (50 mL), 4:95:1 (50 mL), 8:91:1 (50 mL), 10:89:1 (100 mL)). The product was isolated as a yellow white solid (266 mg, 86%), the structure of which was confirmed by $^1$H NMR. $^1$H NMR (500 MHz, CDCl$_3$) δ 8.50 (d, J=5.4 Hz, 2H), 7.94 (d, J=2.2 Hz, 2H), 7.32 (s, 2H), 6.37 (d, J=5.9 Hz, 2H), 5.73 (d, J=143.3 Hz, 2H), 3.82-3.35 (m, 19H). $^{13}$C NMR (126 MHz, CDCl$_3$) δ 157.32, 151.80, 148.98, 135.18, 128.63, 128.42, 125.60, 125.32, 122.10, 121.41, 117.44, 99.30, 70.01, 69.44, 68.89, 68.48, 53.07, 53.05, 47.84, 43.18, 42.95. FTIR (thin film) λ (cm$^{-1}$): 2869, 1691, 1611, 1579, 1539. HRMS (ESI) C$_{28}$H$_{31}$Cl$_2$N$_5$O$_4$: Calculated for [M+H] C$_{28}$H$_{32}$Cl$_2$N$_5$O$_4$, 572.1831; found: 572.1823.

Example 4. Synthesis of Dioxo-DC660

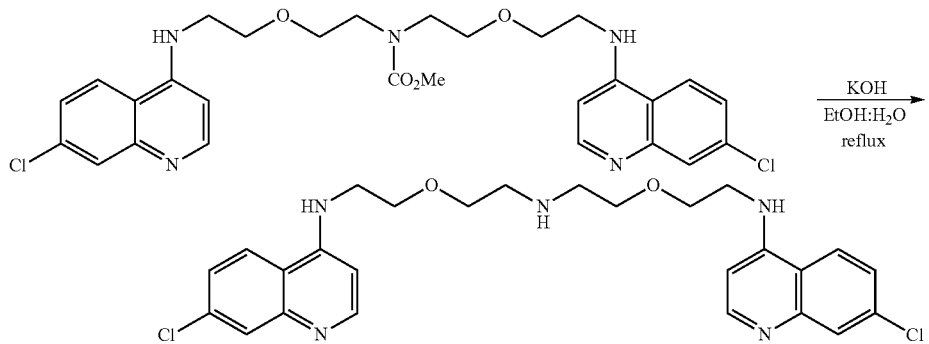

The carbamate (37 mg, 0.07 mmol, 1.0 equiv.) was added to a screw-cap vial followed by solid KOH (150 mg, 3 mmol, 45 equiv.). The reaction contents were placed under an atmosphere of argon and dissolved in a 2:1 mixture of methanol and water (600 uL). The reaction was then heated for 48 hours at 100° C. The reaction was monitored by consumption of the starting material via TLC ($R_f$=0.5, 5:95:1, MeOH:NH$_4$OH:CH$_2$Cl$_2$). The completed reaction was then concentrated under reduced pressure to remove the methanol. The resulting pasted was partitioned between CHCl$_3$ (1 mL) and water (1 mL). The layers were separated, and the water layer was extracted with CHCl$_3$ (3×1 mL). The combined organic layers were dried over anhydrous sodium sulfate and concentrated to a crude paste. Purification of the paste by column chromatography (15 mm×150 mm, gradient 3:96:1 to 6:93:1, MeOH:NH$_4$OH:CH$_2$Cl$_2$) yielding a white yellow film (27 mg, 79%). TLC ($R_{f2}$ 0.2, 5:95:1, MeOH:CH$_2$Cl$_2$:NH$_4$OH). $^1$H NMR (500 MHz, Chloroform-d) δ 8.48 (d, J=5.3 Hz, 2H), 7.91 (d, J=2.1 Hz, 2H), 7.70 (d, J=9.0 Hz, 2H), 7.31-7.24 (m, 2H), 6.33 (d, J=5.3 Hz, 2H), 5.63 (t, J=5.1 Hz, 2H), 3.72 (dd, J=5.7, 4.6 Hz, 4H), 3.62-3.56 (m, 4H), 3.38 (q, J=5.1 Hz, 4H), 2.84 (t, J=5.1 Hz, 4H), 1.23 (t, J=7.0 Hz, 1H). $^{13}$C NMR (126 MHz, CDCl$_3$) δ 152.19, 149.92, 149.32, 135.00, 128.93, 125.39, 121.43, 117.50, 99.39, 77.44, 77.19, 76.93, 70.61, 68.82, 49.40, 42.85. FTIR (thin film) λ (cm$^{-1}$): 3269, 2869, 1611, 1580, 1541, 1451, 1429, 1368, 1332, 1280, 1251, 1142, 1118. HRMS (ESI) C$_{26}$H$_{29}$Cl$_2$N$_5$O$_2$: Calculated for [M+H] C$_{26}$H$_{30}$Cl$_2$N$_5$O$_2$, 514.1777; found: 514.1760.

Example 5. Synthesis of DC661

The dimeric inhibitor (11 mg, 0.02 mmol, 1.0 equiv.) was added to a screw-cap vial and placed under an atmosphere of argon. A stock solution was made of CH$_2$O (3.5 uL/110 uL) in CH$_2$Cl$_2$. The inhibitor was dissolved in CH$_2$Cl$_2$ (110 uL) which contained CH$_2$O (3.5 uL, 0.04 mmol, 2.0 equiv.). The reaction was stirred for 2 minutes before adding solid sodium triacetoxyborohydride (18 mg, 0.9 mmol, 4.0). The reaction was stirred for three hours until the starting material was consumed as observed by TLC ($R_f$=0.3, 5:94:1, MeOH:CH$_2$Cl$_2$:NH$_4$OH) and LCMS. The excess sodium triacetoxyborohydride was quenched by the addition of 2N NaOH (500 uL). CH$_2$Cl$_2$ (500 uL) was added to the reaction mixture, and the biphasic mixture was separated. The aqueous layer was extracted with CH$_2$Cl$_2$, the combined organic layers were dried over anhydrous sodium sulfate and concentrated under reduced pressure to afford a crude paste. The crude paste was then purified by column chromatography (SiO$_2$ (pipet), 5:94:1, MeOH:CH$_2$Cl$_2$:NH$_4$OH) to afford a film on a vial (9 mg, 80%). TLC ($R_f$=0.3, 5:94:1, MeOH:CH$_2$Cl$_2$:NH$_4$OH). $^1$H NMR (500 MHz, Chloroform-d) δ 8.50 (d, J=5.3 Hz, 2H), 7.94 (d, J=2.3 Hz, 2H), 7.71 (d, J=8.9 Hz, 2H), 7.34-7.24 (m, 4H), 6.32 (d, J=5.3 Hz, 2H), 5.63 (d, J=5.4 Hz, 3H), 3.71 (t, J=5.1 Hz, 5H), 3.61 (t, J=5.4 Hz, 5H), 3.36 (q, J=5.1 Hz, 6H), 2.69 (t, J=5.4 Hz, 5H), 2.34 (s, 2H). $^{13}$C NMR (126 MHz, CDCl$_3$) δ 152.23, 149.95, 149.36, 135.00, 128.94, 125.30, 121.55, 117.56, 99.36, 77.44, 77.42, 77.19, 77.16, 76.93, 68.88, 68.43, 57.23, 43.55, 42.78. FTIR (thin film) λ (cm$^{-1}$): 3265, 2870, 1611, 1578, 1538, 1482, 1451, 1428, 1367, 1332, 1280, 1252, 1141, 1120, 1080. HRMS (ESI) C$_{27}$H$_{31}$Cl$_2$N$_5$O$_2$: Calculated for [M+H] C$_{27}$H$_{32}$Cl$_2$N$_5$O$_2$, 528.1933; found: 528.1917.

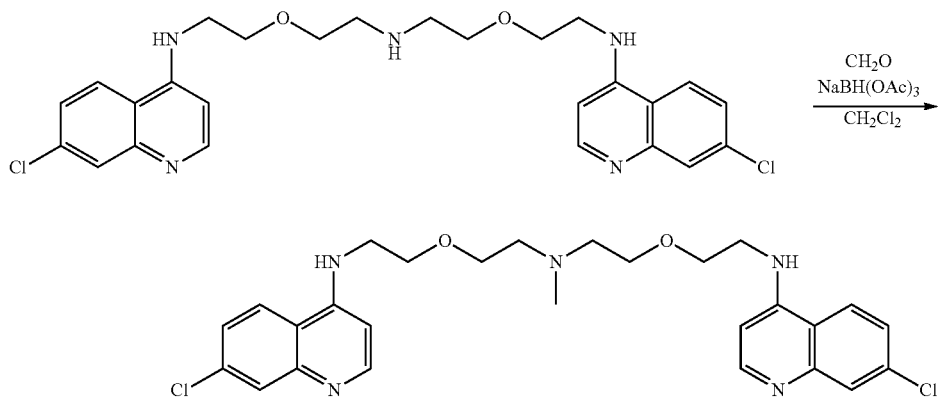

Using the compound A linker with the acridine heterocycle shown below leads to the synthesis of dioxo-DQ-551 according to the general scheme outlined below.
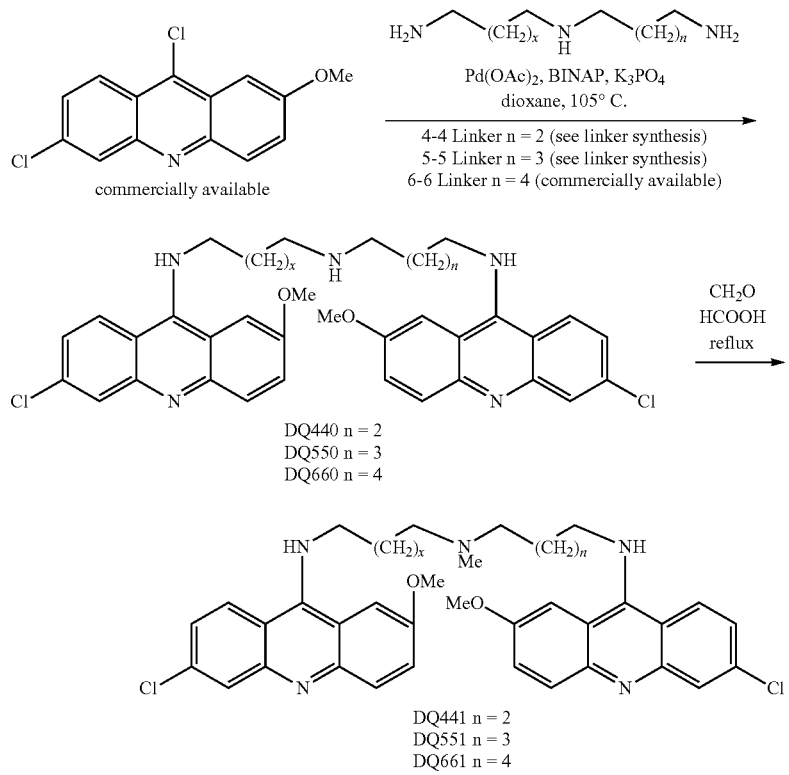
Using the Compound A Linker, as illustrated below, leads to the formation of the dioxo-DQ551:
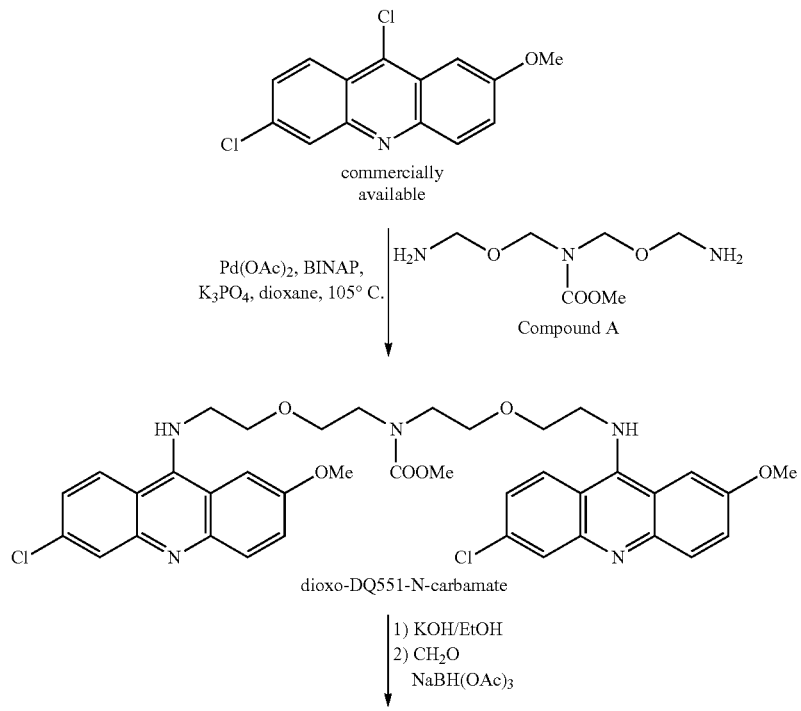

-continued

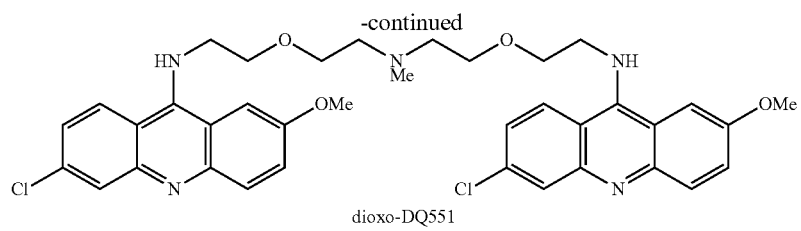

dioxo-DQ551

Example 6. Solubility Across pH (PBS pH 7.4, FaSSGF pH 1.6 & FaSSIF pH 6.5)

Kinetic solubility method was used to determine the solubility of NCEs across pH ranges, PBS pH 7.4, FaSSGF pH 1.6 & FaSSIF pH 6.5.

4. At the end of 90 minutes, samples were filtered using MultiScreen HTS vacuum Manifold assembly and the filtrate was collected into the acceptor plate.
5. An aliquot of 150 µL of filtrate from the above 96-well acceptor plate was transferred into HPLC vials and analyzed by HPLC-UV.

Results are shown in Table 1

TABLE 1

| Compound | FaSSGF pH 1.6 solubility (µM) | FaSSIF pH 6.5 solubility (µM) | PBS pH 7.4 solubility (µM) | Mice blood to plasma ratio | PBS pH 7.4 stability (% remaining @120 min) | Mouse plasma stability (% remaining @ 120 min) |
|---|---|---|---|---|---|---|
| DC-compound A[1] | ~200 | 67 | 160 | 1.78 | 79 | 100 |
| Dioxo-DC-551 | ~200 | ~200 | 199 | 2.25 | 73 | 96 |
| DQ-compound A[2] | 102 | 15 | <1 | 6.23 | 89 | 93 |
| Dioxo-DQ-551 | ~200 | 62 | 39 | 12.6 | 100 | 88 |

[1]DC compound A is a comparative compound and is described in WO 2016/022956
[2]DQ-compound A is a comparative compound and is described in WO2016/0168721

Chemicals and Reagents:

| Chemical/Solvent | Manufacturer | Grade |
|---|---|---|
| Acetonitrile (ACN) | JT Baker, PA, USA | HPLC |
| Ammonium Acetate | Sigma St. Louis, MO, USA | HPLC |
| Dimethyl sulfoxide (DMSO) | Leonid Chemicals (Chemlabs ®), Bangalore, India | Reagent |
| MultiScreen HTS-PCF Filter plate, non-sterile | Merck Millipore, Darmstadt, Germany | Not applicable |
| Phosphate buffer saline (PBS) | Sigma, St. Louis, MO, USA | BioPerformance certified |
| Purified water (Milli-Q water system) | — | Not applicable |
| Sodium chloride | Qualigens, Mumbai, India | Analytical |
| Sodium dihydrogen phosphate | Sigma, St. Louis, MO, USA | Analytical |
| Sodium hydroxide | Ranbaxy Fine Chemicals, New Delhi, India | Analytical |
| Variable pipettes | Eppendorf, Hamburg, Germany | Not applicable |
| 96-Well acceptor plate | Corning, NY, USA | Not applicable |

Procedure

1. Seven calibration standards (i.e. 1, 5, 10, 50, 100, 200 and 300 µM) were prepared in DMSO from the 20 mM primary stock solution.
2. Dispensed an aliquot of 198 IL of 0.001 M PBS into duplicate wells of a multiscreen solubility filter plate.
3. Subsequently, added 2 µL of test compound solution (20 mM primary stock solution), cover the plate and shake at 150 rotations per minute for 90 minutes.

Example 7. Plasma Stability

Stability of drug assessed in plasma to determine the percent remaining and half-life of the compound.

Chemicals and Reagents:

| Chemical/Solvent | Manufacturer | Grade |
|---|---|---|
| Acetonitrile (ACN) | JT Baker PA, USA | HPLC |
| Dimethyl sulfoxide (DMSO) | Leonid Chemicals (Chemlabs ®) Bangalore, India | Reagent |
| Formic acid | Spectrochem, Princess Street, Mumbai, India | Reagent |
| Fresh mouse blood | In-house | Research purpose |
| Purified water | (Milli-Q water system) | ~18.2 MΩ · cm (resistivity) |
| Loperamide Hydrochloride (internal standard, IS) | Sigma Aldrich, St. Louis, MO, USA | Analytical |
| Warfarin (internal standard, IS) | Sigma Aldrich, St.Louis, MO, USA | Analytical |
| Variable pipettes | Eppendorf Hamburg, Germany | Not applicable |

Assay Procedure:

1. Fresh blood was collected in tubes containing anticoagulant (K2 EDTA) and the plasma collected by centrifugation.
2. 3 mM of the test compound was prepared in DMSO from 20 mM main stock.
3. 1 µL of test compound (3 mM) was incubated at 37° C. in 999 µL of plasma (3 µM final concentrations, 0.1% DMSO, final volume 1,000 µL).

4. The reactions were terminated at 0, 30, 60 and 120 min by addition of two volumes of acetonitrile, containing IS (200 ng/mL) resulting in protein precipitation.
5. After termination of reaction at individual time points, the samples were stored at −80±10° C. till the completion of experiment.
6. On completion of last incubation point, all the samples were centrifuge at 14,000 rpm for 10 min.
7. Supernatant (200 µL) from each reaction tube was taken for LC-MS/MS analysis.

Results shown in Table 1.

Example 8. Blood Partitioning

Blood to plasma ratio defines the concentration of a drug in whole blood (that is, target drug containing both erythrocytes and plasma) to the concentration of target drug in plasma. The red blood cell partition coefficient is the ratio of the concentration of drug in the red blood cells (that is, not including plasma) to concentration of drug in plasma.

Chemicals and Reagents:

| Chemical/Solvent | Manufacturer | Grade |
| --- | --- | --- |
| Acetonitrile (ACN) | JT Baker PA, USA | HPLC |
| Chloroquine diphosphate salt | Sigma Aldrich, St. Louis, MO, USA | Analytical |
| Dimethyl sulfoxide (DMSO) | Leonid Chemicals (Chemlabs ®), Bangalore, India | Reagent |
| Formic acid | Spectrochem, Princess Street, Mumbai, India | Reagent |
| Fresh mouse blood | In-house | Research purpose |
| Purified water | (Milli-Q water system) | ~18.2 MΩ · cm (resistivity) |
| Loperamide Hydrochloride (internal standard, IS) | Sigma Aldrich, St. Louis, MO, USA | Analytical |
| Variable pipettes | Eppendorf Hamburg, Germany | Not applicable |

Assay Procedure:
1. Fresh blood was collected.
2. An aliquot of 50 µL blood was taken from individual tubes and centrifuged to check for any haemolysis. Tube with haemolysed blood was not considered for experiment.
3. Non-haemolysed blood in individual tubes was pooled and incubated at 37° C.
4. 999 µL aliquot of pooled blood was taken in individual tubes. One of these tubes was designated for Chloroquine (positive control). Incubations for the test compound were similarly done in other aliquot.
5. 1 µL of test compound (0.1% DMSO concentration) or positive control solution was spiked into each of the above tubes.
6. Above tubes were incubated at 37° C. for 30 min.
7. Post incubation, an aliquot (~50 µL) was taken and centrifuged to check for haemolysis.
8. Subsequently, 100 µL of blood sample from the incubation mixture tube was transferred into a separate labeled tube and quenched with 200 µL of Acetonitrile containing Internal standard.
9. The remaining volume of blood in each tube was centrifuged and plasma was collected.
10. 100 µL aliquot of the plasma sample post centrifugation was transferred into a separate tube and quenched with 200 µL of Acetonitrile containing Internal standard.
11. Finally, the quenched samples (both blood and plasma) were centrifuged and supernatant was transferred into LC-MS/MS vials for analysis.

Results depicted in Table 1.

Example 9. Buffer Stability

Chemicals and Reagents:

| Chemical/Solvent | Manufacturer | Grade |
| --- | --- | --- |
| Acetonitrile (ACN) | JT Baker, PA, USA | HPLC |
| Ammonium Acetate | Sigma St. Louis, MO, USA | HPLC |
| Dimethyl sulfoxide (DMSO) | Leonid Chemicals (Chemlabs ®), Bangalore, India | Reagent |
| MultiScreen HTS-PCF Filter plate, non-sterile | Merck Millipore, Darmstadt, Germany | Not applicable |
| Phosphate buffer saline (PBS) | Sigma, St. Louis, MO, USA | BioPerformance certified |
| Purified water (Milli-Q water system) | In-house | Not applicable |
| Sodium chloride | Qualigens, Mumbai, India | Analytical |
| Sodium dihydrogen phosphate | Sigma, St. Louis, MO, USA | Analytical |
| Sodium hydroxide | Ranbaxy Fine Chemicals, New Delhi, India | Analytical |
| Variable pipettes | Eppendorf, Hamburg, Germany | Not applicable |
| 96-Well acceptor plate | Corning, NY, USA | Not applicable |

Assay Procedure:
1. Test compound was prepared at 3 mM in DMSO from 10 mM working stock.
2. The experiment was conducted in Phosphate buffered saline with a final concentration of 3 µM.
3. The vials were incubated at 37° C. in a hybridization oven for respective time points.
4. After incubation time, equal volumes of quenching solution was added.
5. Samples were centrifuged at 14,000 rpm for 5 min at 4° C.
6. Supernatant was transferred into vials and analyzed in HIPLC.

Results are depicted in Table 1

Example 10. Cytotoxicity Assay

Materials:

| S.No. | Materials | Supplier | Storage |
| --- | --- | --- | --- |
| 1) | DMEM 1X | Gibco | 2-8° C. |
| 2) | RPMI1640 | Gibco | 2-8° C. |
| 3) | Horse Serum, heat inactivated | Invitrogen | 2-8° C. |
| 4) | HI-Fetal bovine serum-500 ml | Invitrogen | −20° C. |
| 3) | Penicillin Streptomycin 100 ML | Invitrogen | −20° C. |
| 4) | DMSO | Sigma | RT |
| 5) | TrypLE Express 100 ml | Invitrogen | RT |
| 6) | 96 well assay plate, black clear bottom with lid | Costar | RT |
| 7) | Alamar Blue ™ Cell Viability Reagent | Invitrogen | 2-8° C. |

Media Preparation Protocol:—
  Media composition for cell preservation (4 ml): 900 μl of Hi-FBS+100 ml of DMSO
Complete Media Preparation (500 ml):
For DLD1n& A375:

| Reagents | Volume | Concentration |
|---|---|---|
| Respective plain Media | 450 ml | |
| 100% Fetal bovine serum | 50 ml | 10% |
| 100x Pen/Strep | 5 ml | 1X |

For MiaPaca2:

| Reagents | Volume | Concentration |
|---|---|---|
| Respective plain Media | 437.5 ml | |
| 100% Horse serum | 12.5 ml | 2.50% |
| 100% Fetal bovine serum | 50 ml | 10% |
| 100x Pen/Strep | 5 ml | 1X |

Cell Line Details:

| Cell line | A375 | DLD1 | MiaPaca-2 |
|---|---|---|---|
| Doubling time | 20 h | 20 h | 40 h |
| Media | DMEM | RPMI1640 | DMEM |

Cell Culture Protocol:—
1) Protocol for Reviving Cell Line(s)
  1. Take out the cell vials from LN2 container & thaw immediately at 37° C.
  2. Wipe it with 70% alcohol properly
  3. Transfer to sterile centrifuge tubes containing 9 ml media & spin at 1000 rpm for 5 min.
  4. Discard the supernatant & resuspend the pellet in 2-3 ml media and transfer to T-75 or T-150 culture flasks containing 15 or 30 ml media respectively.
  5. Incubate at 37° C.-5% $CO_2$.
2) Protocol for Sub-Culturing Cell Line(s)
  Cells should be sub-cultured when they reach 70-80% confluence.
  1. Discard the media from cell culture flask.
  2. Add 3 to 4 ml of TrypLE Express dissociation solution; keep in $CO_2$ incubator for ~5 min. Mix gently to avoid cell clumping.
  3. Add 4.0 to 5.0 ml of complete growth medium and mix gently & transfer to centrifuge tube.
  4. Centrifuge at 1000 rpm for 5 min.
  5. Discard the supernatant & re-suspend the pellet in 3-4 ml of media.
  6. Count the cells in cell counter or using hemocytometer.
  7. Split the cells in 1:2 or 1:4 ratio into new culture flasks.
  8. Incubate cultures at 37° C.-5% $CO_2$ to get confluence
3) Protocol for Preserving Cell Line(s)
  1. Discard the spent media from the TC flask.
  2. Add 3 to 4 ml of TrypLE Express dissociation solution; keep in $CO_2$ incubator for ~5 min. Mix gently to avoid cell clumping.
  3. Add 4.0 to 5.0 ml of complete growth medium and mix gently & transfer to centrifuge tube.
  4. Centrifuge at 1000 rpm for 5 min.
  5. Discard the supernatant & re-suspend the pellet in 3-4 ml of media.
  6. Count the cells in cell counter or using hemocytometer.
  7. Spin at 1000 rpm for 5 min, discard the supernatant and re-suspend the pellet in 900 μl of media+100 μl of DMSO (Freeze app. 1.5 to 3 million cells/vial).
  8. Keep the vials in −80° C. overnight & transfer to LN2 container.

Cell Proliferation (Alamar Blue) Assay:—
  Seed cells at 2000 cells in 100 μL/well in 96-well tissue culture plate. Leave outer wells without cells for background measurements. Incubate at 37° C./5% $CO_2$ for 16-18 hours.
  Add 10× concentration compound dilution or DMSO control so that the final concentration is 1× and DMSO concentration 0.5%. Compound is prepared in 3-fold serial dilutions. Incubate for 72 h at 37° C./5% $CO_2$.
  Add Alamar Blue™ reagent to each well with multichannel pipette and tap gently on each side of the plate to mix. Incubate for 3 hours at 37° C./5% $CO_2$.
  Read plates on fluorescence reader (Tecan i-control, 1.11.1.0, Device: infinite 200, Serial number: 810001990) at 540 nm excitation, 590 nm emission wavelength.
  Data analysis using Graph pad prism
Assay Acceptance Criteria
  S/N Ratio should be >3.
  Z' should be >0.4

TABLE 2

A375 cells

| | $IC_{50}$ (μM) | | $pIC_{50}$ | | Average $pIC_{50}$ | |
|---|---|---|---|---|---|---|
| Compound No | N1 | N2 | N1 | N2 | (n = 2) | SD |
| Doxorubicin | 0.02 | 0.03 | 7.61 | 7.50 | 7.55 | 0.08 |
| Quinacrine | 1.28 | 3.84 | 5.89 | 5.42 | 5.65 | 0.34 |
| DQ Compound A | 0.53 | 0.46 | 6.27 | 6.34 | 6.31 | 0.04 |
| Dioxo-DQ-551 | 0.44 | 1.45 | 6.35 | 5.84 | 6.10 | 0.36 |

TABLE 3

DLD-1 cells

| | $IC_{50}$ (μM) | | $pIC_{50}$ | | Average $pIC_{50}$ | |
|---|---|---|---|---|---|---|
| Compound No | N1 | N2 | N1 | N2 | (n = 2) | SD |
| Doxorubicin | 0.25 | 0.59 | 6.61 | 6.23 | 6.42 | 0.27 |
| Quinacrine | 2.52 | 7.54 | 5.60 | 5.12 | 5.36 | 0.34 |
| DQ-compound A | 0.33 | 0.44 | 6.48 | 6.36 | 6.42 | 0.09 |
| Dioxo-DQ-551 | 0.33 | 1.56 | 6.49 | 5.81 | 6.15 | 0.48 |

TABLE 4

MiaPaCa-2 cells

| | $IC_{50}$ (μM) | | $pIC_{50}$ | | Average $pIC_{50}$ | |
|---|---|---|---|---|---|---|
| Compound No | N1 | N2 | N1 | N2 | (n = 2) | SD |
| Doxorubicin | 0.10 | 0.08 | 7.01 | 7.09 | 7.05 | 0.06 |
| Quinacrine | 2.68 | 2.34 | 5.57 | 5.63 | 5.60 | 0.04 |
| DQ-Compound A | <0.014 | <0.014 | >7.85 | >7.85 | >7.85 | — |
| Dioxo-DQ-551 | 0.15 | 0.21 | 6.82 | 6.69 | 6.76 | 0.09 |

Figure 1B:
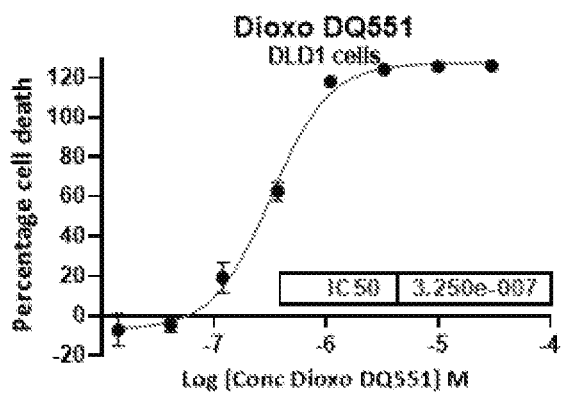
FIG. 1B depicts percentage cell death of DLD cells using an exemplary embodiment of the disclosure, dioxoDQ551.
Figure 1C:
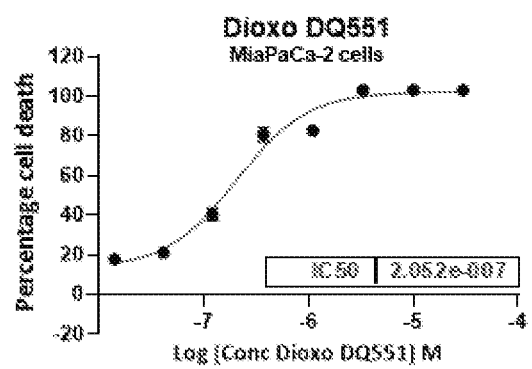
FIG. 1C depicts percentage cell death of DLD cells using an exemplary embodiment of the disclosure, dioxoDQ551.
Figure 2A:
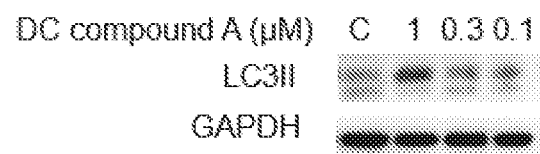
FIGS. 2A, 2B, 2C, and 2D depict immunoblotting against LC3B for exemplary compounds of the disclosure (dioxoDC551 and dioxoDQ551) and comparative compound DC Compound A.
Figure 2B:
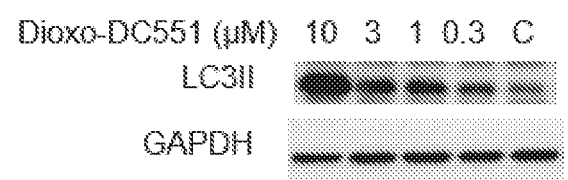
Figure 2C:
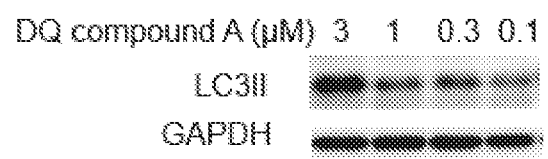
Figure 2D:
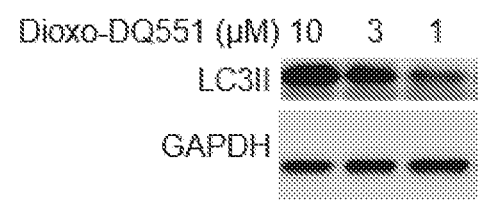

See also, FIGS. 1A, 1B, and 1C

Example 11. Western Blot

Materials

| Components | Supplier | STORAGE |
| --- | --- | --- |
| 30% Acrylamide/Bis | Sigma | 4° C. |
| SDS | Sigma | RT |
| APS | Sigma | 4° C. |
| TEMED | Sigma | 4° C. |
| Tris | Sigma | RT |
| Glycine | Sigma | RT |
| Acetic acid | Qualigens | RT |
| Methanol | Chemlabs | RT |
| Glycerol | Sigma | RT |
| Beta mercapto ethanol | Sigma | RT |
| Bromophenol blue | Sigma | RT |
| Protein marker | Bio-rad | −20° C. |
| Tween 20 | Sigma | RT |
| BSA | Sigma | 4° C. |
| Substrate (Luminata forte) | Millipore | RT |
| PBS | Sigma | RT |
| Sodium chloride | Sigma | RT |
| Sodium orthovanadate | Sigma | RT |
| Protease inhibitor cocktail | Sigma | −20° C. |
| Nitrocellulose membrane | GE | RT |
| Ponceau stain | Sigma | RT |
| Phosphatase Inhibitor Cocktail | Sigma | 4° C. |
| NP 40 | Thermo Scientific | RT |
| Sodium deoxy cholate | Sigma | RT |
| QuantiPro ™ BCA Assay Kit | Sigma | 4° C. |
| Tris PH 7.5 | Invitrogen | 4° C. |

Lysis (RIPA) buffer: Dissolve the components in autoclaved water. Store at 4° C.

| Reagents | Final Concentration |
| --- | --- |
| Tris PH 7.5 | 50 mM |
| NaCl | 150 mM |
| Sodium dodecyl sulphate | 1% |
| EDTA | 1 mM |
| Protease Inhibitor Cocktail | 1X |
| Phosphatase Inhibitor Cocktail | 1X |

Lysis (SDS) buffer: Dissolve the components in autoclaved water. Store at 4° C.

| Reagents | Final Concentration |
| --- | --- |
| Tris PH 7.5 | 50 mM |
| NaCl | 150 mM |
| Sodium dodecyl sulphate | 1% |
| EDTA | 1 mM |
| Protease Inhibitor Cocktail | 1X |
| Phosphatase Inhibitor Cocktail | 1X |

Sample Loading Buffer (5×):

| Components | Quantity |
| --- | --- |
| Tris | 1.5 gms |
| Autoclaved water | 60 ml |
| pH | 6.8 |
| SDS | 4 gms |
| Bromophenol Blue | 4 mg |
| Glycerol | 20 ml |
| BME | 10 ml |
| Final volume | 100 ml |

10× Tris-Glycine (Running Buffer):

| Compound | Weight |
| --- | --- |
| Tris Base | 30.2 g |
| Glycine | 188.0 g |
| SDS | 10.0 g |

Make up the volume with distilled water to 1 liter.

PBST (0.1%): For 1 L: 100 ml of PBS 10×+900 ml ultra pure water+1 ml Tween20

20% SDS: Dissolve 100 g SDS in 450 ml deionized water with gentle stirring and bring to 500 ml. Store at room temperature.

Ammonium persulfate solution (APS): 10% APS (electrophoresis grade) in distilled water.

Blocking buffer preparation: 1% BSA in PBS-Tween 20 (0.1%)

Stripping Buffer: 2% SDS in distilled water with 0.8% beta mercaptoethanol

Transfer Buffer: 25 mM Tris, 192 mM glycine, 20% methanol

Gel Preparation:

Resolving Gel

| Solution | 12% gel |
| --- | --- |
| Distilled H2O | 4.75 ml |
| 1.5M Tris-HCl, pH 8.8 | 2.5 ml |
| 20% (w/v) SDS | 0.05 ml |
| Acrylamide/Bis-acrylamide (30%/0.8% w/v) | 2.64 ml |
| 10% (w/v) ammonium persulfate | 0.05 ml |
| TEMED | 0.01 ml |
| Total Volume | 10.00 ml |

Stacking Gel

| Solution | 4% gel |
| --- | --- |
| H2O | 3.025 ml |
| 0.5M Tris-HCl, pH 6.8 | 1.25 ml |
| 10% SDS | 0.025 ml |
| Acrylamide/Bis-acrylamide mix (30%) | 0.67 ml |
| 10% ammonium persulfate (APS) | 0.025 ml |
| TEMED | 0.005 ml |
| Total volume | 5 ml |

Protocol:

A: Compound Treatment and Sample Processing:
1. Seed $0.3 \times 10^6$ cells/well in 6 well plate and allow to adhere for 16 h at 37° C.—5% $CO_2$
2. Add compounds at the selected concentrations to the complete media in the wells keeping the final DMSO concentration to be 0.1%. Incubate for 24 h at 37° C.—5% $CO_2$ 3. Keeping the plate on ice, remove the media, wash the cells with 1×PBS and add the lysis buffer.
4. Homogenize the cells in lysis buffer by freeze-thaw and by pipetting.
5. Centrifuge the homogenized samples at 10000 rpm for 5 min.
6. Discard the pellet and save the supernatant.
7. Protein estimation by BCA method.
8. Separate the proteins in SDS PAGE followed by western blotting and detection.

B: Protein Estimation Using BCA Method
1. Prepare 1 mg/ml BSA stock solution in water.
2. Prepare BSA standards ranging from 4-250 µg/ml from the stock solution.
3. Add 100 ul of each standard and the cell lysate samples/unknown (diluted 1:10) into micro titer plate.
4. Add 100 ul of BCA reagent (reagent A:B:C::25:24:1) to the wells containing samples and standards and mix plate thoroughly on a plate shaker for 30 seconds and incubate at room temperature for 30 minutes.
5. Measure the absorbance at 562 nm in a plate reader (Tecan Plate Reader)
6. Subtract the average 562 nm absorbance reading of the Blank standard replicates from the sample reading.
7. Use the standard curve to determine the protein concentration of each unknown sample.

C: Sample Preparation for Western Blot:
To about 10-20 µg of protein sample, add 5× loading dye (final concentration should be 1×), boil the samples at 95° C. for 5 min in dry bath.

D: SDS-PAGE and Western Blotting:
1. Load the samples onto the SDS-Polyacrylamide gel and run at 100 mV till the required separation is achieved.
2. Soak nitrocellulose membrane and sponges in tray containing transfer buffer.
3. Keep the gel on Whatmann filter paper and lay membrane on top of gel to make a sandwich.
4. Place the membrane sandwich in transfer unit and fill up with transfer buffer.
5. Transfer the proteins at 100 mV for 90 min at 4° C.
6. Rinse the blot in double distilled water and incubate the blot in blocking solution for 1 hr, at room temperature.
7. Remove blocking solution, wash with PBST and incubate in Primary antibody (in 5% BSA in PBST) and incubate overnight at 4° C. on rocker.
8. Wash the blot 3 times with PBST (5 min interval for each wash).
9. Incubate the blot with secondary antibody (in 5% BSA in PBST) for 60 minutes at room temperature on rocker.
10. Wash the blot 3 times with PBST. (5 min interval for each wash)

E: Detection and Quantification of Bands
Membrane is developed using Chemiluminescent substrate (Luminata forte Blots were scanned in LAS-4000 scanner (Fujifilm) followed by quantification by multi gauge (V 3.0) software.

See FIGS. 2A, 2B, 2C, and 2D

Aspects

Aspect 1. A compound of the following formula:

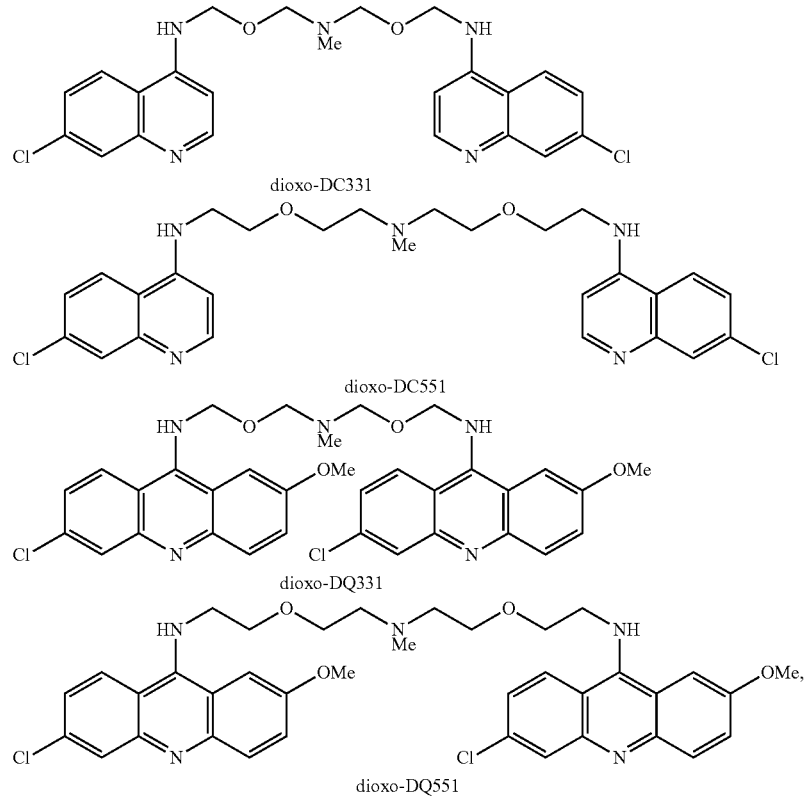

or a pharmaceutically acceptable salt, diastereomer, solvate or polymorph thereof.

Aspect 2. A compound of Aspect 1 which is Dioxo-DC331 or a pharmaceutically acceptable salt thereof.

Aspect 3. A compound of Aspect 1 which is Dioxo-DQ331 or a pharmaceutically acceptable salt thereof.

Aspect 4. A compound of Aspect 1 which is Dioxo-DC551 or a pharmaceutically acceptable salt thereof.

Aspect 5. A compound of Aspect 1 which is Dioxo-DQ551 or a pharmaceutically acceptable salt thereof.

Aspect 6. A pharmaceutical composition comprising a therapeutically effective amount of at least one compound according to any one of Aspects 1-5 in combination with a pharmaceutically acceptable carrier, additive or excipient.

Aspect 7. The composition according to Aspect 6 further comprising an effective amount of at least one additional anticancer agent.

Aspect 8. The composition according to Aspect 7 wherein said anticancer agent is a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody or a mixture thereof.

Aspect 9. The composition according to Aspect 7 wherein said anticancer agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH 2 acetate [$C_{59}H_{84}N_{18}Oi_{4}$-($C_{2}H_{4}O_{2}$)x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, erythropoietin, epoetin alfa and darbepoetin alfa, ipilumumab, vemurafenib and mixtures thereof.

Aspect 10. A method of inhibiting autophagy in a biological system in which inhibition of autophagy is desired, said method comprising exposing said biological system to an effective amount of at least one compound according to any of Aspects 1-5 hereof.

Aspect 11. A method of inhibiting or treating cancer in a patient in need comprising administering to said patient an effective amount of at least one composition according to any of Aspects 6-9.

Aspect 12. The method according to Aspect 1, wherein said cancer is metastatic.

Aspect 13. The method according to Aspect 1, wherein said cancer is recurrent.

Aspect 14. The method according to Aspect 1, wherein said cancer is a drug-resistant cancer.

Aspect 15. A method of reducing the likelihood that cancer will occur in a patient or that a cancer will metastasize in a patient comprising administering at least one composition according to any of Aspects 6-9, optionally in combination with at least one additional anticancer agent.

Aspect 16. The method according to any of Aspects 11-15, wherein said cancer is a carcinoma, cancer of the esophagus, head, kidney, liver, lung, nasopharyngeal, neck, ovary, pancreas, prostate, and stomach; a leukemia, a malignant lymphoma, a malignant melanoma; myeloproliferative diseases; a sarcoma, a tumor of the central nervous system, a germ-line tumor, lung cancer, ovarian cancer, testicular cancer, thyroid cancer, astrocytoma, esophageal cancer, pancreatic cancer, stomach cancer, liver cancer, colon cancer, melanoma, or a mixed type of neoplasia.

Aspect 17. The method according to Aspect 16, wherein said leukemia is acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia Aspect 18. The method according to Aspect 16, wherein said lymphoma is Burkitt's lymphoma, Non-Hodgkin's lymphoma or B-cell lymphoma.

Aspect 19. The method according to Aspect 16, wherein said sarcoma is Ewing's sarcoma, hemangiosarcoma, Kaposi's sarcoma, liposarcoma, myosarcomas, peripheral neuroepithelioma or synovial sarcoma.

Aspect 20. The method according to Aspect 16, wherein said tumor of the central nervous system is a glioma, astrocytoma, oligodendroglioma, ependymoma, gliobastoma, neuroblastoma, ganglioneuroma, ganglioglioma, medulloblastoma, pineal cell tumor, meningioma, meningeal sarcoma, neurofibroma, or Schwannoma.

Aspect 21. The method according to Aspect 16, wherein said germ-line tumor is bowel cancer, breast cancer, prostate cancer, cervical cancer or uterine cancer.

Aspect 22. The method according to Aspect 16, wherein said lung cancer is small cell lung cancer, mixed small cell and non-small cell cancer, pleural mesothelioma, metastatic pleural mesothelioma, small cell lung cancer or non-small cell lung cancer.

Aspect 23. The method according to Aspect 16, wherein said mixed neoplasia is carcinosarcoma and Hodgkin's disease and said tumors of mixed origin is Wilms' tumor and teratocarcinomas.

Aspect 24. The method according to Aspect 16, wherein said cancer is ovarian, breast, colon, head and neck, medulloblastoma or B-cell lymphoma, Aspect 25. The method according to cl Aspect aim 16, wherein said cancer is melanoma or non-small cell lung cancer.

Aspect 26. A method of treating a disease state or condition in a patient in need wherein said disease state or condition responds favorably to inhibition of autophagy comprising administering to said patient an effective amount of a compound according to any of Aspects 1-5 to said patient.

Aspect 27. The method according to Aspect 26, wherein said disease state or condition is rheumatoid arthritis, malaria, antiphospholipid antibody syndrome, lupus, chronic urticaria or Sjogren's disease.

Aspect 28. The method according to Aspect 26 or 27, wherein said disease state is malaria.

Aspect 29. Use of a compound according to any of Aspects 1-2 in the manufacture of a medicament for the inhibition of autophagy in a biological system in which inhibition of autophagy is desired.

Aspect 30. Use of a compound according to any of Aspects 1-5 in the manufacture of a medicament for use in inhibiting or treating cancer in a patient in need, optionally in combination with at least one additional anticancer agent.

Aspect 31. The use according to Aspect 30 wherein said cancer is metastatic.

Aspect 32. The use according to Aspect 30 wherein said cancer is drug resistant.

Aspect 33. Use of a compound according to any of Aspects 1-3 in the manufacture of a medicament for reducing the likelihood that cancer will occur in a patient or that a cancer will metastasize in a patient, optionally in combination with at least one additional anticancer agent.

Aspect 34. Use according to any of Aspects 30-33, wherein said cancer is a carcinoma, cancer of the esophagus, head, kidney, liver, lung, nasopharyngeal, neck, thyroid, ovary, pancreas, prostate, and stomach; a leukemia, a malignant lymphoma, a malignant melanoma; myeloproliferative diseases; a sarcoma, a tumor of the central nervous system, a germ-line tumor, lung cancer, ovarian cancer, testicular cancer, thyroid cancer, astrocytoma, esophageal cancer, pancreatic cancer, stomach cancer, liver cancer, colon cancer, melanoma or a mixed type of neoplasia.

Aspect 35. Use according to Aspect 34, wherein said leukemia is acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia Aspect 36. Use according to Aspect 34, wherein said lymphoma is Burkitt's lymphoma, Non-Hodgkin's lymphoma or B-cell lymphoma.

Aspect 37. Use according to Aspect 34, wherein said sarcoma is Ewing's sarcoma, hemangiosarcoma, Kaposi's sarcoma, liposarcoma, myosarcomas, peripheral neuroepithelioma or synovial sarcoma.

Aspect 38. Use according to Aspect 34, wherein said tumor of the central nervous system is a glioma, astrocytoma, oligodendroglioma, ependymoma, gliobastoma, neuroblastoma, ganglioneuroma, ganglioglioma, medulloblastoma, pineal cell tumor, meningioma, meningeal sarcoma, neurofibroma, or Schwannoma.

Aspect 39. Use according to Aspect 34, wherein said germ-line tumor is bowel cancer, breast cancer, prostate cancer, cervical cancer or uterine cancer.

Aspect 40. Use according to Aspect 34, wherein said lung cancer is small cell lung cancer, mixed small cell and non-small cell cancer, pleural mesothelioma, metastatic pleural mesothelioma, small cell lung cancer or non-small cell lung cancer.

Aspect 41. Use according to Aspect 34, wherein said mixed neoplasia is carcinosarcoma and Hodgkin's disease and said tumors of mixed origin is Wilms' tumor and teratocarcinomas.

Aspect 42. Use according to Aspect 34, wherein said cancer is ovarian, breast, colon, head and neck, medulloblastoma or B-cell lymphoma, Aspect 43. Use according to Aspect 34, wherein said cancer is melanoma or non-small cell lung cancer.

Aspect 44. Use according to Aspect 42, wherein said cancer is colon cancer.

Aspect 45. Use according to any of Aspects 30-44, wherein said additional anticancer agent is selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH 2 acetate $[C_{59}H_{84}N_{18}Oi_4-(C_2H_4O_2)x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, erythropoietin, epoetin alfa and darbepoetin alfa, ipilumumab, vemurafenib and mixtures thereof.

Aspect 46. Use according to any of Aspects 30-44, wherein said additional anticancer agent is a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR-TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody or a mixture thereof.

Aspect 47. Use of a compound according to any of Aspects 1-5 in the manufacture of a medicament for treating a disease state or condition in a patient in need wherein said disease state or condition responds favorably to inhibition of autophagy.

Aspect 48. Use according to Aspect 47, wherein said disease state or condition is rheumatoid arthritis, malaria, antiphospholipid antibody syndrome, lupus, chronic urticaria or Sjogren's disease.

Aspect 49. Use according to Aspect 48, wherein said disease state or condition is malaria.

1. Lum J J, DeBerardinis R J, and Thompson C B. Autophagy in metazoans: cell survival in the land of plenty. *Nat Rev Mol Cell Biol.* 2005; 6(6):439-48.
2. Amaravadi R K, and Thompson C B. The roles of therapy-induced autophagy and necrosis in cancer treatment. *Clin Cancer Res.* 2007; 13(24):7271-9.
3. Amaravadi R K, Yu D, Lum J J, Bui T, Christophorou M A, Evan G I, Thomas-Tikhonenko A, and Thompson C B. Autophagy inhibition enhances therapy-induced apoptosis in a Myc-induced model of lymphoma. *J Clin Invest.* 2007; 117(2):326-36.
4. Degenhardt K, Mathew R, Beaudoin B, Bray K, Anderson D, Chen G, Mukherjee C, Shi Y, Gelinas C, Fan Y, et al. Autophagy promotes tumor cell survival and restricts necrosis, inflammation, and tumorigenesis. *Cancer Cell.* 2006; 10(1):51-64.
5. Amaravadi R K. Autophagy-induced tumor dormancy in ovarian cancer. *J Clin Invest.* 2008.
6. Carew J S, Nawrocki S T, Kahue C N, Zhang H, Yang C, Chung L, Houghton J A, Huang P, Giles F J, and Cleveland J L. Targeting autophagy augments the anticancer activity of the histone deacetylase inhibitor SAHA to overcome Bcr-Abl-mediated drug resistance. *Blood.* 2007.
7. Degtyarev M, De Maziere A, Orr C, Lin J, Lee B B, Tien J Y, Prior W W, van Dijk S, Wu H, Gray D C, et al. Akt inhibition promotes autophagy and sensitizes PTEN-null tumors to lysosomotropic agents. *J Cell Biol.* 2008; 183(1):101-16.
8. Amaravadi R K, Lippincott-Schwartz J, Yin X M, Weiss W A, Takebe N, Timmer W, Dipaola R S, Lotze M T, and White E. Principles and Current Strategies for Targeting Autophagy for Cancer Treatment. *Clin Cancer Res.* 2011; 17(4):654-66.
9. Rebecca V W, Massaro R R, Fedorenko I V, Sondak V K, Anderson A R, Kim E, Amaravadi R K, Maria-Engler S S, Messina J L, Gibney G T, et al. Inhibition of autophagy enhances the effects of the AKT inhibitor MK-2206 when combined with paclitaxel and carboplatin in BRAF wild-type melanoma. *Pigment Cell Melanoma Res.* 2014; 27(3):465-78.
10. Mahalingam D, Mita M, Sarantopoulos J, Wood L, Amaravadi R, Davis L E, Mita A, Curiel T J, Espitia C M, Nawrocki S T, et al. Combined autophagy and HDAC inhibition: A phase I safety, tolerability, pharmacokinetic, and pharmacodynamic analysis of hydroxychloroquine in combination with the HDAC inhibitor vorinostat in patients with advanced solid tumors. *Autophagy.* 2014; 10(8).
11. Rangwala R, Chang Y C, Hu J, Algazy K, Evans T, Fecher L, Schuchter L, Torigian D A, Panosian J, Troxel A, et al. Combined MTOR and autophagy inhibition: Phase I trial of hydroxychloroquine and temsirolimus in patients with advanced solid tumors and melanoma. *Autophagy.* 2014; 10(8).
12. Rangwala R, Leone R, Chang Y C, Fecher L, Schuchter L, Kramer A, Tan K S, Heitjan D F, Rodgers G, Gallagher M, et al. Phase I trial of hydroxychloroquine with dose-intense temozolomide in patients with advanced solid tumors and melanoma. *Autophagy.* 2014; 10(8).
13. Rosenfeld M R, Ye X, Supko J G, Desideri S, Grossman S A, Brem S, Mikkelson T, Wang D, Chang Y C, Hu J, et al. A phase I/II trial of hydroxychloroquine in conjunction with radiation therapy and concurrent and adjuvant temozolomide in patients with newly diagnosed glioblastoma multiforme. *Autophagy.* 2014; 10(8).
14. Vance D, Shah M, Joshi A, and Kane R S. Polyvalency: a promising strategy for drug design. *Biotechnol Bioeng.* 2008; 101(3):429-34.
15. Shrivastava A, Nunn A D, and Tweedle M F. Designer peptides: learning from nature. *urr Pharm Des.* 2009; 15(6):675-81.
16. Girault S, Grellier P, Berecibar A, Maes L, Lemiere P, Mouray E, Davioud-Charvet E, and Sergheraert C. Antiplasmodial activity and cytotoxicity of bis-, tris-, and tetraquinolines with linear or cyclic amino linkers. *J Med Chem.* 2001; 44(11):1658-65.
17. Vennerstrom J L, Ager A L, Jr., Dorn A, Andersen S L, Gerena L, Ridley R G, and Milhous W K. Bisquinolines. 2. Antimalarial N,N-bis(7-chloroquinolin-4-yl)heteroalkanediamines. *J Med Chem.* 1998; 41(22):4360-4.
18. Burnett J C, Schmidt J J, Stafford R G, Panchal R G, Nguyen T L, Hermone A R, Vennerstrom J L, McGrath C F, Lane D J, Sausville E A, et al. Novel small molecule inhibitors of botulinum neurotoxin A metalloprotease activity. *Biochem Biophys Res Commun.* 2003; 310(1):84-93.

19. Hu C, Raja Solomon V, Cano P, and Lee H. A 4-aminoquinoline derivative that markedly sensitizes tumor cell killing by Akt inhibitors with a minimum cytotoxicity to non-cancer cells. *Eur J Med Chem.* 2010; 45(2):705-9.
20. Solomon V R, Hu C, and Lee H. Design and synthesis of chloroquine analogs with anti-breast cancer property. *Eur J Med Chem.* 2010; 45(9):3916-23.
21. McAfee Q, Zhang Z, Samanta A, Levi S M, Ma X H, Piao S, Lynch J P, Uehara T, Sepulveda A R, Davis L E, et al. Autophagy inhibitor Lys05 has single-agent antitumor activity and reproduces the phenotype of a genetic autophagy deficiency. *Proc Natl Acad Sci USA.* 2012; 109(21):8253-8.
22. Cadwell K, Liu J Y, Brown S L, Miyoshi H, Loh J, Lennerz J K, Kishi C, Kc W, Carrero J A, Hunt S, et al. A key role for autophagy and the autophagy gene Atg16l1 in mouse and human intestinal Paneth cells. *Nature.* 2008; 456(7219):259-63.
23. Tanida I, Ueno T, and Kominami E. LC3 conjugation system in mammalian autophagy. *Int J Biochem Cell Biol.* 2004; 36(12):2503-18.

What is claimed:

1. A compound of formula I, II, or III:

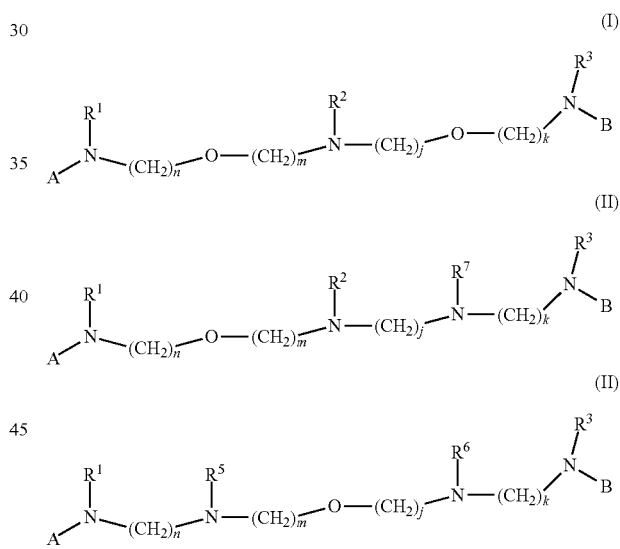

or a pharmaceutically acceptable salt thereof, wherein

A is

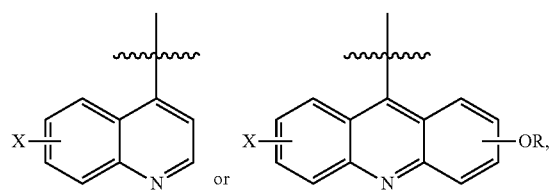

wherein X is F, Cl, or Br and R is H, $C_{1-6}$alkyl, or —C(O)$C_{1-6}$alkyl;

B is

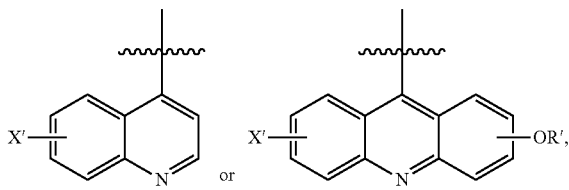

wherein X' is F, Cl, or Br and R' is H, $C_{1-6}$alkyl, or —C(O)$C_{1-6}$alkyl;

$R^1$ is H, $C_{1-6}$alkyl, —C(O)$C_{1-6}$alkyl, alkaryl, or alkheteroaryl;

$R^2$ is H, $C_{1-6}$alkyl, —C(O)$C_{1-6}$alkyl, alkaryl, or alkheteroaryl;

$R^3$ is H, $C_{1-6}$alkyl, —C(O)$C_{1-6}$alkyl, alkaryl, or alkheteroaryl;

$R^4$ is H, $C_{1-6}$alkyl, —C(O)$C_{1-6}$alkyl, alkaryl, or alkheteroaryl;

$R^5$ is H, $C_{1-6}$alkyl, —C(O)$C_{1-6}$alkyl, alkaryl, or alkheteroaryl;

$R^6$ is H, $C_{1-6}$alkyl, —C(O)$C_{1-6}$alkyl, alkaryl, or alkheteroalkyl;

n is 1, 2, 3, 4, or 5;

m is 1, 2, 3, 4, or 5;

j is 1, 2, 3, 4, or 5; and k is 1, 2, 3, 4, or 5.

2. The compound of claim 1 that is a compound of formula I, or a pharmaceutically acceptable salt thereof.

3. The compound of claim 1 that is a compound of formula II, or a pharmaceutically acceptable salt thereof.

4. The compound of claim 1 that is a compound of formula III, or a pharmaceutically acceptable salt thereof.

5. The compound of claim 1, wherein n is 1-3.

6. The compound of claim 1, wherein m is 1-3.

7. The compound of claim 1, wherein j is 1-3.

8. The compound of claim 1, wherein k is 1-3.

9. The compound of claim 1, wherein (i) A is

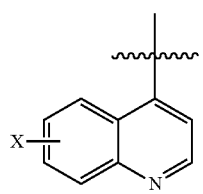

and B is

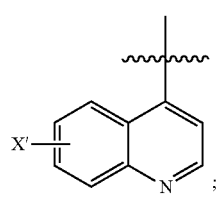

or (ii) A is

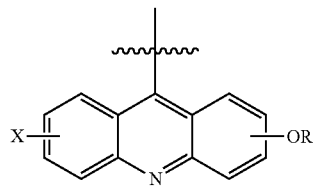

and B is

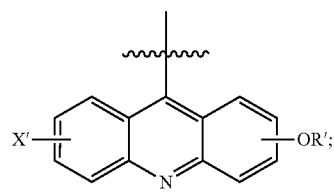

or (iii) A is

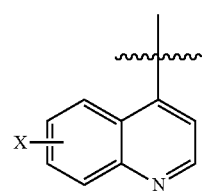

and B is

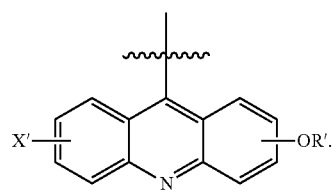

10. The compound of claim 1, wherein one or both of X and X' is Cl.

11. The compound of claim 1, wherein one or both of R and R' is $C_{1-6}$alkyl.

12. The compound of claim 1, wherein one or more of $R^1$ to $R^6$ is H.

13. The compound of claim 1, wherein one or more of $R^1$ to $R^6$ is $C_{1-6}$alkyl.

14. The compound of claim 1, wherein one or more of $R^1$ to $R^6$ is -C(O)$C_{1-6}$ alkyl.

15. The compound of claim 1, wherein one or more of $R^1$ to $R^6$ is alkaryl.

16. The compound of claim 1, wherein one or more of $R^1$ to R is alkheteroaryl.

17. A pharmaceutical composition comprising a compound of claim 1, or a pharmaceutically acceptable salt thereof, and a pharmaceutically acceptable excipient.

18. A method of ameliorating cancer, rheumatoid arthritis, malaria, antiphospholipid antibody syndrome, lupus, chronic urticaria or Sjogren's disease in a subject comprising administering to the subject a compound of claim 1, or a pharmaceutically acceptable salt thereof.

19. The method of claim 18, further comprising administering to the subject an additional chemotherapeutic agent.

20. The method of claim 18, wherein the cancer is a carcinoma, cancer of the esophagus, head, kidney, liver, lung, nasopharyngeal, neck, ovary, pancreas, prostate, and stomach; a leukemia, a malignant lymphoma, a malignant melanoma; myeloproliferative diseases; a sarcoma, a tumor of the central nervous system, a germ-line tumor, lung cancer, ovarian cancer, testicular cancer, thyroid cancer, astrocytoma, esophageal cancer, pancreatic cancer, stomach cancer, liver cancer, colon cancer, melanoma, or a mixed type of neoplasia.

21. The method of claim 20, wherein said leukemia is acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; the lymphoma is Burkitt's lymphoma, Non-Hodgkin's lymphoma or B-cell lymphoma; the sarcoma is Ewing's sarcoma, hemangiosarcoma, Kaposi's sarcoma, liposarcoma, myosarcoma, peripheral neuroepithelioma or synovial sarcoma; the tumor of the central nervous system is a glioma, astrocytoma, oligodendroglioma, ependymoma, glioblastoma, neuroblastoma, ganglioneuroma, ganglioglioma, medulloblastoma, pineal cell tumor, meningioma, meningeal sarcoma, neurofibroma, or Schwannoma; the germ-line tumor is bowel cancer, breast cancer, prostate cancer, cervical cancer or uterine cancer; the lung cancer is small cell lung cancer, mixed small cell and non-small cell cancer, pleural mesothelioma, metastatic pleural mesothelioma, small cell lung cancer or non-small cell lung cancer; the mixed neoplasia is carcinosarcoma and Hodgkin's disease and said tumors of mixed origin is Wilms' tumor and teratocarcinoma; the cancer is ovarian, breast, colon, head and neck, medulloblastoma or B-cell lymphoma; or the cancer is melanoma or non-small cell lung cancer.

22. The method of claim 18, wherein the disease state or condition is malaria.

23. A method of inhibiting autophagy in a biological system comprising exposing the biological system to a compound of claim 1, or a pharmaceutically acceptable salt thereof.

24. The compound of claim 1, that is:

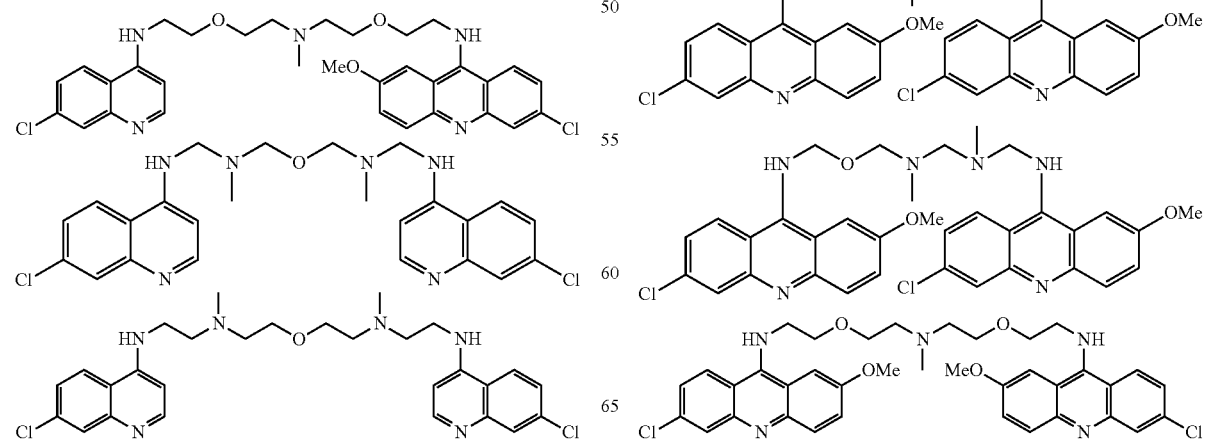

-continued
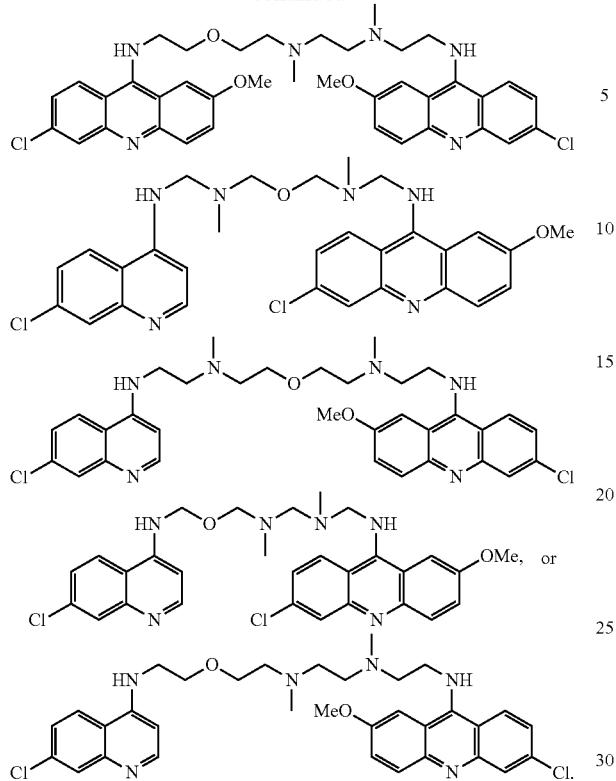
* * * * *

UNITED STATES PATENT AND TRADEMARK OFFICE
CERTIFICATE OF CORRECTION

PATENT NO. : 12,343,339 B2
APPLICATION NO. : 17/613648
DATED : July 1, 2025
INVENTOR(S) : Jeffrey Winkler et al.

It is certified that error appears in the above-identified patent and that said Letters Patent is hereby corrected as shown below:

In the Specification

Under Column no. 2, Line nos. 3-7, Replace:

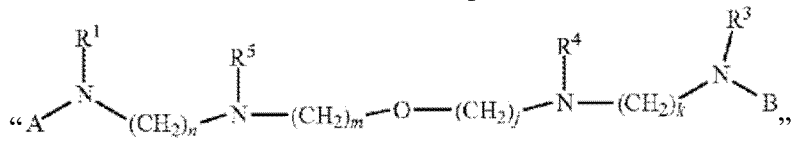

With:

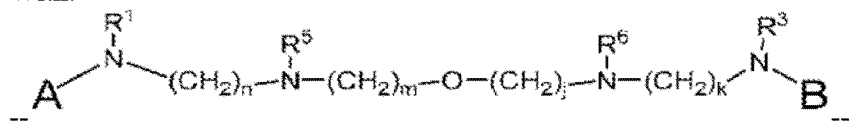

Under Column no. 7, Line nos. 42-47, Replace:

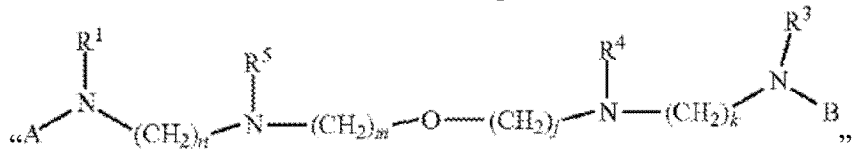

With:

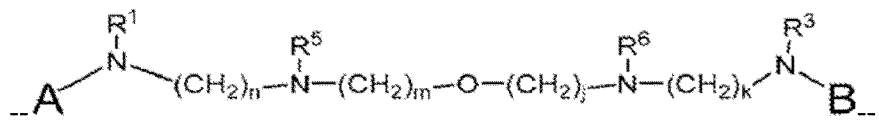

Under Column no. 9, Line no. 50, Replace:

Signed and Sealed this
Twenty-sixth Day of August, 2025

Coke Morgan Stewart
*Acting Director of the United States Patent and Trademark Office*

"
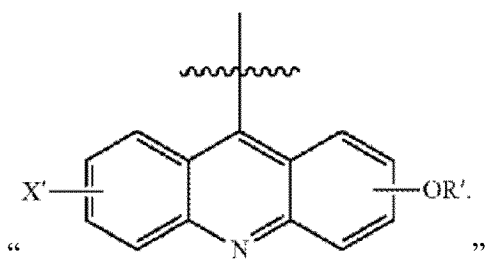
"
With:
--
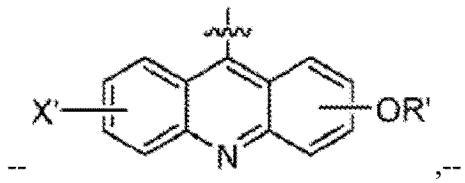
,--
Under Column no. 10, Line no. 39, Replace:
"R¹"
With:
--R'--
Under Column no. 33, Line no. 39, Replace:
"flu);"
With:
--Bu);--
Under Column no. 33, Line no. 40, Replace:
"tBlu);"
With:
--tBu);--
Under Column no. 33, Line no. 41, Replace:
"flu)"
With:
--Bu)--
Under Column no. 34, Line no. 36, Replace:
"flu);"
With:
--Bu);--
Under Column no. 34, Line no. 36, Replace:
"flu)"
With:
--Bu)--
Under Column no. 34, Line no. 38, Replace:

"Blu,"
With:
--Bu,--

Under Column no. 34, Line no. 38, Replace:
"tflu);"
With:
--tBu);--

Under Column no. 34, Line no. 39, Replace:
"flu),"
With:
--Bu),--

Under Column no. 51, Line no. 40, Replace:
"IPdRi"
With:
--IPdR$_1$--

Under Column no. 54, Line nos. 50-52, Replace:

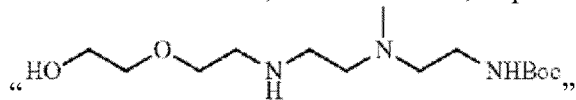

With:

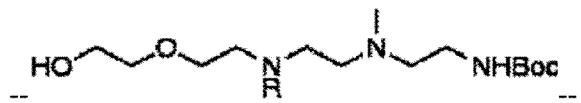
--                                                                        --

Under Column no. 57, Line nos. 34-36, Replace:

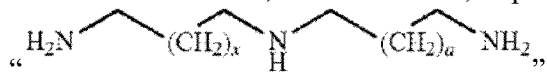

With:

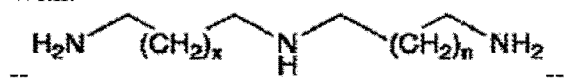
--                                                        --

Under Column no. 61, Line no. 49, Replace:
"THE"
With:
--THF--

Under Column no. 61, Line no. 57, Replace:
"C$_2$"
With:
--Cl$_2$--

Under Column no. 63, Line no. 35, Replace:
"(Rf'$_2$"

With:
--(Rf=--

Under Column no. 67, Line no. 62, Replace:
"IL"
With:
--µL--

Under Column no. 68, Line no. 16, Replace:
"HIPLC"
With:
--HPLC--

Under Column no. 68, Line no. 17, Replace:
"HIPLC"
With:
--HPLC--

Under Column no. 70, Line no. 47, Replace:
"HIPLC."
With:
--HPLC.--

Under Column no. 70, Line no. 64, Replace:
"Blue ™"
With:
--Blue™--

Under Column no. 71, Line no. 2, Replace:
"4 ml):"
With:
--1 ml):--

Under Column no. 71, Line no. 3, Replace:
"ml"
With:
--µl--

Under Column no. 71, Line no. 5, Replace:
"DLDln&"
With:
--DLD1 &--

Under Column no. 77, Line no. 35, Replace:
"IPdRi"
With:

CERTIFICATE OF CORRECTION (continued)
U.S. Pat. No. 12,343,339 B2

--IPdR$_1$--

Under Column no. 81, Line no. 12, Replace:
"IPdRi"
With:
--IPdR$_1$--

In the Claims

Under Column no. 84, Claim 1, Line no. 44, Replace:
"(II)"
With:
--(III)--

Under Column no. 86, Claim 14, Line no. 53, Replace:
"is-C"
With:
--is -C--

Under Column no. 86, Claim 16, Line no. 57, Replace:
"Reis"
With:
--R$^6$ is--